USOO5540494A

United States Patent [19]
Purvis, Jr. et al.

[11] Patent Number: 5,540,494
[45] Date of Patent: Jul. 30, 1996

[54] METHOD AND APPARATUS FOR DETERMINING ABSOLUTE PARTICLE SIZE, SURFACE AREA AND VOLUME NORMALIZED FLUORESCENCE USING FORWARD ANGLE LIGHT SCATTER INTENSITY IN FLOW CYTOMETRY

[76] Inventors: Norman B. Purvis, Jr., 1010 Lawnview Ct., Franklin, Tenn. 37064; Todd D. Giorgio, 3608 Westbrook Dr., Nashville, Tenn. 37205

[21] Appl. No.: 253,375

[22] Filed: Jun. 3, 1994

[51] Int. Cl.[6] .......................... G01N 21/00; G01N 15/02
[52] U.S. Cl. ............................ 356/73; 356/336; 356/338; 356/340; 356/343
[58] Field of Search ................................ 356/72–73, 39, 356/336, 340, 343, 338; 250/252.1 A

[56] References Cited

U.S. PATENT DOCUMENTS

| | | | |
|---|---|---|---|
| 2,816,479 | 12/1957 | Sloan | 356/336 |
| 3,695,765 | 10/1972 | Bol et al. | 356/336 |
| 3,710,933 | 1/1973 | Fulwyler et al. | 356/73 |
| 3,873,209 | 3/1975 | Wilcock . | |
| 4,263,508 | 4/1981 | Leary et al. | 356/335 |
| 4,360,270 | 11/1982 | Jeck | 356/338 |
| 4,765,737 | 8/1988 | Harris et al. | 356/336 |
| 4,794,806 | 1/1989 | Nicoli et al. | 250/576 |
| 4,857,451 | 8/1989 | Schwartz | 435/7 |
| 5,007,737 | 4/1991 | Hirleman, Jr. | 356/336 |
| 5,041,733 | 8/1991 | Noguchi et al. | 250/461 |
| 5,056,918 | 10/1991 | Bott et al. | 356/336 |
| 5,090,808 | 2/1992 | Ishikawa et al. | 356/336 |
| 5,104,221 | 4/1992 | Bott et al. | 356/336 |
| 5,105,093 | 4/1992 | Niwa | 356/336 |
| 5,138,170 | 8/1992 | Noguchi et al. | 250/461 |
| 5,325,168 | 6/1994 | Nakamoto et al. | 356/73 |

OTHER PUBLICATIONS

James A. Hardy & Leon Wheeless, Jr. pp. 857–863, 1977 (copy attached) "Application of Fraunhofer Diffraction Theory to Feature–Specific Detector Design" The Journal of Histochemistry and Cytochemistry.

Jovin, et al. pp. 269–283, 1976 (copy attached) "Automatic Sizing & Separation of Particles By Ratios of Light ... " The Journal of Histochemistry and Cytochem.

P. F. Mullaney & P. N. Dean pp. 764–772 vol. 10, 1970 (copy attached) "The Small Angle Light Scattering of Biological Cells", Biophysical Journal.

Brunsting pp. 607–615, 1974 (copy enclosed) "Can Light-–Scattering Techniques Be Applied to Flow–Through Cell Analysis?" The Journal of Histochemistry and Cytochemistry.

*Primary Examiner*—Frank Gonzalez
*Assistant Examiner*—Jason D. Eisenberg
*Attorney, Agent, or Firm*—Waddey & Patterson; Mark J. Patterson

[57] ABSTRACT

A method and apparatus are described for flow cytometric absolute sizing of individual biological particles and for determining and reporting fluorescence data which is surface area or volume normalized.

9 Claims, 28 Drawing Sheets

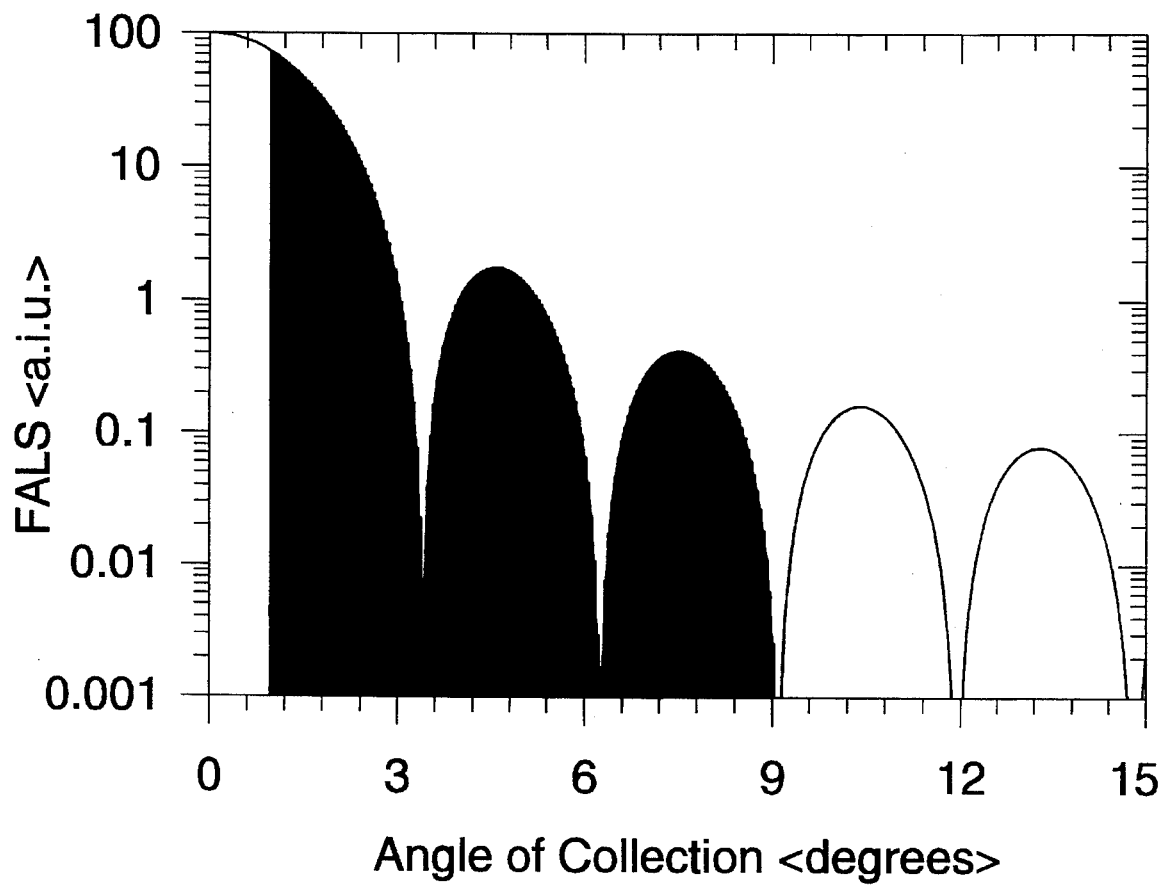

FIG. 2  A typical diffraction pattern intensity plot predicted using FTD for a spherical particle with a radius of 5 μm and an illumination wavelength of 488 nm. The peaks and troughs represent the angular location of bright and dark concentric bands projected on the focal plane. The shaded area represents the integrated FALS intensity measurement predicted for a flow cytometer with limiting angles of collection of θmax=9.0°.

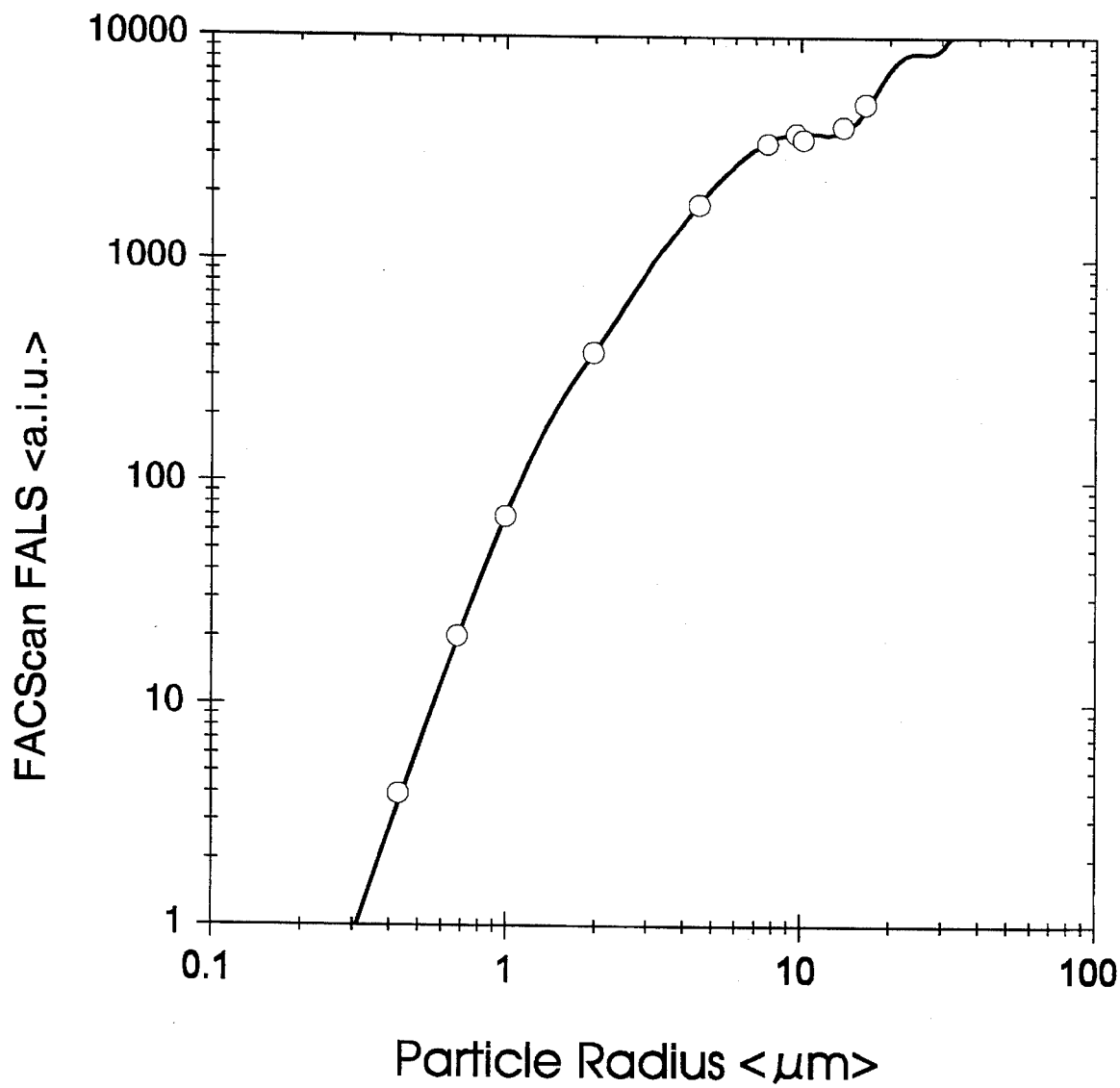
FIG. 3  Particle radius versus the FALS intensity measured on a B-D FACScan flow cytometer. The plot predicted by FDT (solid line), with parameters C=39.057, θmin = 0.95°, and θmax = 8.6°, gives the best fit to the measured FALS intensity measurements of polystyrene microspheres (O) of known radius. (a.i.u. = arbitrary intensity units)

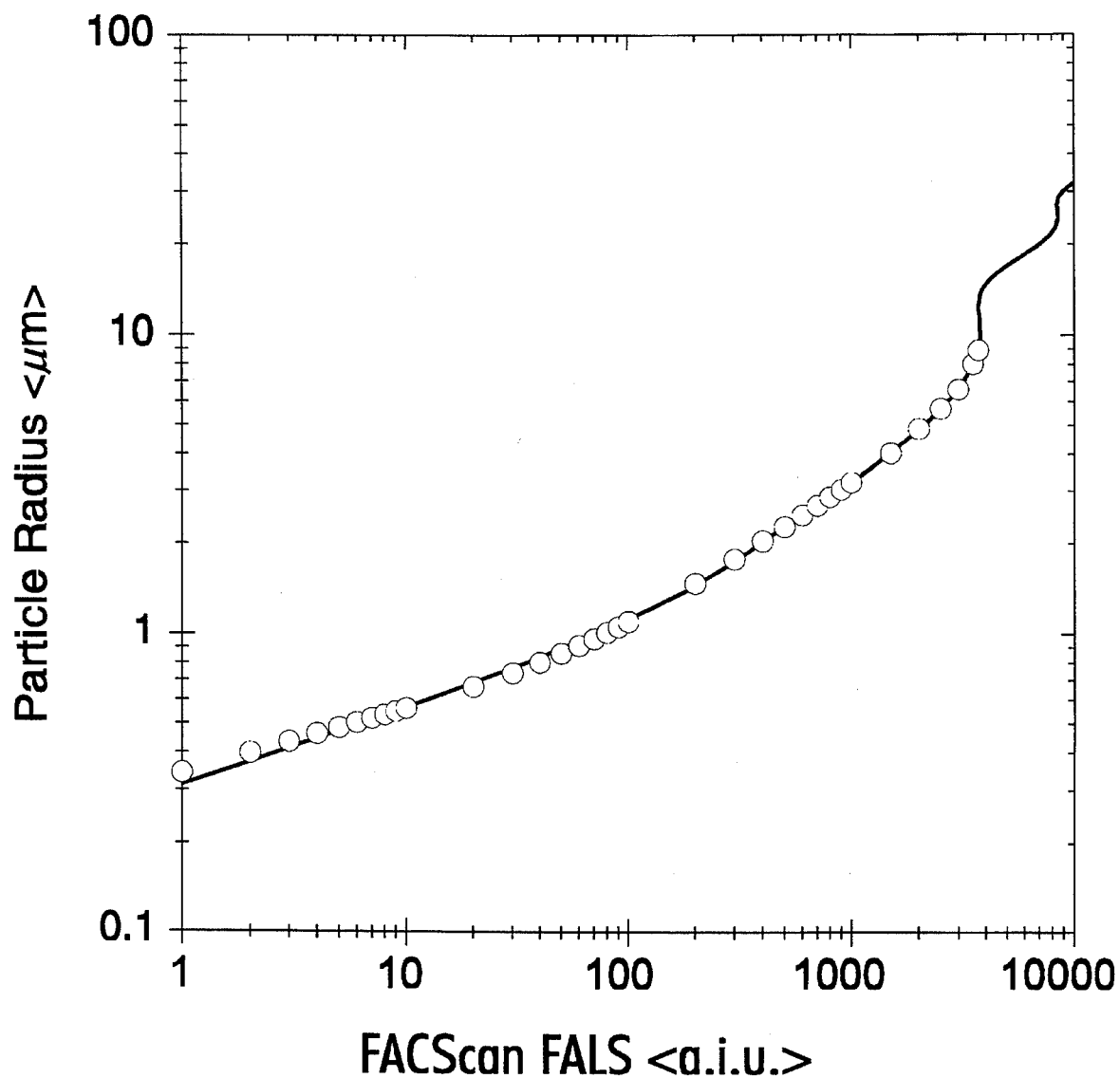
FIG. 4 Particle radius versus the FALS intensity measured on a B-D FACScan flow cytometer. The plot predicted by FDT (solid line), with parameters C=39.057, $\theta min = 0.95°$, and $\theta max = 8.6°$. The curve fitted (o) polynomial equation (Equation 4) from the limited FALS range of 1 to 3700 arbitrary intensity units (a.i.u.).

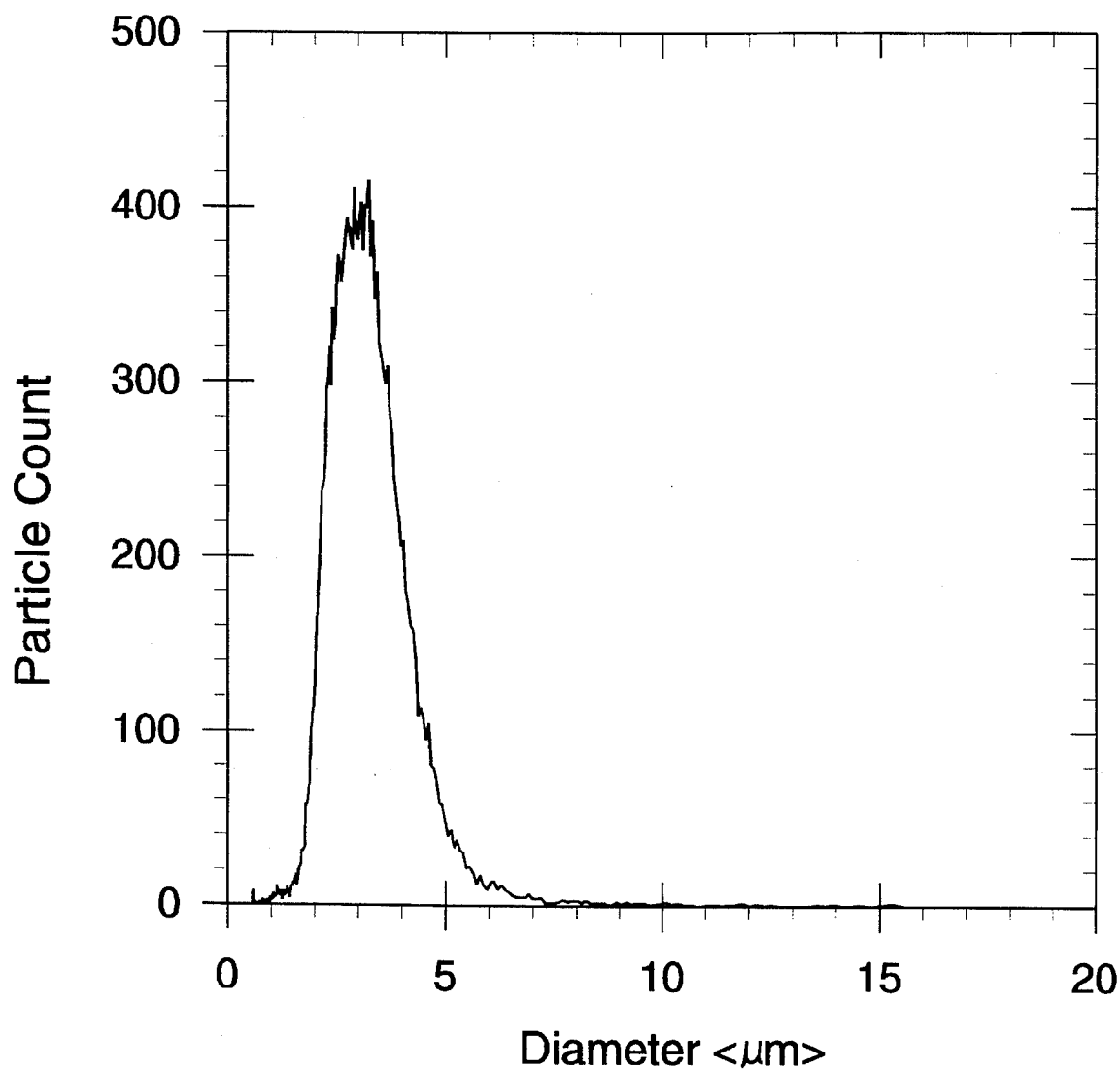
FIG. 5 A typical platelet size distribution of paraformaldehyde fixed resting platelets measured optically on the FACScan flow cytometer. The mean platelet diameter was determined to be 2.93 μm on the FACScan. The mean platelet diameter of the same platelet sample was determined to be 2.60 μm on a standard electronic particle counter.

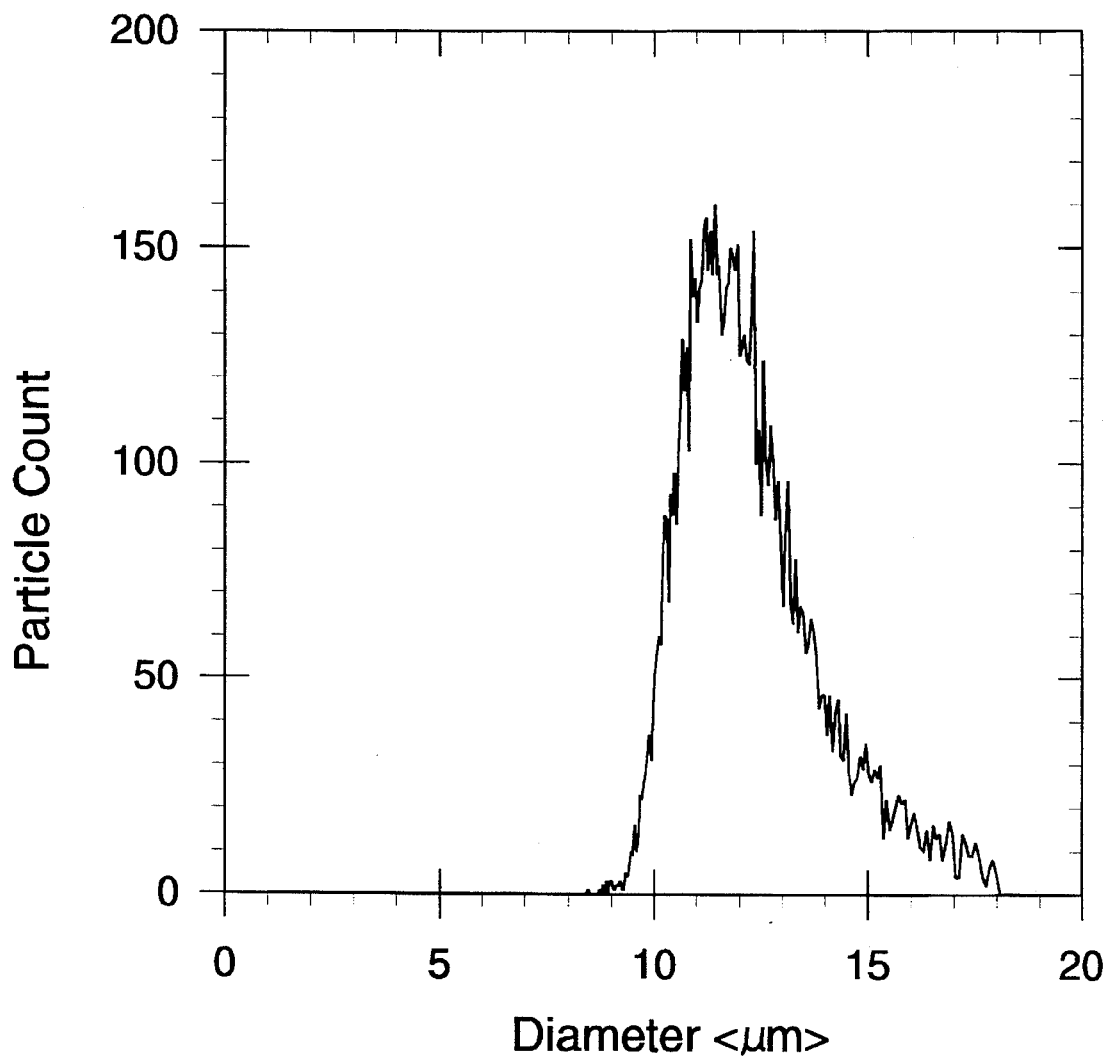
FIG. 6  A typical isolated lymphocyte size distribution of paraformaldehyde fixed lymphocytes measured optically on the FACScan flow cytometer. The mean lymphocyte diameter was determined to be 12.01 μm on the FACScan. The mean lymphocytes diameter of the same sample was determined to be 10.93 μm on a standard electronic particle counter.

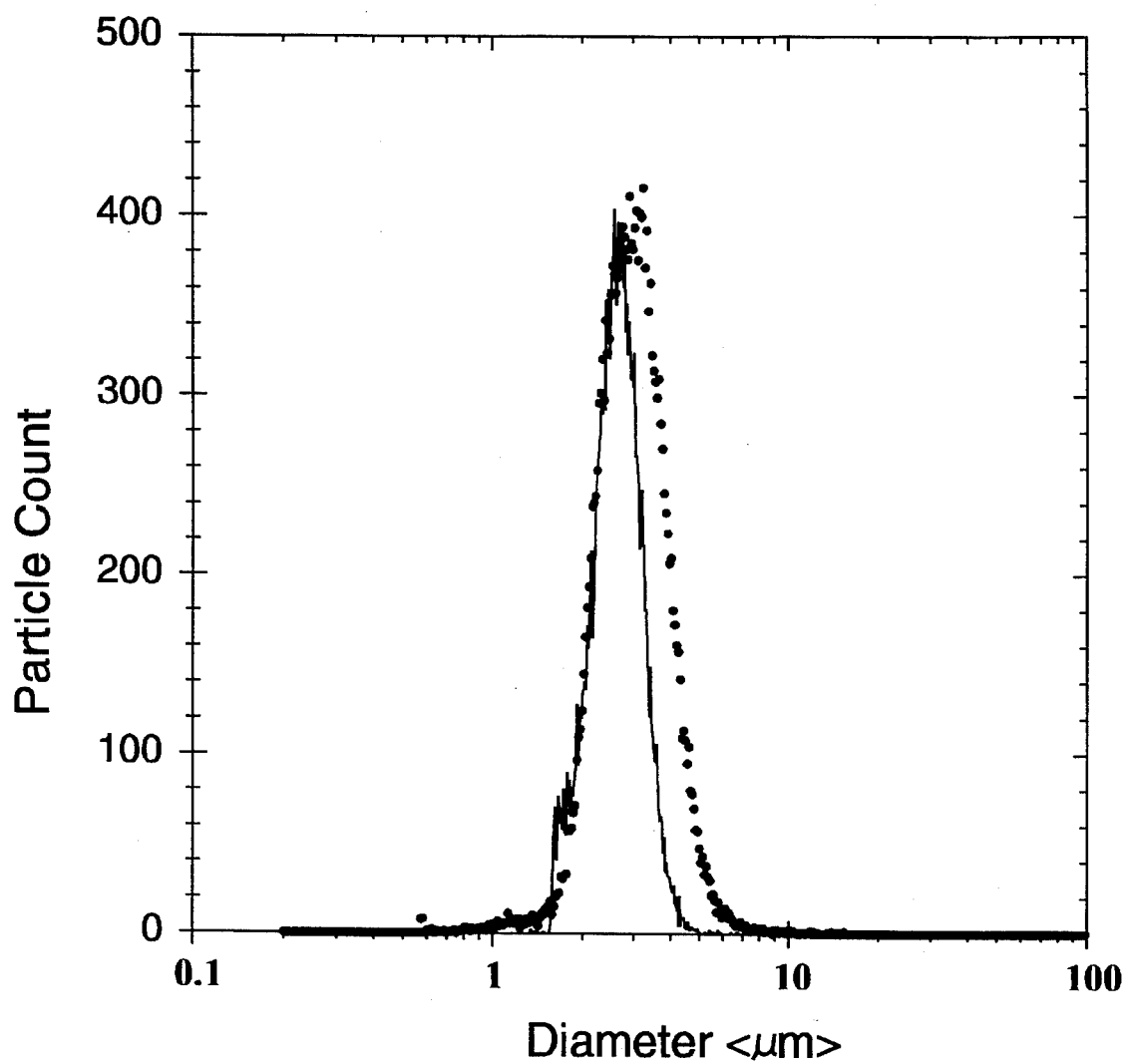
FIG. 7 Comparison of the size distribution of normal, control platelets measured on an electronic particle counter (solid line) and calculated from the FACScan FALS intensity measurements using the derived semi-empirical equation (●).

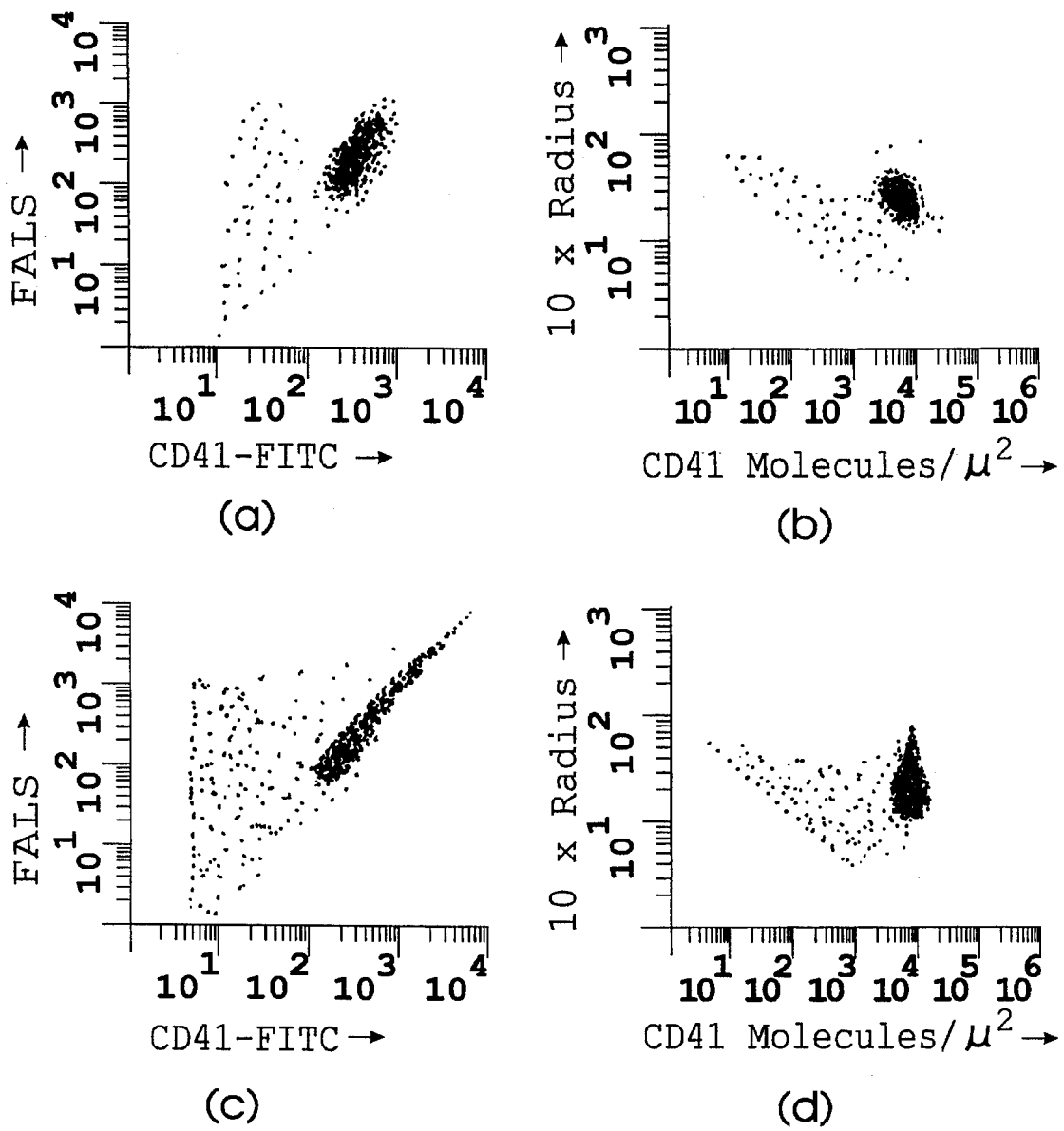

FIG. 8 Comparison of CD41-FITC binding to platelet GP IIb/IIIa before and after platelet activation using 1.0 μM PMA.
The dot plots shown are of: (a) raw CD41-FITC flourescence per event for control, non-activated platelets; (b) surface area normalized CD41 binding density (bound CD41 molecules per $\mu^2$) for control, non-activated platelets; (c) raw CD41-FITC flourescence per event for PMA activated platelets; and (d) surface area normalized CD41 binding density for PMA activated platelets.

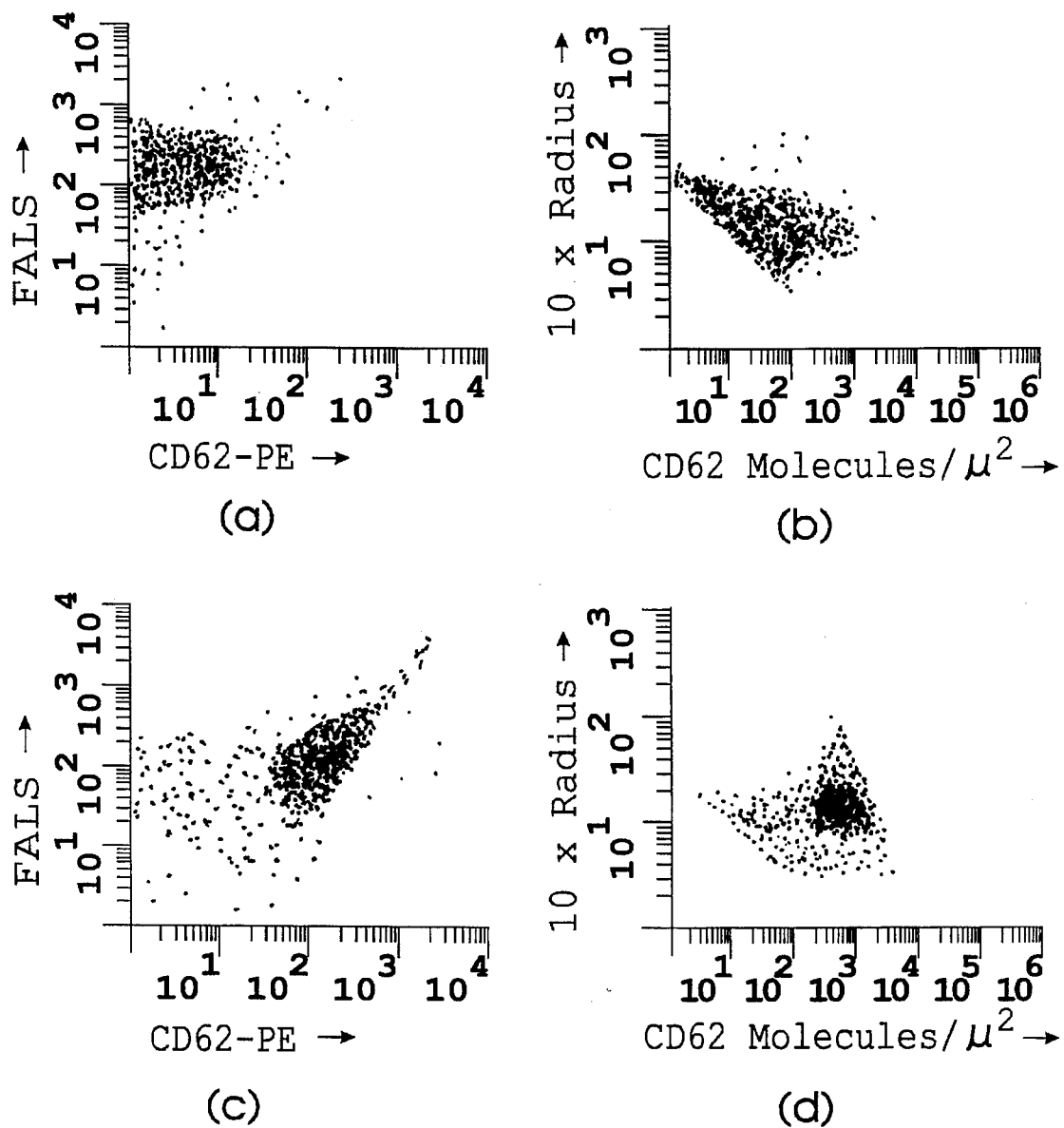

FIG. 9 Comparison of CD62 binding to platelet GMP-140 before and after platelet activation using 1.0 μM PMA. The dot plots shown are of: (a) raw CD62-PE flourescence per event for control, non-activated platelets; (b) surface area normalized CD62 binding density (bound CD62 molecules per $\mu^2$) for control, non-activated platelets; (c) raw CD62-PE flourescence per event for PMA activated platelets; and (d) surface area normalized CD62 binding density for PMA activated platelets.

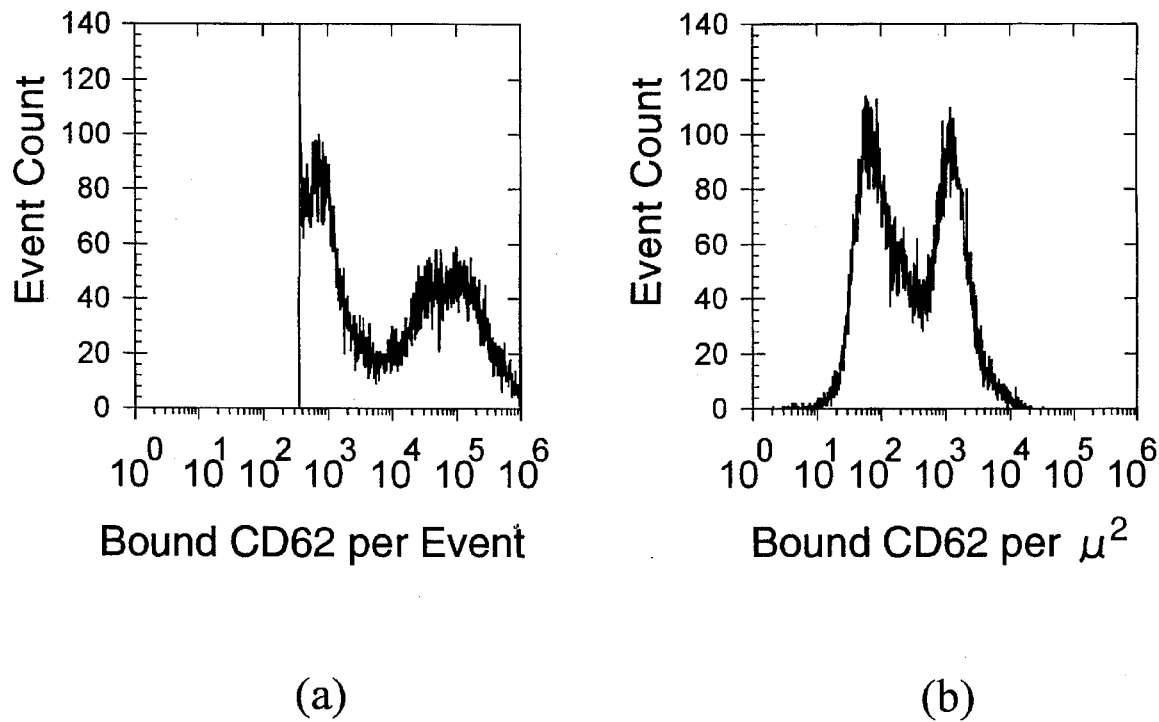
FIG. 10 Distinct bimodal distribution of CD62 binding density positively identified after surface area normalization (a) unusual CD62 binding distribution per event (b) bimodal CD62 binding distribution per µm². Illustrates two distinct platelet populations based on CD62 binding density following platelet activation with 0.1 µM PMA for 5 minutes.

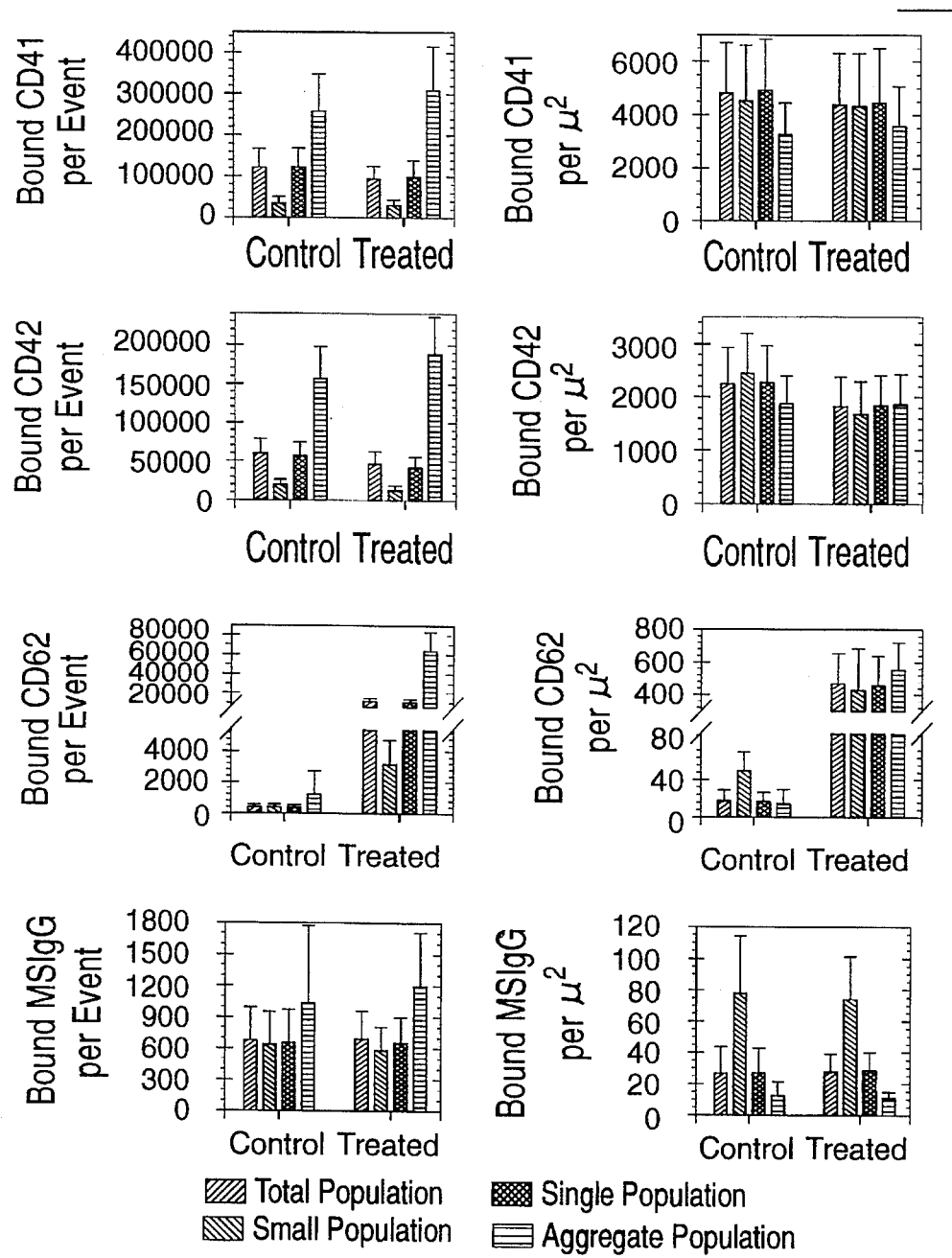

FIG. 11 Comparison of CD41, CD42, CD62, and MSIgG binding to control, non-stimulated platelets with and without surface area normalization. The plots report the mean +/- standard deviation of 11 independent experiments and represent the number of bound molecules of monoclonal antibody per event of per $\mu m^2$. The following radii ranges define the size populations analyzed: Total Population $0.33m\mu \leq r \leq 8.98\mu m$, Small Population $0.33m\mu \leq r < 0.91\mu m$, Single Population $0.91\mu m \leq r \leq 2.19\mu m$, Aggregate Population $2.19\mu m \leq r \leq 8.98\mu m$

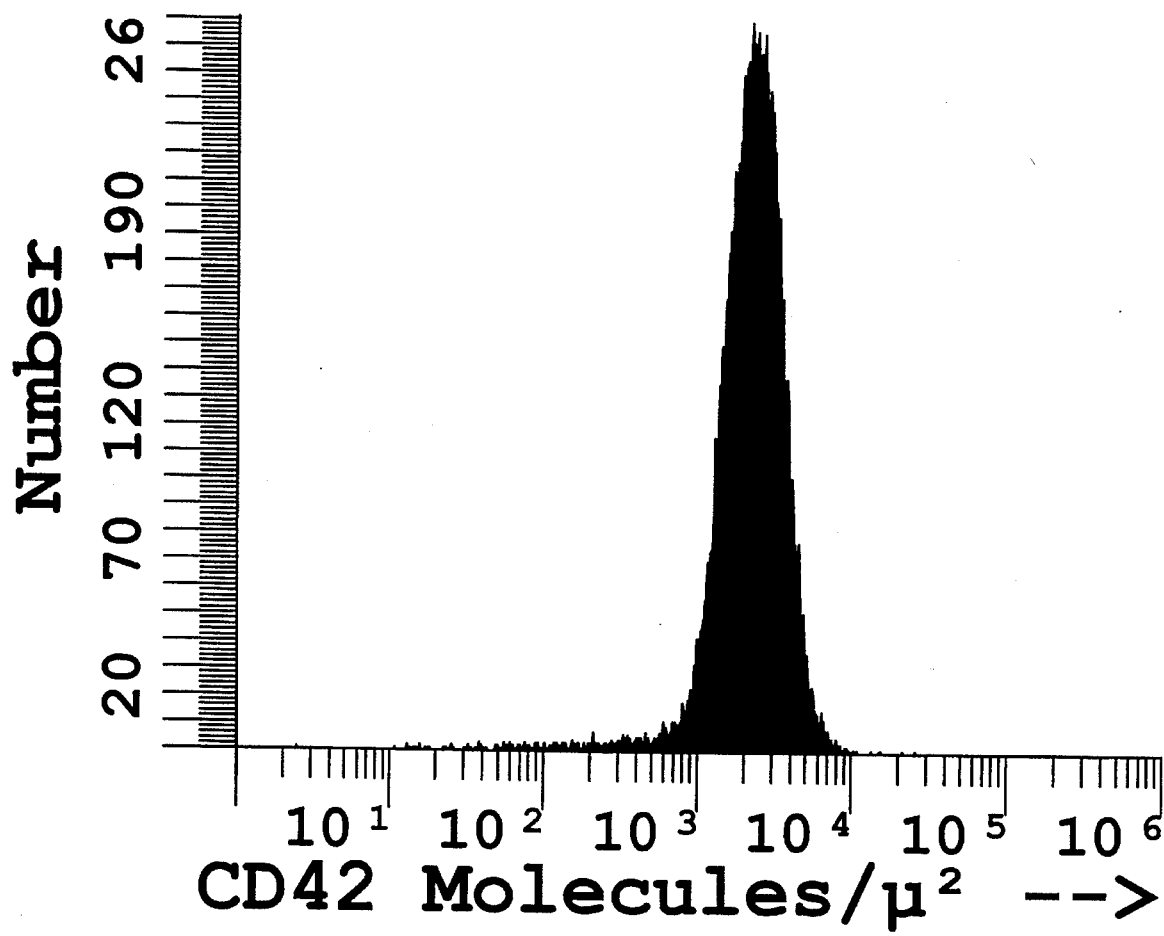
FIG. 12 Typical CD42 binding density distribution for non-activated control platelets analyzed of the FACScan flow cytometer. The mean CD42 molecules per $\mu^2$. This binding distribution may be interpreted as the GP Ib surface receptor concentration, since CD42 is reported to bind to GP Ib in a 1:1 ratio.

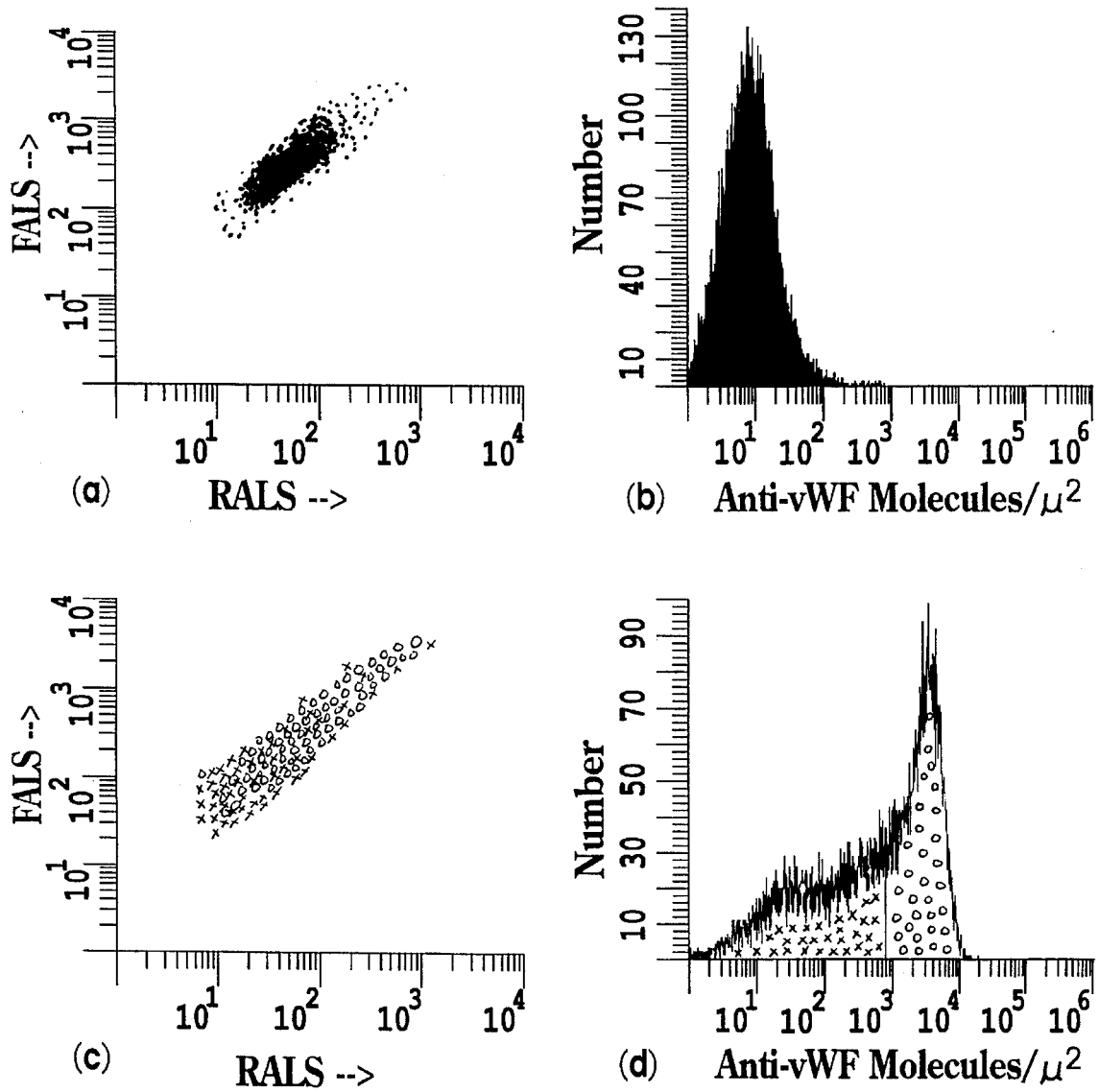

FIG. 13 Typical Anti-vWF binding density distributions and corresponding forward angle light scatter (FALS) versus right angle light scatter (RALS) profiles analyzed on the FACScan flow cytometer. Plots (a) and (b) are corresponding plots measured from non-activated control platelets (mean Anti-vWF binding density = 8 bound Anti-vWF molecules per $\mu^2$). Plots (c) and (d) are corresponding plots measured from platelets stimulated for 5 minutes with 1.5 mg/ml ristocetin (mean Anti-vWF binding density = 557 bound Anti-vWF molecules per $\mu^2$). Plots (c) and (d) has been symbol gated based on high (o;55% with a mean = 2721 bound Anti-vWF molecules per $\mu^2$) and low (x; 45% with a mean = 83 bound Anti-vWF binding density expression on ristocetin stimulated platelets.

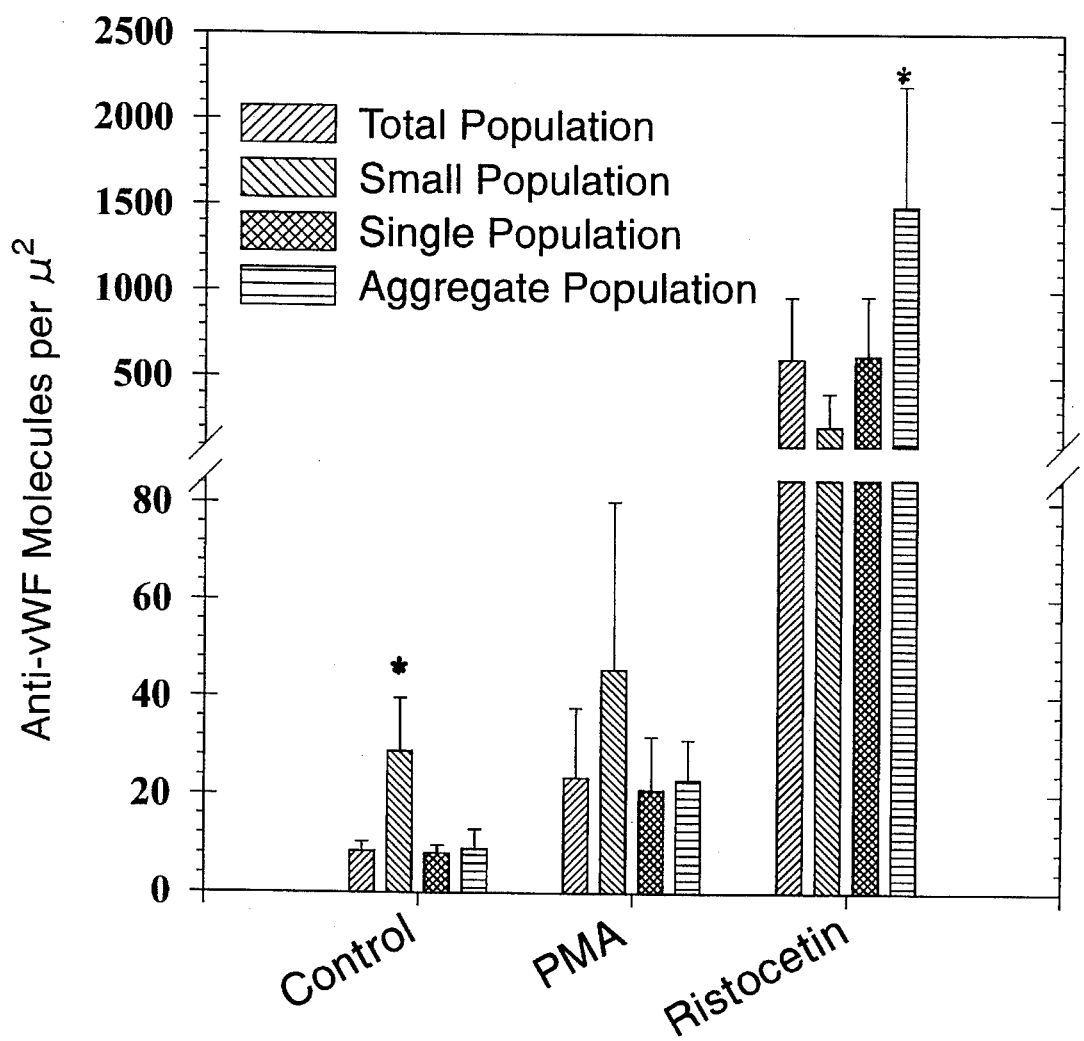

FIG. 14  Anti-vWF binding density analysis by platelet size categories for control, 1.0 µM PMA, and 1.5 mg/ml ristocetin stimulated platelet samples. The platelet population was divided into the following platelet diameter (d) ranges: total population $0.66m\mu \leq d \leq 17.96\mu m$, small population $0.66m\mu \leq d < 1.82\mu m$, single population $1.82\mu m \leq d \leq 4.36\mu m$, a aggregate population $1.36\mu m \leq d \leq 17.96\mu m$. No significant differences were observed between control and PMA stimulated samples. However, the Anti-vWF binding density of ristocetin stimulated platelets was significantly different from both control and PMA stimulated platelets (two-way ANOVA, $p<0.05$). The "*" denotes significant difference between a size category and all other size categories within that sample treatment group.

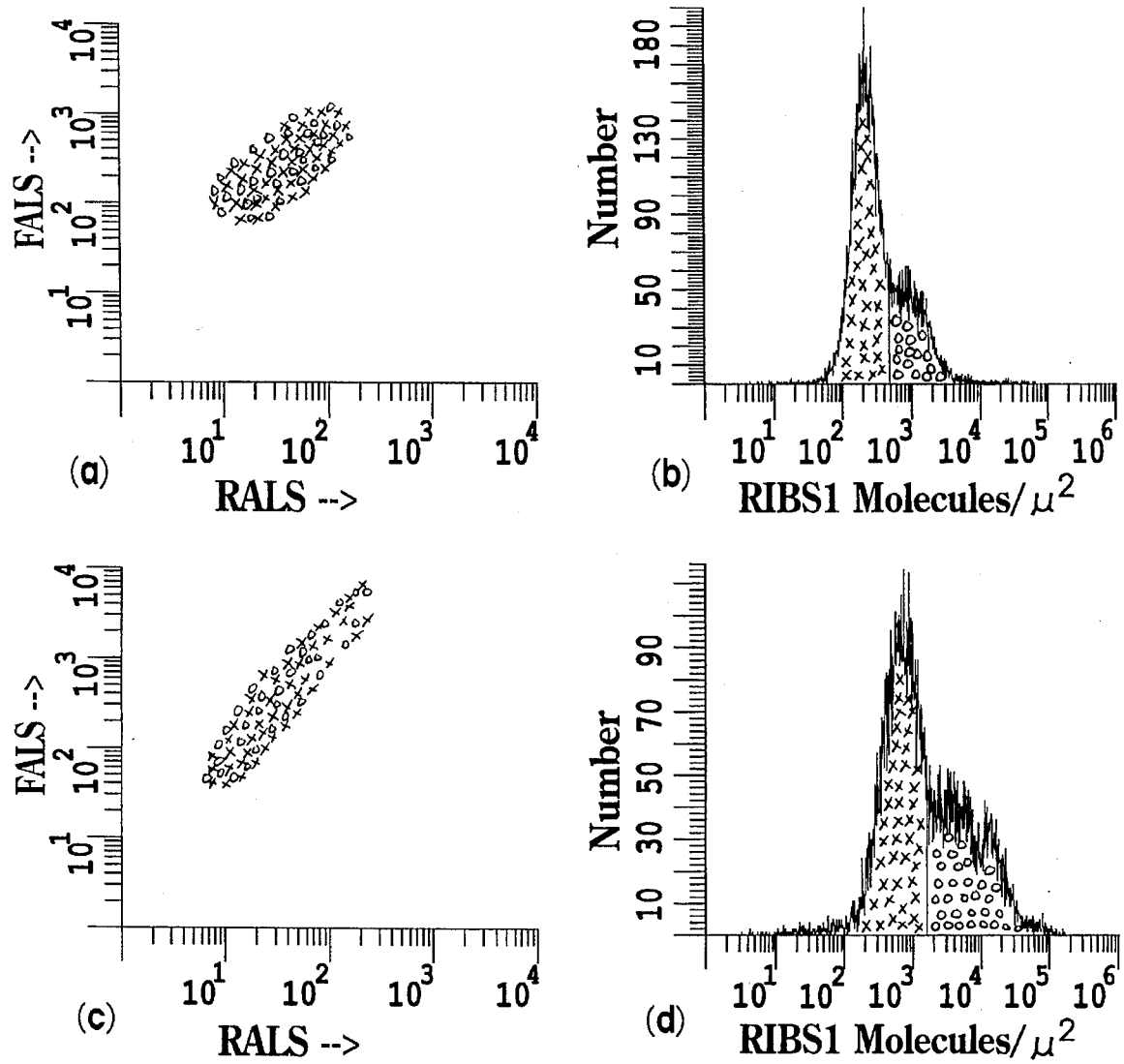

FIG. 15 Typical RIBS1 binding density distributions and corresponding FALS versus RALS profiles analyzed on the FACScan flow cytometer. Plots (a) and (b) are corresponding plots measured from non-activated control platelets (mean RIBS1 binding density = 343 bound RIBS1 molecules per $\mu^2$). Plots (c) and (d) are corresponding plots measured from platelets stimulated for 5 minutes with 1.0 $\mu$M PMA (mean RIBS1 binding density = 1,552 bound RIBS1 molecules per $\mu^2$). Plots (a) and (b) has been symbol gated based on high (o;28% with a mean = 1,136 bound RIBS1 molecules per $\mu^2$) and low (x; 72% with a mean = 213 bound RIBS1 molecules per $\mu^2$) RIBS1 binding density expression on control platelets. Plots (c) and (d) has been symbol gated based on high (o;41% with a mean = 6,412 bound RIBS1 molecules per $\mu^2$) and low (x; 59% with a mean = 584 bound RIBS1 molecules per $\mu^2$) RIBS1 binding density expression on PMA stimulated platelets.

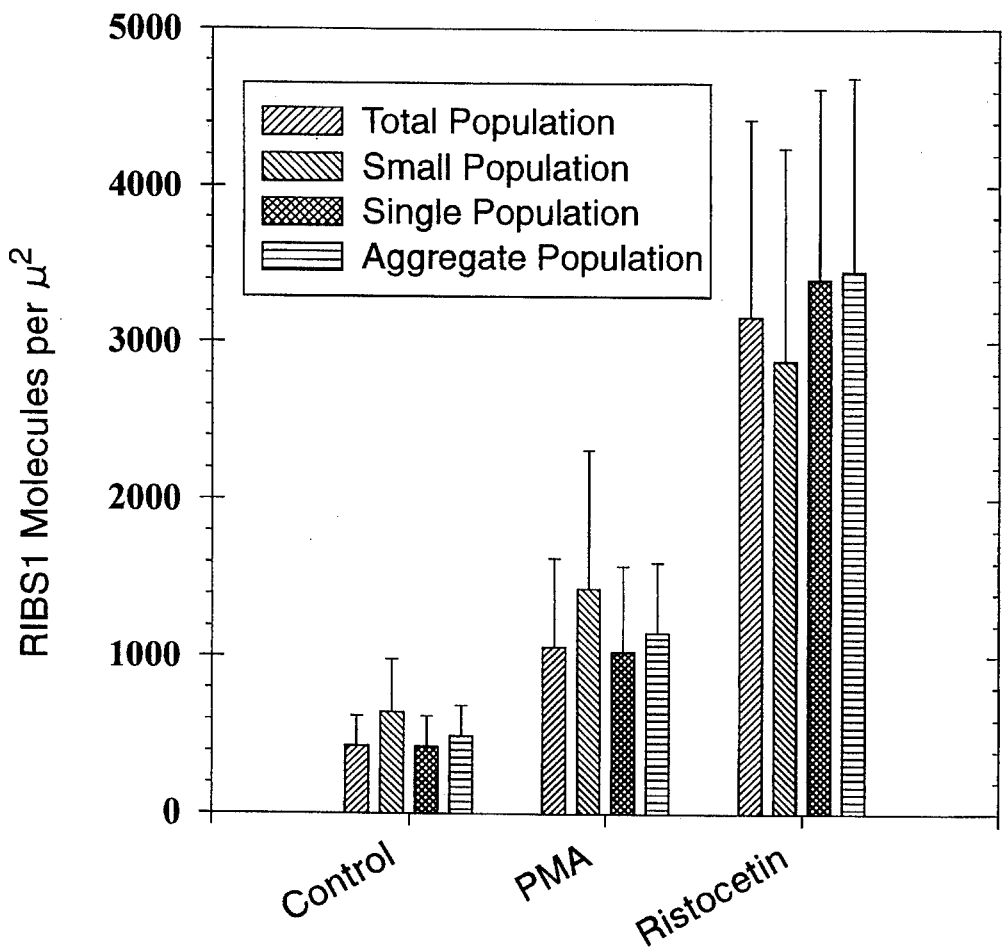

FIG. 16 RIBS1 binding density analysis by platelet size categories for control, 1.0 µM PMA, and 1.5 mg/ml ristocetin stimulated platelet samples. The RIBS1 binding densities of control, PMA, aand ristocetin stimulated platelet sample were all significantly different from each other (two-way ANOVA, p<0.05). The "*" denotes significant difference between a size category and all other size categories within that sample treatment group.

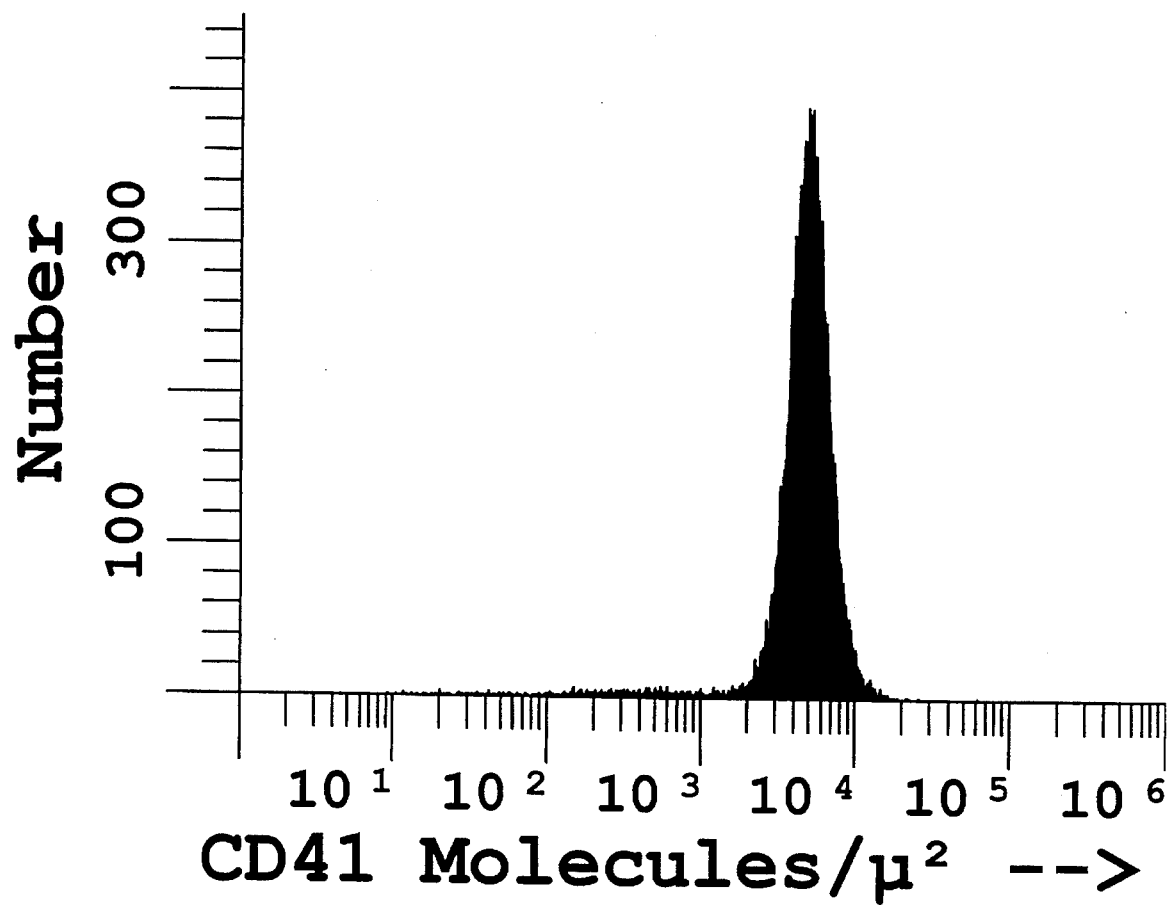
FIG. 17 Typical CD41 binding density distribution for non-activated control platelets analyzed of the FACScan flow cytometer. The mean CD41 binding density for this sample was 4,805 bound CD41 molecules per $\mu^2$. This binding distribution may be interpreted as the GP IIb/IIIa surface receptor concentration, since CD41 is reported to bind to GP IIb/IIIa in a 1:1 ratio.

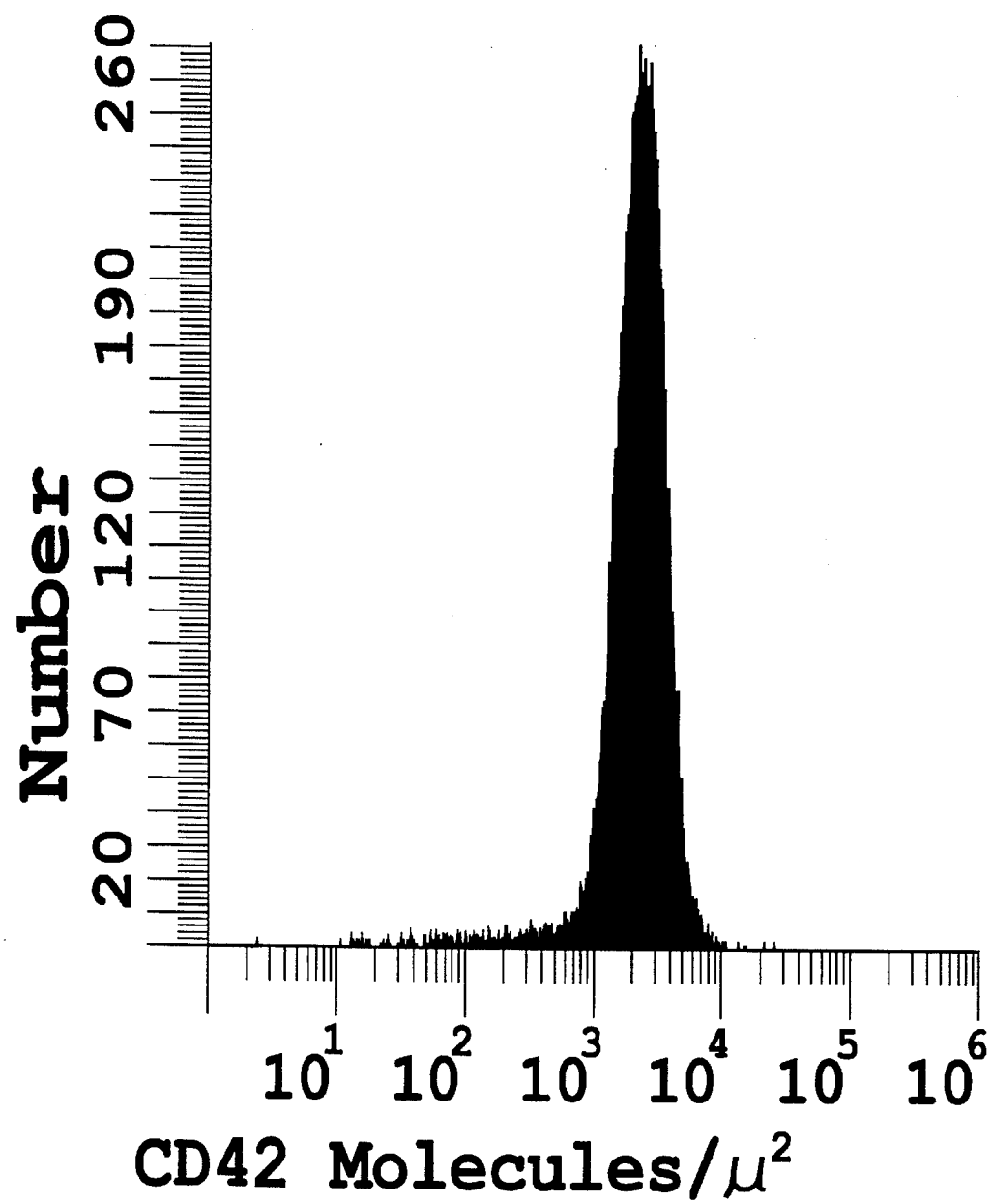
FIG. 18 Typical CD42 binding density distribution for non-activated control platelets analyzed of the FACScan flow cytometer. The mean CD42 binding density for this sample was 2,246 bound CD42 molecules per $\mu^2$. This binding distribution may be interpreted as the GP Ib surface receptor concentration, since CD42 is reported to bind to GP Ib in a 1:1 ratio.

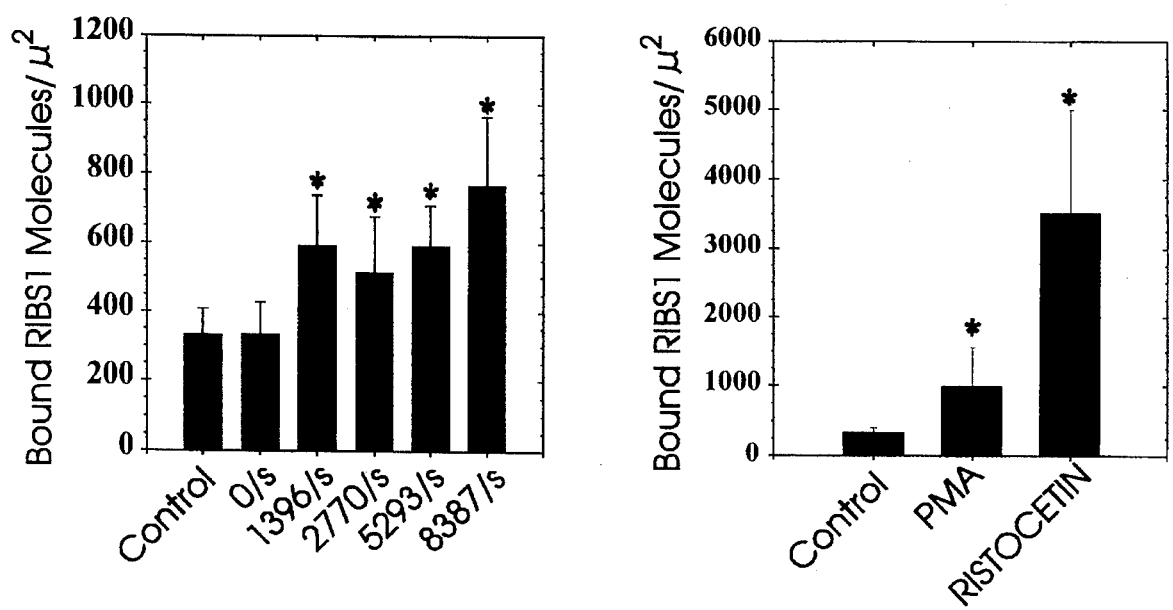

FIG. 19 Comparison of mean RIBS1 binding densities for control, sheared, and chemically stimulated platelet samples (note differences in vertical axis scaling). "*" denotes statistical difference (two-way ANOVA, $p<0.05$) between stimulated and corresponding sample control binding densities ($n=5$ at low shear rates and $n=6$ at high shear rates). Anticoagulant effects were observed in RIBS1 binding density quantitation from use of 0.32% and 0.38% sodium citrate (refer to Table 1). Therefore, the results presented here have been normalized based on the RIBS1 binding densities of control samples. The relative increases above control binding densities illustrate the direct relationship between fibrinogen binding and shear rate exposure. Binding densities resulting from 1.0 µM PMA and 1.5 mg/ml stimulations provide a comparative scale to evaluate shear induced RIBS1 binding densities.

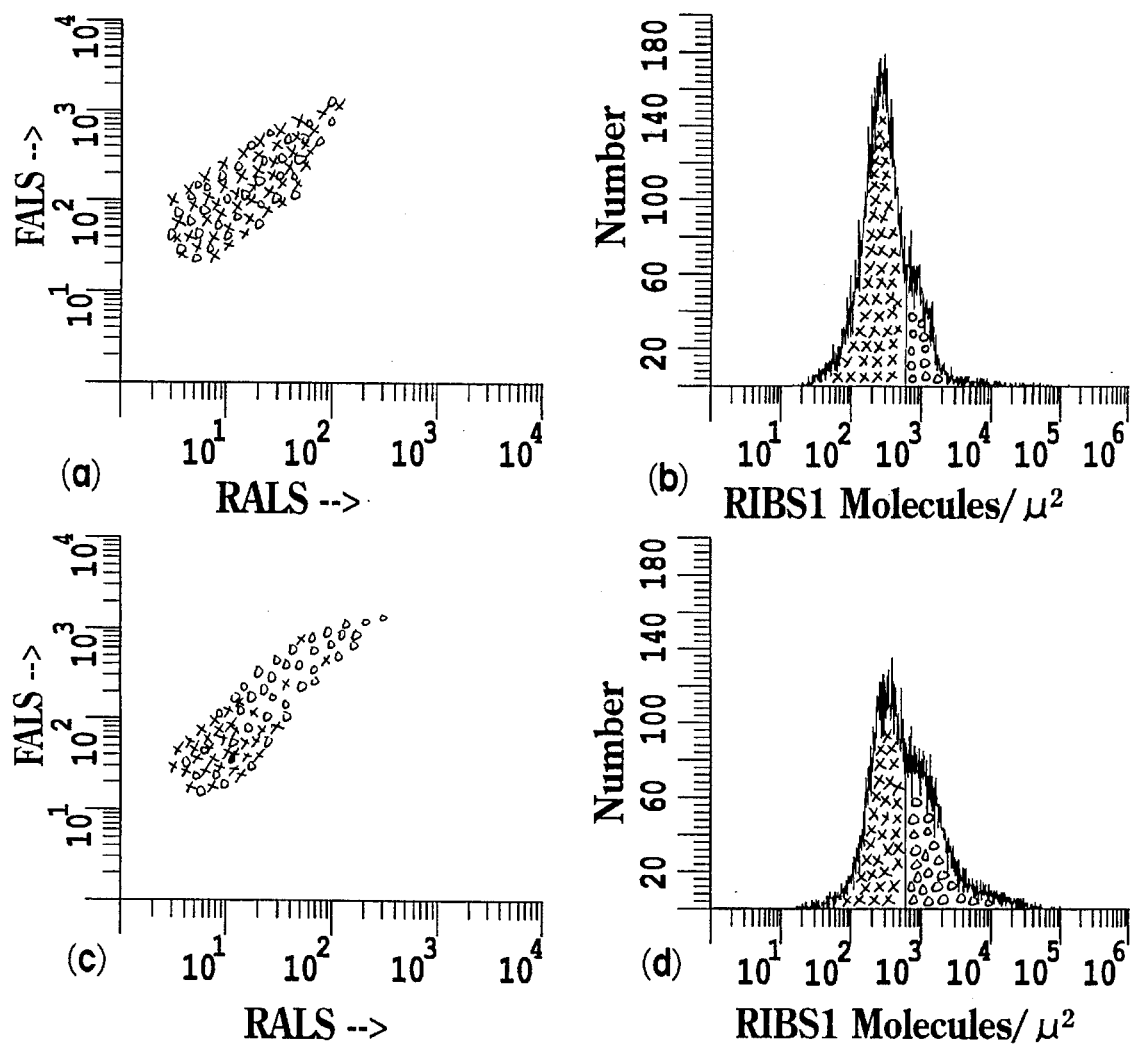

FIG. 20 Typical RIBS1 binding density distributions and corresponding FALS versus RALS profiles analyzed on the FACScan flow cytometer. Plots (a) and (b) are corresponding plots measured from non-activated control platelets (mean RIBS1 binding density = 314 bound RIBS1 molecules per $\mu^2$). Plots (c) and (d) are corresponding plots measured from platelets sheared at 8,387 $s^{-1}$ for 60 seconds (mean RIBS1 binding density = 314 bound RIBS1 molecules per $\mu^2$). Asymmetric binding is illustrated by symbol gating. Plots (a) and (b) has been symbol gated based on high (o;20% with a mean = 1,149 bound RIBS1 molecules per $\mu^2$) and low (x; 80% with a mean = 226 bound RIBS1 molecules per $\mu^2$) RIBS1 binding density expression on control platelets. Plots (c) and (d) has been symbol gated based on high (o;44% with a mean = 1,592 bound RIBS1 molecules per $\mu^2$) and low (x; 56% with a mean = 275 bound RIBS1 molecules per $\mu^2$) RIBS1 binding density expression on platelets sheared a 8,387 $s^{-1}$.

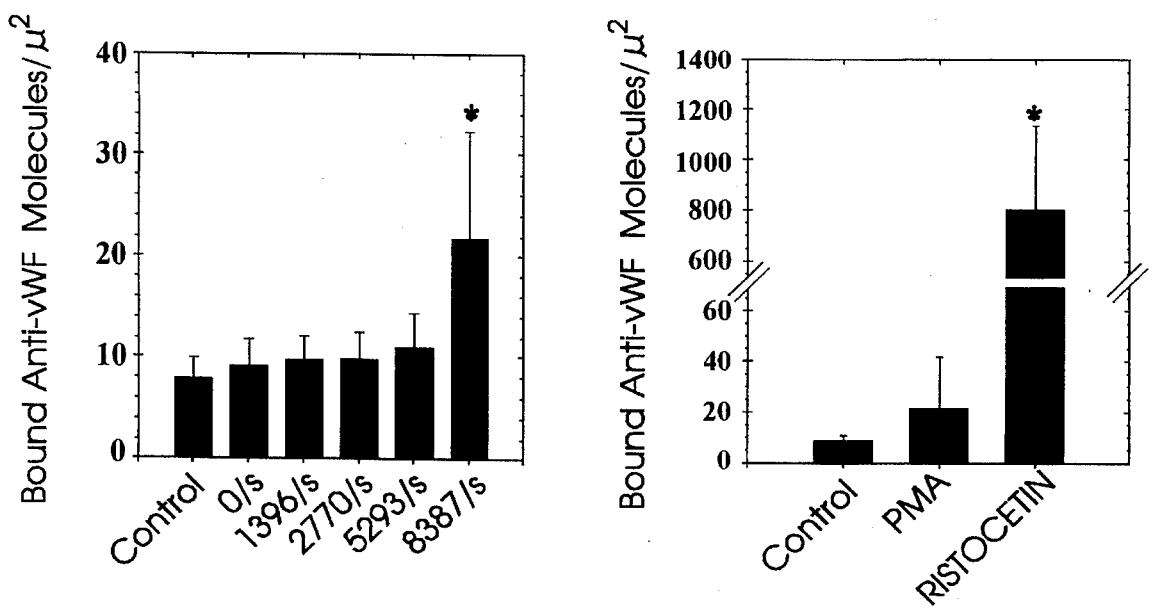

FIG. 21 Comparison of mean Anti-vWF binding densities for control, sheared, and chemically stimulated platelet samples (note differences in vertical axis scaling). "*" denotes statistical difference (two-way ANOVA, p<0.05) between stimulated and corresponding control binding densities. The results represent true sample means ± standard deviation (n=5 at low shear rates and n=6 at high shear rates). No anticoagulant effects were observed with Anti-vWF binding density quantitation. Binding densities resulting from 1.0 μM PMA and 1.5 mg/ml stimulations provide a comparative scale to evaluate shear induced Anti-vWF binding densities.

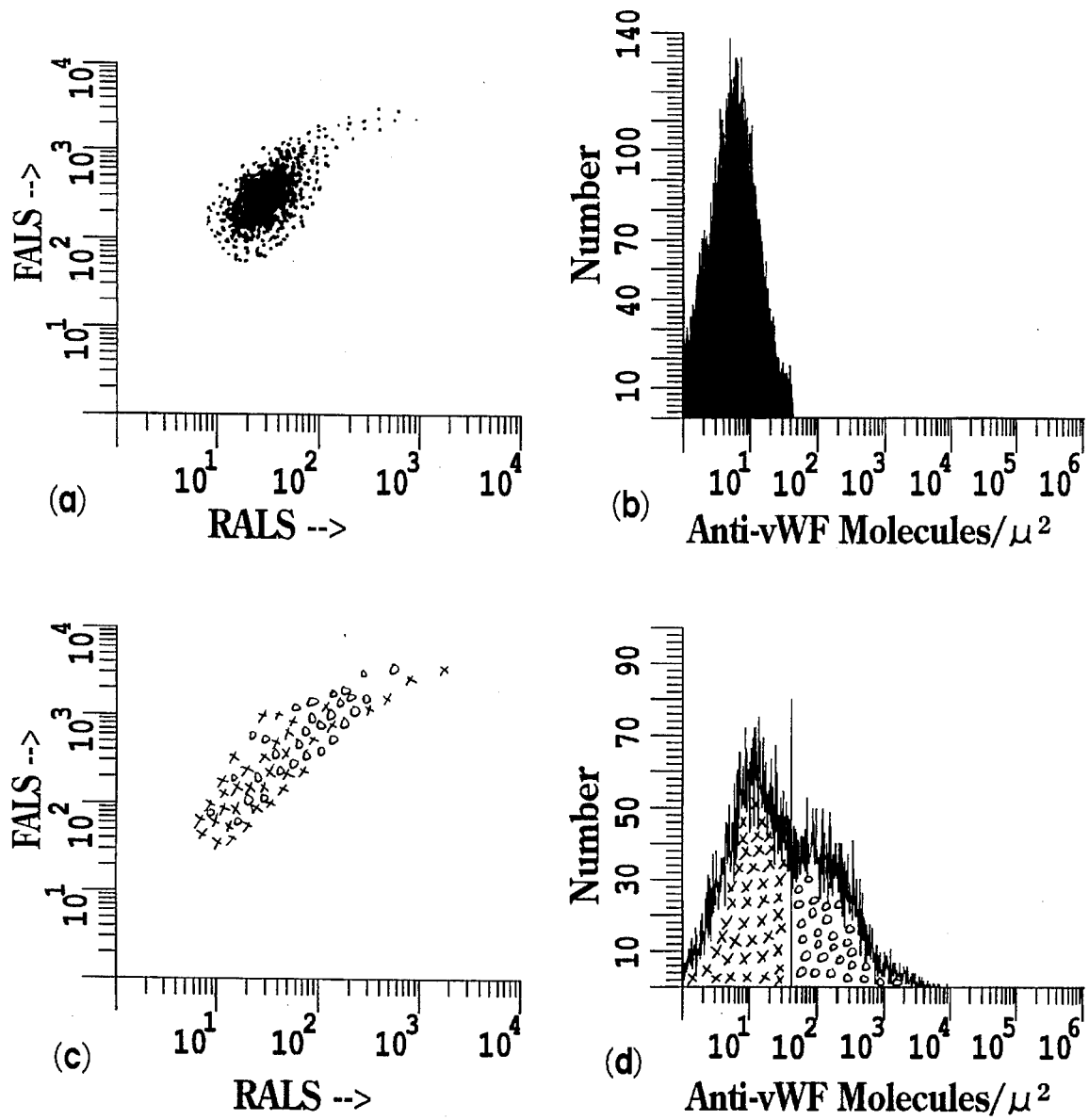

FIG. 22 Typical Anti-vWF binding density distributions and corresponding forward angle light scatter (FALS) versus right angle light scatter (RALS) profiles analyzed on the FACScan flow cytometer. Plots (a) and (b) are corresponding plots measured from non-activated control platelets (mean Anti-vWF binding density = 6.5 bound Anti-vWF molecules per $\mu^2$). Plots (c) and (d) are corresponding plots measured from platelets sheared for 60 seconds at 8,387 $s^{-1}$ (mean Anti-vWF binding density = 31.5 bound Anti-vWF molecules per $\mu^2$). Plots (c) and (d) has been symbol gated based on high (o;39.7% with a mean = 168.5 bound Anti-vWF molecules per $\mu^2$) and low (x; 60.3% with a mean = 10.26 bound Anti-vWF molecules per $\mu^2$) Anti-vWF binding density expression on platelets sheared at 8,387 $s^{-1}$

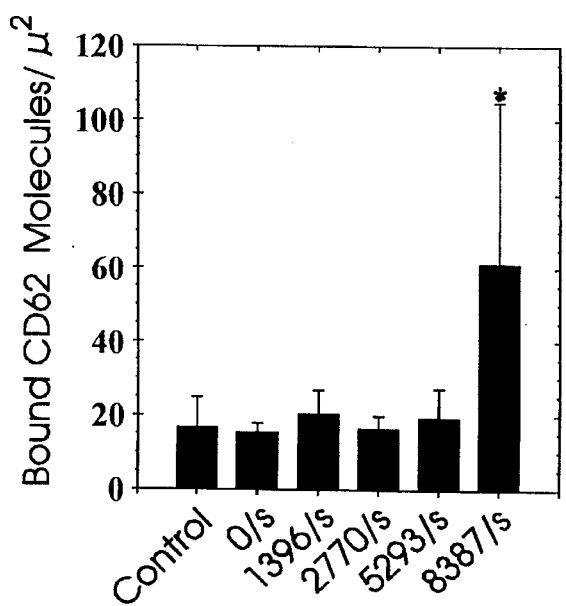
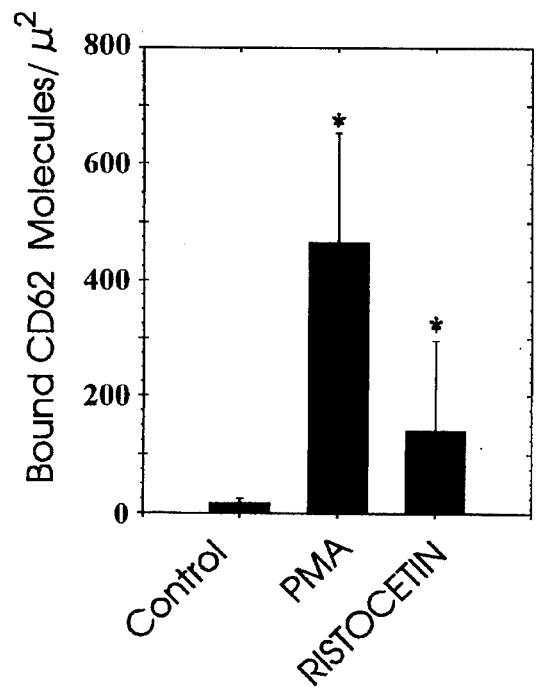

FIG. 23 Comparison of mean CD62 binding densities for control, sheared, and chemically stimulated platelet samples (note differences in vertical axis scaling). "*" denotes statistical difference (two-way ANOVA, p<0.05) between stimulated and corresponding control binding densities. The results represent true sample means ± standard deviation (n=5 at low shear rates and n=6 at high shear rates). No anticoagulant effects were observed with CD62 binding density quantitation. Binding densities resulting from 1.0 µM PMA and 1.5 mg/ml stimulations provide a comparative scale to evaluate shear induced CD62 binding densities.

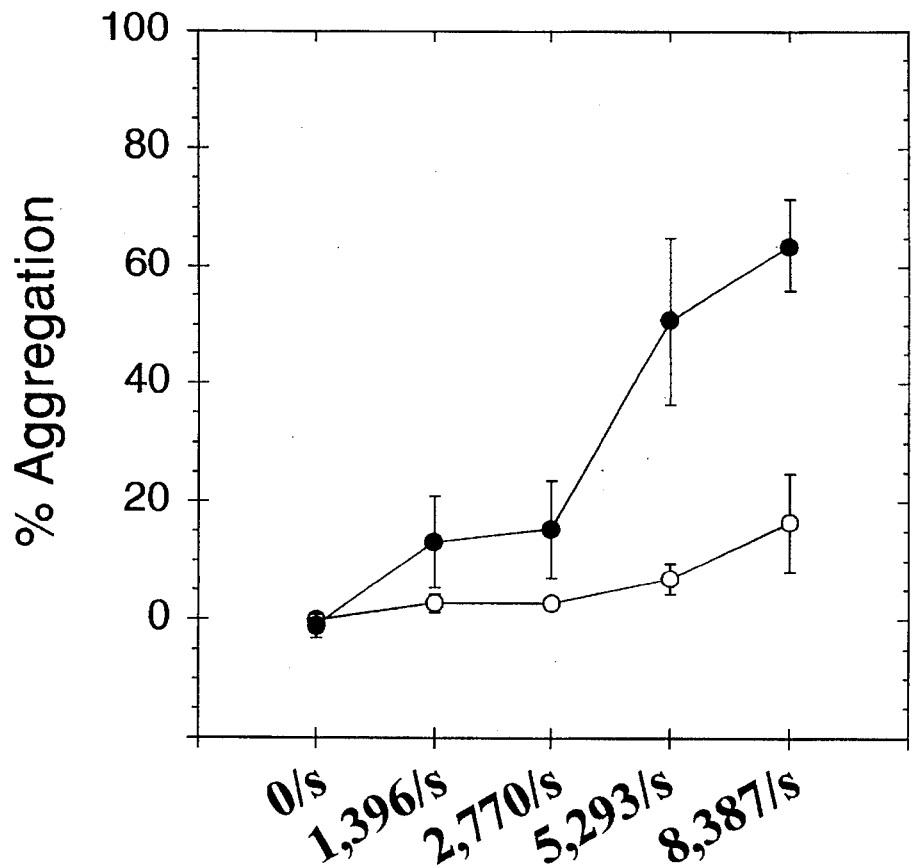
FIG. 24 Sheared induced platelet aggregation curves calculated by % loss of single platelets (●), and by percent loss of single platelet volume (○) (n=5 at low shear rates and n=6 at high shear rates). significant aggregation was measured by both methods at all shear rates. No significant aggregation was detected by either method in surface control samples (0 $s^{-1}$).

METHOD AND APPARATUS FOR DETERMINING ABSOLUTE PARTICLE SIZE, SURFACE AREA AND VOLUME NORMALIZED FLUORESCENCE USING FORWARD ANGLE LIGHT SCATTER INTENSITY IN FLOW CYTOMETRY

BACKGROUND OF THE INVENTION

The present invention relates generally to the optical characterization of biological particles using a flow cytometer. More particularly, the present invention teaches a method and apparatus for the sizing of individual biological particles in a flow cytometer using measured forward angle light scatter and for obtaining a particle fluorescence intensity measurement that is surface area or volume normalized.

It will be appreciated by those skilled in the art that the use of flow cytometric methods in the study of cell populations, surface receptors, and DNA content has greatly enhanced the understanding of many disease states. Patterns in forward and right angle light scatter are routinely used to select subpopulations of cells for further characterization of cell surface and cytoplasmic antigens by fluorescently conjugated probes. Typically, flow cytometric results are reported as the mean fluorescence intensity or mean fluorescence channel of the population being measured. Most published studies equate changes in the fluorescence intensity of a specific cell population with alterations in biological activity.

Fluorescence intensity measurements are unambiguous only if the physical properties of each event are constant. Prior art measurement methods do not take into account the fact that fluorescence intensity measurements are directly related to the size of the particle measured as well as to the surface distribution of the fluorescent probe. Generally, prior art flow cytometry particle characterization methods have not recognized the need to adjust the measured fluorescence for deviations in cell size, whether caused by cell cycle, size abnormalities, activation, aggregation, or other factors.

Much theoretical and practical experimentation was conducted during the 1970's concerning optical characterization of biological cells by classical light scatter techniques. There are three main points which are apparent from review of these studies. First, all studies agree that sizing of biological cells is possible using forward angle light scatter measurements. These studies report accurate sizing in both static and flow systems. Second, the presence of internal structures significantly alters light scatter measured at large scattering angles, but has little to no affect on the angular dependence of light scatter at angles below 10°. Third, the contribution of refracted light is small and only a weak function of size in the forward direction. Fraunhofer diffraction theory has been used as the basis of successful cell sizing.

A particle's size, shape, texture, and internal structures may be characterized by analysis of the intensity and angles through which light is scattered. Much theoretical work has been accomplished describing the mechanism and results of light scatter by small particles. Equations have been developed which relate light scatter to the illumination wavelength, refractive index, angle of scatter, and particle size. Mie theory, Fraunhofer diffraction theory, photon correlation spectroscopy, turbidity spectra, and Rayleigh Debye regimes can accurately predict light scattered from small particles within a specified range of conditions.

Light scatter can be divided into three distinct categories: diffraction, refraction, and reflection. Forward angle light scatter (FALS), as measured in a flow cytometer, is composed primarily of diffracted light, while right angle light scatter (RALS) is composed of significant proportions of all light scatter components. Diffracted light collected within small forward angles is rich in particle size information. Since very little refracted light is collected in the FALS detector, internal structures do not influence the FALS measurement unless the particle and its internal structures are very large and well defined. Particle shape, orientation, and degree of well defined internal structures influence refracted and reflected light scatter primarily through large angles, as can be seen in RALS flow cytometer measurements. The use of RALS to distinguish cell populations based on internal structures has been successfully described in the past.

While FALS is generally considered to be a rough measure of cell size, the full capacity of forward angle light scatter in flow cytometry has not been realized. Implementation of a theoretical model for diffracted light provides valuable particle size information from the flow cytometer. Fraunhofer diffraction theory (FDT) accurately predicts diffracted light scatter in the particle size range from 0.1 to 700 microns in diameter, depending on the illuminating wavelength and the angle of collection. FDT is of particular value for cellular studies using flow cytometers due to its simplicity and the cell-size particle range it describes.

Flow cytometry allows detection of molecular level changes which occur on the surface of individual biological cells based on the binding of fluorescent probes. Interpretation of flow cytometric data describing such changes, such as would occur in platelet activation, is complicated since the fluorescence intensity measurements are directly related to the particle size, as well as the surface distribution of bound fluorescent probes. Prior art optical techniques allow an estimate of the particle size distribution, but do not provide individual particle sizes. Resistive techniques do provide individual particle sizes, but do not have the capability to measure single particle fluorescence. Size complications necessitate the development of a new quantitative flow cytometric technique which decouples particle fluorescence and particle size.

Thus, there is a need for a method of accurately determining particle radius from forward angle light scatter measured in a flow cytometer. Further, a quantitative flow cytometric method based on surface area or volume normalization is lacking in the prior art. Such a method, uniquely provided by optical sizing, would allow quantitation of fluorescent probe binding independent of particle size.

SUMMARY OF THE INVENTION

The method of the present invention is based on the concept that surface area and volume normalized fluorescence (SANF) and volume normalized fluorescence (VNF) are particle characteristics which contain unique information. The only method of obtaining SANF/VNF is to measure both the fluorescence and the particle size of each particle in a population. Current flow cytometry practice measures the individual particle fluorescence but not the size. Thus, the present method permits calculation of single particle size from light scatter intensity which permits calculation of the SANF and/or the VNF.

The present invention also teaches that surface area normalized fluorescence (SANF) or volume normalized fluorescence (VNF) is useful as a diagnostic parameter.

SANF is important for fluorescent probes which bind to membrane sites (for example, CD62 binding to surface expressed GMP-140, an alpha granule membrane protein expressed on the plasma membrane only following alpha granule release). VNF is important for fluorescent probes which bind to intracellular sites (acridine orange binding to DNA, for example).

Accordingly, in the method of the present invention, to compute SANF and/or VNF, the size of each particle is associated with the measured fluorescence.

SANF and VNF can be used as a post-measurement parameter to provide additional information about particle condition and can be installed in flow cytometry software for normalization of data sets acquired on any flow cytometer.

Application of an empirically determined predictive equation based on light scatter theory allows rapid calculation of SANF and/or VNF. Such equation can be installed in flow cytometry hardware to provide the calculational speed required for real-time analysis (gating) and/or particle sorting. Also, coupling of SANF and/or VNF with specific calibration techniques permits absolute quantitation of the fluorescence intensity. The invention also provides a universal calibration method which permits comparison of results among different operators and/or flow cytometry hardware, i.e., an absolute measurement which is not subject to interpretation. The method is particularly useful in measuring very small biological particles such as liposomes.

BRIEF DESCRIPTION OF THE DRAWINGS

FIG. 2 is a plot of a typical diffraction pattern intensity predicted using Fraunhofer Diffraction Theory for a spherical particle having a radius of 5 microns and an illumination wavelength of 488 nanometers.

FIG. 3 is a plot of particle radius versus FALS intensity measured on a Becton-Dickonson FACScan flow cytometer, after least square analysis of measured data to obtain best to fit values.

FIG. 4 is a plot of particle radius versus FALS intensity, with curve fitting limited to FALS values less than 3,700 arbitrary intensity units.

FIG. 5 is a plot of particle sized distribution measured on the Becton-Dickonson FACScan for fixed resting platelets.

FIG. 6 is a plot of the sized distribution of fixed lymphocytes measured optically on the FACScan flow cytometer.

FIG. 7 is a graphical comparison of the size distributions of normal control platelets measured on an electronic particle counter and as calculated from the flow cytometer forward light scattering intensity measurements using the method of the present invention.

FIG. 8 is a graphical comparison of CD41-FITC binding to platelet GP IIb/IIIa before and after platelet activation.

FIG. 9 is a comparison of CD62 binding to platelet GMP-140 before and after and platelet activation.

FIG. 10 is a graphical representation of CD62 binding distributions after surface area normalization.

FIG. 11 is a graphical comparison of CD41, CD42, CD62, and MSIgG binding by particle size with and without surface area normalization.

FIG. 12 is a plot of CD42 binding intensity distribution for non-activated control platelets.

FIG. 13 are plots of typical Anti-vWF binding density distributions and corresponding forward angle light scatter versus right angle light scatter profile.

FIG. 14 is a graphical analysis of Anti-vWF binding density by platelet size categories.

FIG. 15 contains typical RIBS1 binding density distributions and corresponding FALS versus RALS profiles as analyzed on the flow cytometer.

FIG. 16 is a graphical representation of a binding intensity analysis by platelet size categories.

FIG. 17 is a graphical representation of typical CD41 binding density distribution for nonactivated control platelets analyzed in the FACScan flow cytometer.

FIG. 18 is a graphical representation of typical CD42 binding density distribution for nonactivated control platelets analyzed in a FACScan flow cytometer.

FIG. 19 is a comparison of mean RIBS1 binding densities for control, sheared, and chemically stimulated platelet samples.

FIG. 20 is a graphical representation of typical RIBS1 binding density distributions and corresponding FALS versus RALS profiles.

FIG. 21 is a graphical comparison of mean Anti-vWF binding densities for control, sheared, and chemically stimulated platelet samples.

FIG. 22 contains graphical representations of typical Anti-vWF binding density distributions and corresponding forward angle light scatter versus right angle light scatter profiles.

FIG. 23 is a graphical comparison of mean CD62 binding densities for control, sheared, and chemically stimulated platelet samples.

FIG. 24 graphically represents shear induced platelet aggregation curves calculated by percentage loss of single platelets and by percent loss of single platelet volume.

DESCRIPTION OF THE PREFERRED EMBODIMENT

Figure 1:
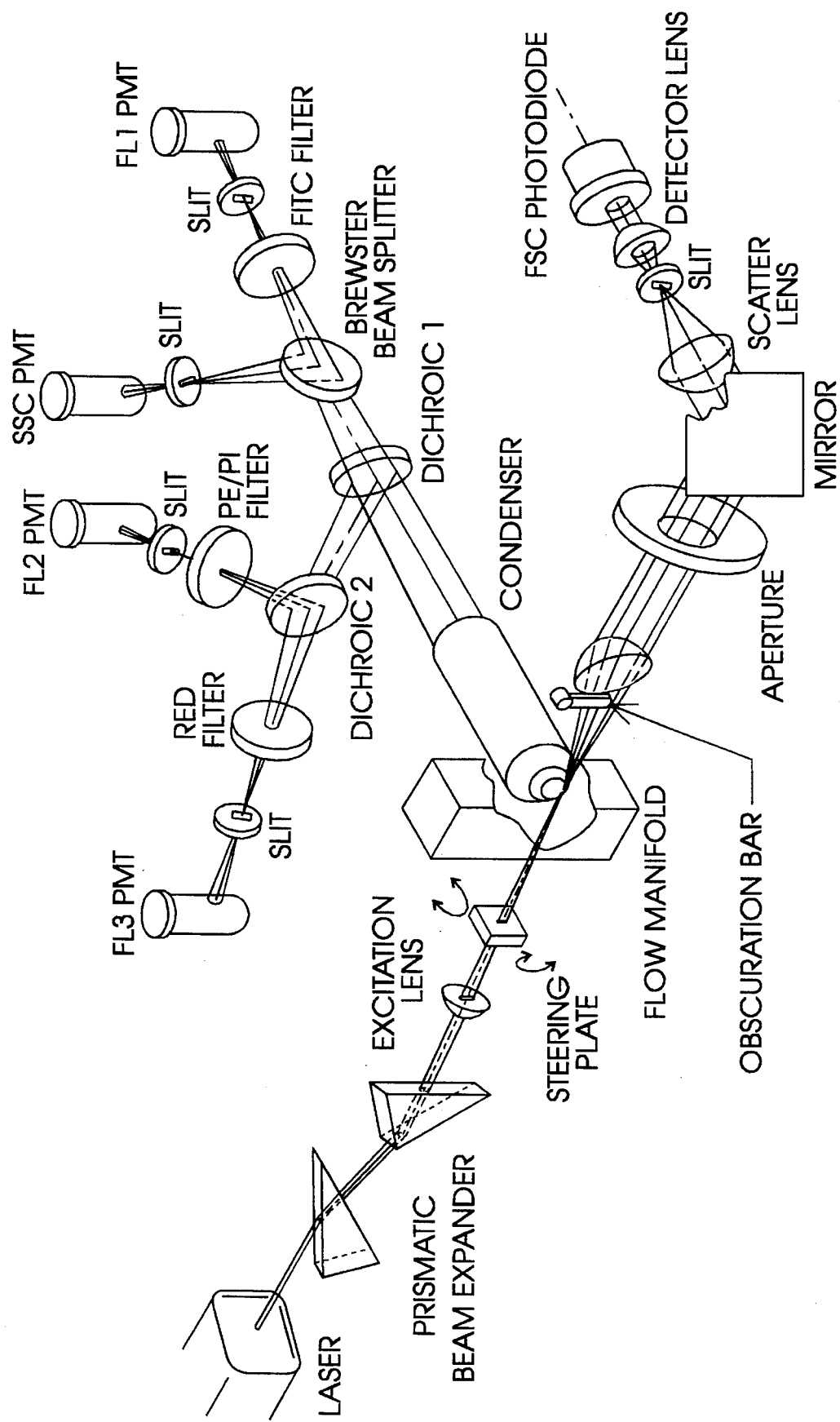
FIG. 1 is a schematic representation showing the arrangement of the various optical elements in a conventional flow cytometer, and specifically the Becton-Dickenson FACScan.
Figure 25:
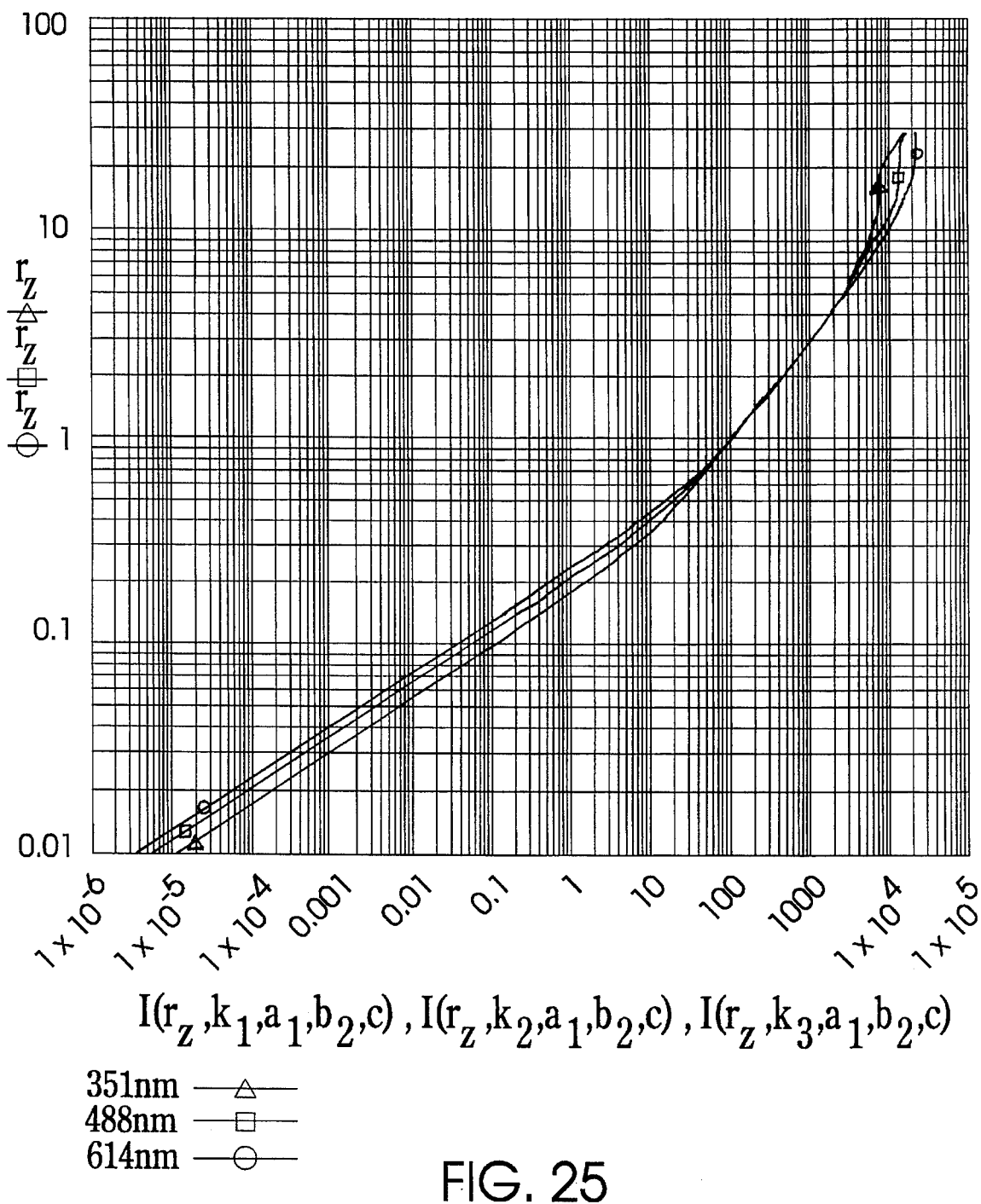
FIG. 25 is a graphical representation of the theoretical size of a particle versus the size predicted by Fraunhofer Diffraction Theory and forward angle light scatter with a minimum scatter angle of 0.5° and a maximum scatter angle of 20.0°.
Figure 26:
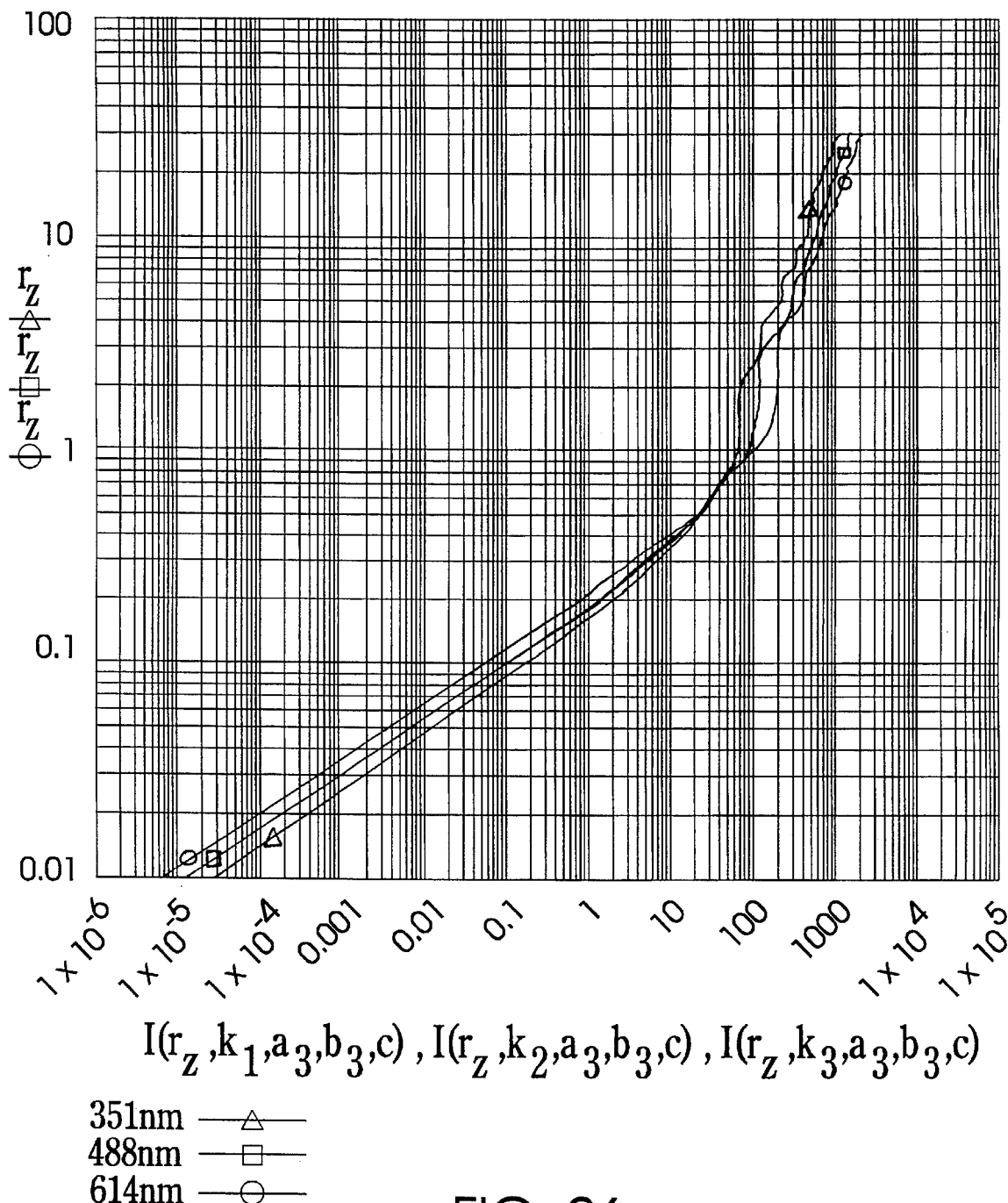
FIG. 26 is a graphical representation of the theoretical size of a particle versus the size predicted by Fraunhofer Diffraction Theory and forward angle light scatter with a minimum scatter angle of 5.0° and a maximum scatter angle of 30.0°.
Figure 27:
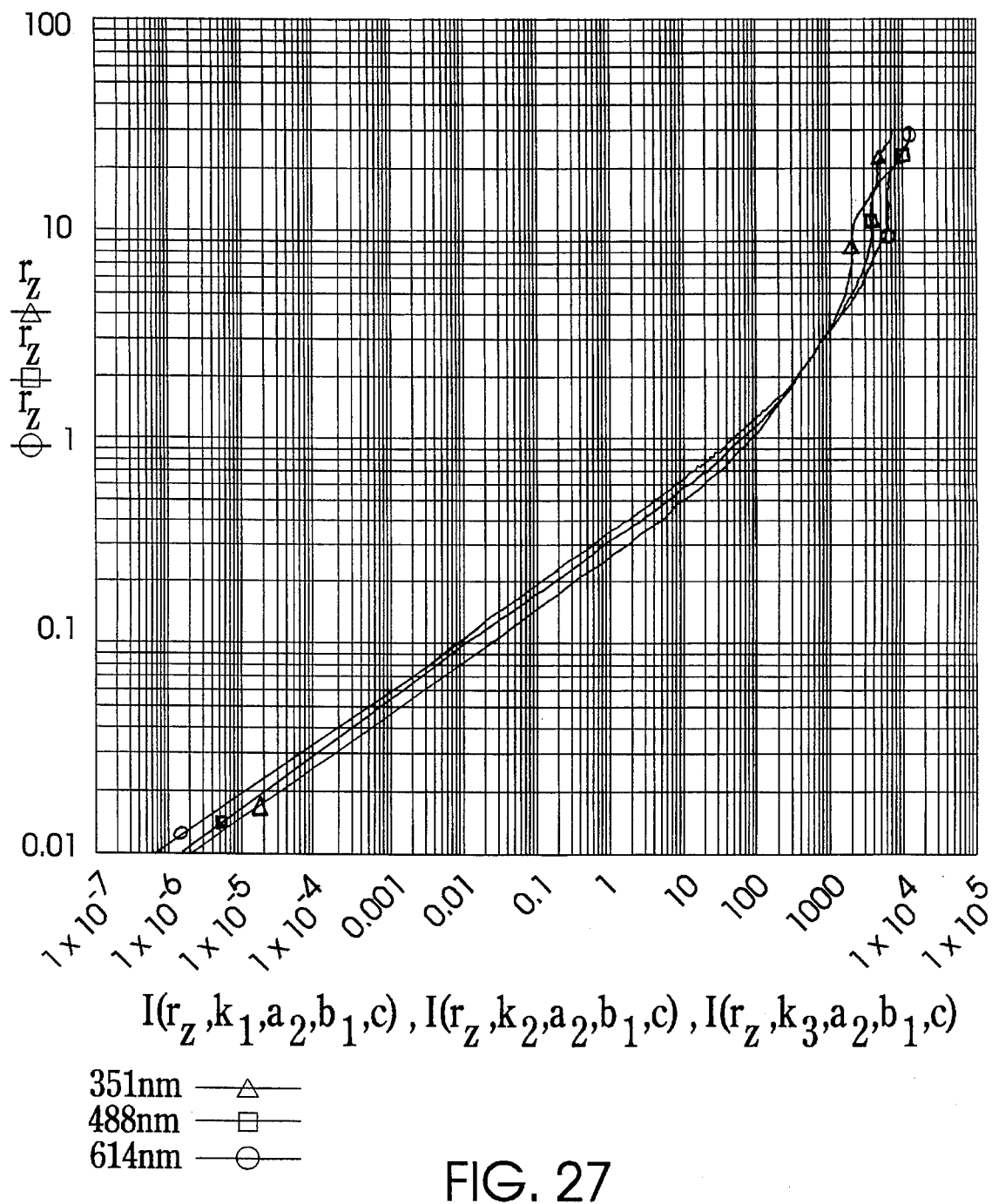
FIG. 27 is a graphical representation of the theoretical size of a particle versus the size predicted by Fraunhofer Diffraction Theory and forward angle light scatter with a minimum scatter angle of 0.964° and a maximum scatter angle of 8.257°.
Figure 28:
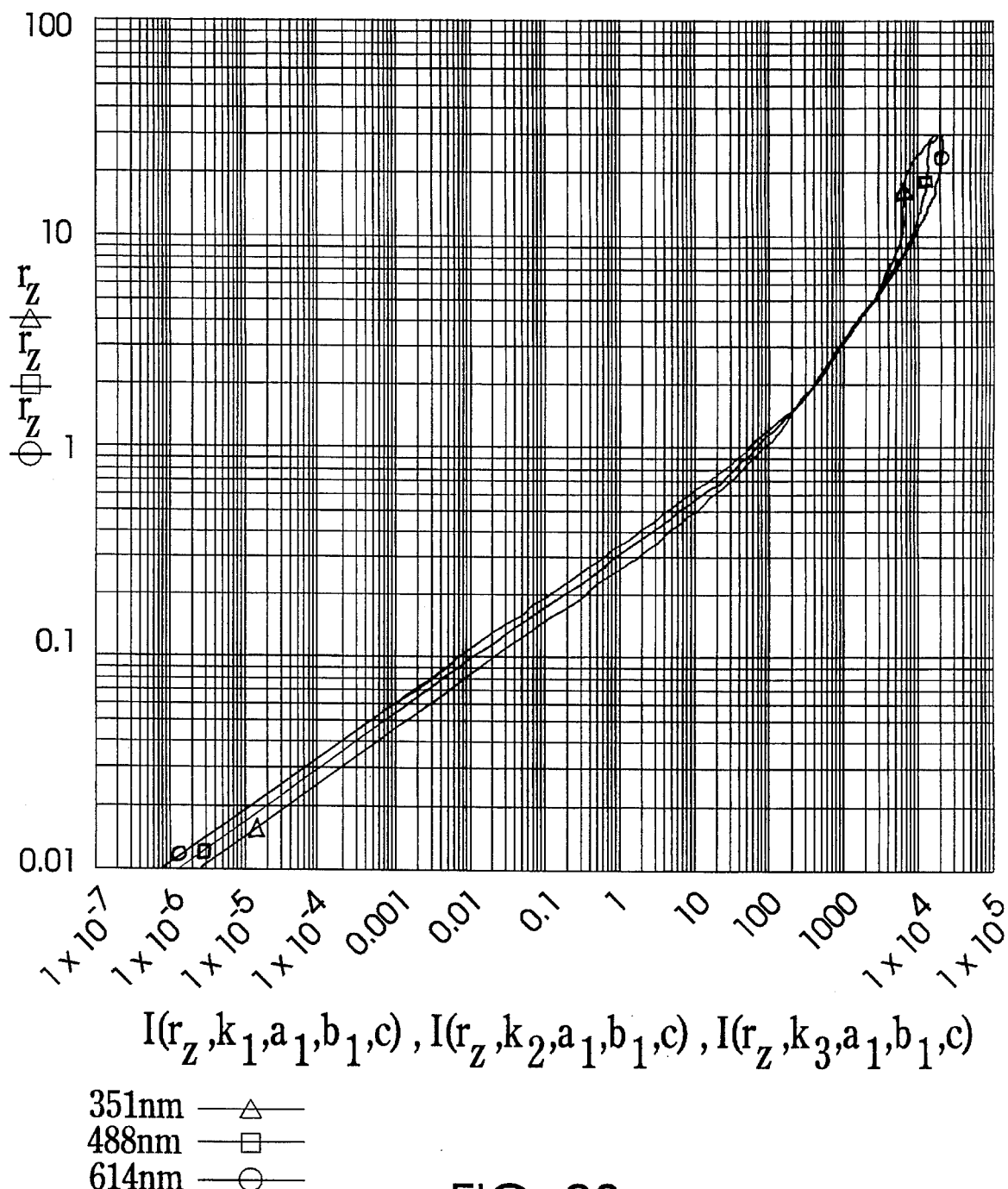
FIG. 28 is a graphical representation of the theoretical size of a particle versus the size predicted by Fraunhofer Diffraction Theory and forward angle light scatter with a minimum scatter angle of 0.500° and a maximum scatter angle of 8.257°.

In accordance with the objects of the invention, an empirical equation, which calculates particle radius as a function of forward angle light scatter intensity measured in a conventional flow cytometer, is generated using Fraunhofer Diffraction Theory. The Becton-Dickonson FACScan flow cytometer, which was used in implementing one embodiment of the invention, has an effective range for accurate, optical particle radii measurement from 0.33 µm to 9.03 µm when using this semi-empirical relationship. The radii of polystyrene microspheres were optically measured with an average percent difference of 2.1% compared to the radii measured using a standard electronic particle counter. Optical sizing of platelets and lymphocytes fixed with 1% paraformaldehyde resulted in mean cellular radii which were slightly larger than corresponding measurements obtained with the electronic particle counter.

The mathematical approach described here for the development of the sizing equation for use with the FACScan may be used to develop similar equations for use with other flow cytometers and thus has universal application in flow cytometry using light angle scattering.

Materials and Methods

Flow Cytometry

All samples were analyzed in a Becton-Dickinson FACScan flow cytometer. The FACScan was formatted for two-color analysis with the light scatter and fluorescence channels set at logarithmic gain using 1024 channels and a four decade scale. The FACScan used a 15 milliwatt air cooled laser producing a single line excitation output at 488 nm. Listmode data was acquired using LYSIS II software running on a Hewlett-Packard Model 340 computer. Light scatter and fluorescence channels were standardized each day using QC3 841 beads (Flow Cytometry Standards Corporation, Research Triangle Park, N.C.), a dual-color reference standard of known size and fluorescence. Amplifier settings were adjusted for optimal measurement sensitivity and reproducibility.

Data analysis was performed using WINLIST (Verity Software House, Inc., Topsham, Me.) installed on a 33 MHz 80486DX based microcomputer. The program allows equations to be entered and used as calculated parameters during data analysis. Forward angle light scatter conversion to particle size measurements was accomplished using the calculated parameter capability of WINLIST software.

Size Calibration Spheres

Calibration spheres of various sizes were used to establish the forward angle light scatter sizing parameters for the flow cytometer. Polystyrene calibration spheres ranging from 0.8 µm to 47 µm in diameter were purchased from Particle Data Inc. (Elmhurst, Ill.) and Polyscience Inc. (Warrington, Pa.). Calibration spheres suspended in isotonic saline were measured with an Elzone PC-285 electronic particle counter (Particle Data, Inc.) to confirm the size distribution reported by the manufacturer.

Mathematical Approach to Optical Sizing

The forward angle light scatter (FALS) measured on a flow cytometer is the summation of all modes of light scatter (diffraction, refraction, and reflection). Refraction and reflection contribute only a small fraction of the total measured FALS. Refraction and reflection intensities depend greatly upon the angle of incidence and the refractive index of the medium and the particle. Refracted light scatter measured at small angles yields little information about particle size, but may influence FALS measured for particles with large, well defined internal structures. Forward angle light scatter, as measured in a flow cytometer, is composed primarily of diffracted light.

A preferred embodiment of the method of the present invention relies on Fraunhofer diffraction theory (FDT) to provide an appropriate theoretical treatment for the particle sizes of interest and the available flow cytometer optical arrangement. FDT requires the particle size to be large compared to the illumination wavelength. Particles as small as 0.1 µm in diameter up to 700 µm in diameter can be characterized using FDT depending upon the illumination wavelength used and the discrete angles of scattered light collection. The optical arrangement of the FACScan determines the fixed angles over which forward angle light scatter is collected (FIG. 1). The output intensity and focused spot size of the laser affect the intensity per surface area illuminating the particle.

The diameter of the diffraction pattern intensity distribution is inversely proportional to the particle radius for spherical particles. The intensity distribution of the Fraunhofer diffraction pattern is predicted by Equation 1, the Airy formula.

$$I(w) = \frac{C \cdot r^2}{w^2} \cdot [J_1(krw)]^2 \qquad \text{Equation 1}$$

where:

C=flux per unit area of the incident beam r=particle radius w=sin θ=s/f s=radial distance defining a point on the focal plane f=focal length of the lens k=2π/λ

λ=wavelength of the incident beam $J_1$=first order Bessel's Function of the first kind FIG. 2 illustrates the shape of a typical curve for the diffracted light scatter intensity measured at discrete angles of collection in a conventional flow cytometer such as that shown in FIG. 1. Forward angle light scatter intensity measured on a flow cytometer is the integrated area under the intensity versus collection angle curve, shown as the shaded area in FIG. 2, integrated again over 360° angle of revolution in the focal plane. Double integration of Equation 1 yields Equation 2, the classical representation of the $$L_{s_1,s_2} = \int_0^{2\pi} \int_{w_1}^{w_2} I(w)\,dw\,d\phi \qquad \text{Equation 2}$$

$$L_{s_1,s_2} = E[J_0^2(krs_1/f) + J_1^2(krs_1/f) - J_0^2(krs_2/f) - J_1^2(krs_2/f)]$$

where:

$L_{s_1,s_2}$=total measured scattered light intensity collected between radii $s_1$ and $s_2$ as measured at the focal plane $J_0$=zero order Bessel's Function of the first kind $E = CN\pi r^2$ N=number of particles producing scatter $s_i$=minimum (i=1) and maximum (i=2) radii of the diffraction pattern measured at the focal plane Fraunhofer diffraction theory equation.

Equation 2 predicts the total diffracted light energy produced by a particle of radius r measured within any ring(s) on the focal plane bound by radii $s_1$ and $s_2$. The parameter s/f can be replaced by sin(θ$_i$), where θ$_1$ is the minimum angle and θ$_2$ is the maximum angle through which the scattered light is collected relative to the incident beam. The optical arrangement of the forward angle light scatter detection system installed in the FACScan as shown in FIG. 1 incorporates a fixed position obscuration bar to block nonscattered laser light, condensing lenses, and a fixed aperture (FIG. 1). The physical arrangement of the optical elements determines the limiting angles, $\theta_{min}$ and $\theta_{max}$, over which the forward scattered light intensity (FALS) is measured. Equation 2 may be rewritten for forward scattered light intensity, FALS(r), as a function of the particle radius and the limiting angles as shown in Equation 3.

$$FALS(r) = \pi Cr^2[J_0^2(kr\sin\theta_{min}) + J_1^2(kr\sin\theta_{min}) - J_0^2(kr\sin\theta_{max}) - J_1^2(kr\sin\theta_{max})]$$ Equation 3

The forward scatter detection system in the FACScan reportedly collects light from a minimum angle less than 1 degree to a maximum angle of 10 degrees (B-D FACScan Manual). The precise angles depend upon position of the obscuration bar and lenses. The intensity per unit area of the incident beam depends on the laser output and focused spot size measured at the flow chamber. The number of particles (N) producing the scatter is assumed to be one.

The ideal equation would calculate the particle radius as a function of the measured forward scattered light intensity and angle of collection. Formulation of such an explicit equation is not possible by simple rearrangement of the equation for FDT. Bessel's function terms are represented by infinite series expansions which are not invertible. Simplification of the infinite series is not possible if accuracy is to be maintained for the entire range of particle sizes of interest. An iterative computer program with stringent convergence criteria could be used to solve Equation 3 for particle radius given the measured FALS(r), C, $\theta_{min}$ and $\theta_{max}$. However, this is not practical because the program must iteratively solve Equation 3 for each event collected. Such a computationally intensive process would be impractical, especially for data files containing 10,000 or more total events. Consequently, in the present method, equation 3 is used as the basis to derive an empirical equation relating the particle radius to FALS.

The FACScan's sizing characteristics were determined by measurement of FALS for multiple samples of monodisperse polystyrene calibration beads suspended in isotonic saline. Though the refractive index of polystyrene beads and biological cells are different, the use of polystyrene beads provides the basis to determine the optical parameters of the FACScan. Ten thousand microspheres of each size were counted in the FACScan and the mean FALS was calculated for each sample. Microspheres with mean diameters ranging from 0.86 µm to 32.98 µm were characterized. The majority of size calibration spheres used were within the particle size range of interest, 0.8 µm to 20 µm in diameter. Size calibration spheres of this size were chosen in order to increase the statistical predictive value of the fitted parameters and resulting equations. Mathcad, a mathematical software package (Mathsoft Inc., Cambridge, Mass.), was used to solve Equation 3 and determine, by method of least squares, the best fit values for C, $\theta_{min}$, and $\theta_{max}$ by comparing calculated FALS to measured FALS. Once the optical parameters were determined, a computer program such as Mathcad, is used to generate the unique theoretical FALS(r) values from Equation 3 for a range of particle radii from 0.1 µm to 35 µm using steps of 0.1 µm in radius. A fitted polynomial equation is then determined for the generated theoretical data points calculated from Equation 3.

Results

Empirical Sizing Equation

The FALS of monodisperse suspensions of polystyrene microspheres were measured on the FACScan as described in the previous section. Table 1 indicates the mean particle radii measured in the Elzone electronic particle counter and the corresponding mean FALS measured on the FACScan. Least squares analysis of the measured data yielded the following best fit values for C, $\theta_{min}$, and $\theta_{max}$: C=39.06 arbitrary intensity units per $\mu^2$, $\theta_{min}$=0.95°, and $\theta_{max}$=8.6°. The best fit curve ($R^2$=0.9995) is shown in FIG. 3.

TABLE 1

Polystyrene Microspheres Used to Determine FACScan Optical Parameters

| Elzone Particle Counter Mean Radius <µm> | FACScan Flow Cytometer Mean FALS <a.i.u.> |
|---|---|
| 0.43 | 3.93 |
| 0.68 | 20.20 |
| 0.99 | 69.82 |
| 1.97 | 384.67 |
| 4.49 | 1775.19 |
| 7.69 | 3367.01 |
| 9.60 | 3743.07 |
| 10.55 | 3512.71 |
| 13.87 | 4008.69 |
| 16.49 | 5051.38 |

Particle radius data represents the mean particle radius of monodisperse suspensions of polystyrene size calibration microspheres prepared in isotonic saline solution. For electronic particle sizing, 10,000 to 25,000 particles were characterized on the Elzone. The FALS data represents the histogram mean of between 5,000 and 10,000 particles measured on the FACScan flow cytometer.

Using the best fit values of C, $\theta_{min}$, and $\theta_{max}$, Equation 3 was numerically solved, using Mathcad, for particle radii ranging from 0.1 µm to 32.5 µm in steps of 0.1 µm. This process generated 350 FDT-predicted, integrated FALS values, unique for the FACScan, as a function of illuminated particle radius. These predicted (FALS,r) pairs are discrete solutions of FDT for specified particle radii over the entire FALS range of our FACScan. Estimation of particle radius from the corresponding measured FALS can be performed by direct interpolation between (FALS,r) pairs. Alternatively, an empirical equation can be fitted to the 350 (FALS, r) pairs to approximate a continuous function for particle radius as a function of measured FALS, effectively inverting Equation 3.

Analysis of the measured and theoretical data shows that a major inflection with anomalous behavior occurred between the FALS range of 3700 a.i.u. to 3777 a.i.u., corresponding to particle radii of 9.03 µm to 13.61 µm respectively. Within this FALS range, a single measured value of FALS could correspond to as many as three distinctly different particle radii. Another such anomalous region is predicted to occur between the FALS range of 8400 a.i.u to 8489 a.i.u., corresponding to particle radii of 23.52 µm to 28.20 µm respectively. Due to this anomalous behavior, no single particle radius can be predicted for measured FALS in these regions. The use of classical light scatter theory to right angle light scatter (RALS) measurement may increase accuracy of particle sizing and allow a means to determine the particle radius with in anomalous regions in the FALS measurements. RALS would not be used to size directly but to indicate size relative to another cytometric event.

A fifth order polynomial equation was successfully fit ($R^2$=0.9998) to the theoretical data when curve fitting was limited to FALS values less than 3700 a.i.u. (FIG. 4). A comparison of FDT predicted particle radius with curve fitted polynomial equation derived in accordance with the method of the present invention is shown in FIG. 4. FALS values of 1 a.i.u. and 3700 a.i.u. theoretically correspond to a spherical particle radii of 0.33 μm and 9.03 μm (0.66 μm and 18.06 μm in diameter). The fitted polynomial equation is given in Equation 4, where x is the measured FALS. The 7 fitted constants are mathematically and statistically valid since curve fitting was performed using 90 discrete (FALS,r) pairs covering the particle radius range from 0.1 μm to 9.0 μm.

$$r = -0.387 + 0.725 \cdot x^{0.101} + 3.60e-3 \cdot x - 2.69e-6 \cdot x^2 + 1.67e-9 \cdot x^3 - 5.00e-13 \cdot x^4 + 5.77e-17 \cdot x^5$$

Equation 4

Optical Sizing

The original polystyrene microspheres and a set of previously unused calibration microspheres were sized on both the electronic particle counter and the FACScan. The electronically and optically determined radii of these polystyrene calibration spheres are presented in Table 2. The average percent difference between the radii measured optically on the FACScan and the radii measured on the electronic particle counter is 2.1%.

Human platelets and isolated human lymphocytes were obtained, fixed with 1% paraformaldehyde, and analyzed separately on the FACScan to assess optical sizing performance with biological particles. Human platelets were fluorescently labeled with fluorocein isothiocynate (FITC) using Anti-CD42b-FITC (GenTrak, Inc., Plymouth Meeting, PA: 2.5 μl/2×10⁶ platelets). Human lymphocytes were also fluorescently labeled using Anti-CD4-FITC (GenTrak, Inc.: 2.5 μl/2×10⁶ platelets). Anti-CD42 and Anti-CD4 are monoclonal antibodies direct against specific surface receptors on the surface of each cell type. The different cell types were analyzed separately on the FACScan, gating only Anti-CD42-FITC positive platelets or Anti-CD4-FITC positive lymphocytes. The platelet and lymphocyte samples were also electronically sized on the electronic particle counter.

TABLE 2

Comparison of Optically and Electronically Measured Polystyrene Mcrosphere Radii

| Elzone Measured Radius <μm> | FACScan FALS Calculated Radius <μm> | Percent Difference |
|---|---|---|
| 0.43 | 0.43 | 1.16 |
| 0.52 | 0.56 | 6.50 |
| 0.68 | 0.67 | −1.47 |
| 0.87 | 0.91 | 4.62 |
| 0.99 | 1.00 | 0.25 |
| 1.97 | 2.07 | 4.66 |
| 2.77 | 2.73 | −1.46 |
| 4.49 | 4.57 | 1.68 |
| 7.69 | 7.70 | 0.11 |
| 9.60 | 11.63 | 21.21 |
| 10.15 | 9.39 | −7.55 |
| 13.86 | 14.10 | 1.67 |
| 16.49 | 16.36 | −0.81 |

Particle radius data represents the mean particle radius of monodisperse suspensions of polystyrene size calibration microspheres prepared in isotonic saline solution. For electronic particle sizing, 10,000 to 25,000 particles were characterized. Between 5,000 and 10,000 particles where measured on the flow cytometer for optical particle sizing.

Typical optically determined size distributions measured on the FACScan of FIG. 1 for fixed platelets and lymphocytes are shown in FIGS. 5 and 6, respectively, using the method of the present invention. The mean platelet diameter was determined to be 2.9 μm optically and 2.6 μm electronically. The mean lymphocyte diameter was determined to be 12.0 μm optically and 10.8 μm electronically. Optically determined size distributions were similar to the size distributions measured on the electronic particle counter, but were shifted slightly towards larger particle diameters.

The theoretical approach which was adhered to for purposes of optical sizing using the Becton Dickinson FAScan flow cytometer depends on the validity of three main assumptions. First, the amount of refracted and reflected light scatter collected by the FALS detector was assumed to be small compared to diffracted light. Second, Fraunhofer diffraction theory was assumed to be capable of describing the FALS measured in the flow cytometer. Third, prediction of biological cell size using the FDT equation developed for polystyrene microspheres was assumed to be possible despite the obvious differences between biological cells and polystyrene microspheres.

The validity of the first assumption can be tested by direct comparison of FDT and exact theory. This has been done by others for light scattering devices which collect forward angle light scatter over similar angles of FALS collection as used in the FACScan. Those studies report that the fraction of FALS due to refraction and reflection components combined ranges from 7% to 29% and is relatively insensitive to particle size.

As is the case in all light scatter devices, polystyrene microspheres of known size were used to calibrate the sizing characteristics of the FACScan. The use of polystyrene microspheres produced FALS measurements that, when analyzed through Fraunhofer diffraction theory, resulted in equipment parameters ($\theta_{min}$ and $\theta_{max}$) consistent with those reported by the manufacturer (Becton Dickinson FACScan User Manual). The fact that the equipment parameters determined by FDT match those reported by the manufacturer lends support to the validity of the first two assumptions. Additionally, the present method establishes that Fraunhofer diffraction theory can be used to correlate the forward angle light scatter measured on a FACScan flow cytometer with particle size. Particle sizes predicted from the FACScan's optical measurements agree within 2.1% of sizes measured using an electronic particle counter over a range from 0.33 μm to 9.03 μm in radius (Table 2). Theoretical analysis and actual measurements demonstrate that a unique relationship exists between particle radius and measured FALS for polystyrene calibration spheres.

Optical sizing on the FACScan was limited to particle radii less than 9 μm since multiple roots exist for particles in the range of 9.0<r<13.6 and 23.5<r<28.2. The existence of multiple roots has been reported by others. The anomalous behavior which results in multiple sizing roots is presumed to result from the variation in spacial positioning of diffraction pattern intensity lobes (concentric rings) with particle size. The most intense lobes are located at very small forward angles. As the particle radius increases, all forward scatter lobes move to smaller angles resulting in the loss of some measured intensity at angles below $\theta_{min}$ and the addition of some measured intensity near $\theta_{max}$. The rate at which the most intense lobes move below the minimum angle of collection can be shown to be different than the rate at which new lobes are moved within the maximum angle of collection. Coupling the differences in intensity of each lobe, the presence of a dark lobe between each bright lobe, and the rate at which the lobes move into and out of the angles of detection can account for the anomalous behavior where particles of distinctly different radii produce the same FALS.

By limiting optical sizing to particles less than 9 μm in radius, one potential source of sizing error can be eliminated. All light scatter theory requires complete illumination of the scattering particle. The FACScan utilizes an elliptical beam with minor and major axis of 20 μm and 60 μm respectively (Becton Dickinson FACScan User Manual). The use of the elliptical beam enhances pulse height and width resolution for triggering purposes. However, particles with diameters which exceed the minor axis of the beam spot are not completely illuminated at the time of pulse triggering. The alterations in the diffraction pattern which result from incomplete particle illumination compromise the accuracy of optical particle sizing by FDT.

Blurring due to measurement of the integrated light scatter intensity as the cell flows through the laser beam, producing a moving diffraction pattern, caused no noticeable degradation of the sizing theory. This is not surprising since each FALS measurements receives the same detector integration time regardless of particle size. Additionally, the sizing method developed here does not require knowledge of the discrete angular intensities of the diffraction pattern, but only the total integrated light intensity measured by the detector.

The underlying objective of the method is to characterize sizing on a flow cytometer for use with biological cell applications. The FACScan's optical parameters and resulting empirical sizing equation (Equation 4) were developed based on measurement of FALS for multiple samples of monodisperse polystyrene calibration spheres suspended in isotonic saline. Though the refractive index of polystyrene beads and biological cells are different, the use of polystyrene beads provides the basis to determine the optical parameters of the flow cytometer, in this embodiment the FACScan. Furthermore, light scatter theory suggests that refraction should not contribute a significant or meaningful amount of scatter to the FALS measurement. It would be very difficult to obtain the number of different sized biological cells types with low % cv's needed to determine the optical parameters. Additionally, it is realized that cells are not purely spherical or homogenous in internal composition and structure. Sizing of platelets and lymphocytes in this study was reproducible. Both cell types demonstrated similar distributions compared to those obtained on an electronic particle counter. In all experiments (n=11 for platelets and n=3 for lymphocytes), the mean particle size obtained from the FACscan was slightly larger than that measured on an electronic particle counter. The percent difference between optically and electronically determined cell sizes ranged from 5% to 18% with the optically determined mean spherical equivalent cell radius being 12% larger on average.

It is presumed that the differences in relative refractive index of polystyrene microspheres (m≈1.2) and fixed cells (m≈1.5) are responsible for the observed sizing errors. It is believed that the higher refractive index of fixed cells results in additional refracted light being collected in the FALS detection system. The result is an elevated FALS measurement due to the additional refracted light scatter component and the overprediction of cell radius. In support of this argument, optical sizing of non-fixed platelets (m≈1.02: data not shown, n=3) on the FACScan resulted in the prediction of a mean platelet diameter which was on average 6% less than that determined electronically.

The size distributions measured on the FACscan provide quantitative size information describing the biological cell populations with a relatively small degree of sizing error. The degree of sizing error observed in the biological cell sizing experiments is not unreasonable and may be improved by taking into account the differences between the refractive index of the calibration microspheres and cells. Use of the method indicates that the sizing performance of the flow cytometer can be improved by incorporating a term to correct for differences in refractive index between the size calibration spheres and the particles or cells being analyzed.

Another method which theoretically has the potential of increasing the sizing range and improving the sizing accuracy incorporates a second illumination source at a separate wavelength focused through the same optical path and focal point. Sizing by two wavelengths utilizes two sizing equations, each optimized for a desired particle size range with, perhaps, an overlap region where both equations are valid. Previous studies conducted with light scatter at two wavelengths have demonstrated increased cell population resolution. A correctly selected, two wavelength measurement system can also minimize or eliminate anomalous behavior which, theoretically, occurs in different ranges of the FALS scale. The second advantage is that an elliptical focal spot could continue to be used as trigger and the second illumination could utilize a larger focused spot size. The larger spot size would allow sizing of larger particles. Finally, it may be possible to discriminate the proportion of FALS resulting from refracted and diffracted light scatter.

The range over which the sizing equation is valid (0.22 µm to 9.03 µm in radius) is adequate for most mammalian cell studies. Optical particle sizing on a flow cytometer can provide researchers and clinicians with an additional parameter to use when analyzing flow cytometry dam. Using the size information collected on each cell, it is then possible in accordance with the present invention to decouple the fluorescence intensity measurement from its particle size dependency using either surface area normalization or volume normalization. Size normalization coupled with quantitative flow cytometric techniques provides the first opportunity to analyze receptor and antigen binding densities on a per cell basis. Analysis of receptor, antigen, and membrane protein surface concentrations in the form of binding densities can be extremely useful when studying cells, such as platelets, which vary significantly in size or change size due cell phase, activation, or aggregation.

It is important to note that Equation 4 was determined based on the optical parameters specific to the Becton Dickinson FACScan used in this study. The same equation may not provide reliable sizing from FALS collected from other flow cytometers or on another FACScan. The parameters determined for Equation 4 were based on the laser output intensity and limiting angles of collection fixed on the FACScan used in this study. FIGS. 25–28 plot theoretical particle size versus forward angle light scatter curves which are predicted by FDT, using the methodologies of the present invention at varying minimum and maximum angles of light scatter. Similar equations can be developed for other flow cytometers by following the method described here.

It should be possible using another flow cytometer (such as the B-D FACStar Plus) to adjust the obscuration bar and aperture such that the limiting angles of collection result in the desired sizing range free of anomalous regions. This process should move the range of anomalous behavior up or down the FALS scale. If this is possible, similar equations may be developed which are capable of sizing over a larger range of measured FALS.

The methods of the present invention were applied to the study of platelets and platelet activation. Examples, then, of use of the methods are given below. However, it is not intended that such examples indicate any limitation on the application of the methods. It will be apparent to those skilled in the art that the basic methods described and claimed herein will have application to a wide variety of biological particles.

EXAMPLE 1

APPLICATION OF SURFACE AREA NORMALIZATION TO STUDY CHANGES IN PLATELET MEMBRANE GLYCOPROTEIN EXPRESSION FOLLOWING ACTIVATION

Introduction

Platelets are specialized cells involved in the initialization and formation of blood clots. Platelets are discoid in shape with a diameter range of 1 to 5 micrometers. Normal human blood platelet concentrations range between 175,000 to 350,000 platelets per microliter. The presence of platelets is vital in arresting hemorrhaging at the site of vascular injury. Platelets are normally non-adherent, but in the presence of cellular or vascular injury, abnormal hemodynamic flow, and certain biochemical agents, platelets become adherent to each other, other blood cells, endothelial cells, and the sub-endothelial matrix. Platelet activation and aggregation result in the formation of a temporary plug which arrests bleeding. Additionally, a cascade reaction of coagulation co-factors produces a network of insoluble biological polymers which persists until vascular repair is complete.

Platelet activation and aggregation is an essential part of hemostasis. However, life threatening thrombotic and atherosclerotic complications following surgical implantation of artificial vascular prosthesis, heart valves, and other artificial organs have been attributed, at least in part, to platelet activation. It is believed that the elevated fluid dynamic forces associated with the use of these devices may play a significant role in the associated platelet activation.

Another area of great concern is rapid restenosis of atherosclerotic vessels following balloon angioplasty. Balloon angioplasty results in the formation of vasculature fissures, exposing the subendothelial matrix. Platelet exposure to collagen in the subendothelial matrix induces the formation of extensive fibrin-platelet clots. It is believed that the massive fibrin-platelet clot, which forms almost immediately and persist for some time, creates a region of blood flow characterized by elevated shear rates. The elevated shear stress induces further platelet activation. The activated platelets adhere to the fibrin-platelet clot and the surrounding vascular endothelium. The process of activation and adhesion continues, compounding the problem, and results in the process called platelet spreading.

A vast amount of data has been produced describing platelet activation in response to chemical agonist and fluid dynamic forces. The work completed to present on chemically induced activation has significantly improved our understanding of the various platelet activation pathways which may be involved in platelet activation induced by fluid dynamic forces. Past studies of platelet response to fluid dynamic forces have concentrated primarily on shear stress effects. Platelet response to elongational fluid stress at levels present in the vasculature has also been investigated. Studies of platelet activation induced by dynamic fluid forces have, as yet, failed to produce a generally recognized biological mechanism for SIPAC or identified the pathway(s) involved.

An increase in the free intracellular calcium ion concentration ($[Ca^{2+}]_i$) has been identified in most studies of platelet activation, whether induced by chemical agonist, fluid dynamic forces, or surface contact. Calcium is viewed as a universal "second messenger" because of its seemingly important role as a switch for initiating other activation events. The importance of calcium ions as a second messenger is not limited to platelets. The role of calcium ion has been documented for initiating contraction in smooth and skeletal muscle, as well as release of many hormones and neuro-transmitters. The normal, resting platelet $[Ca^{2+}]_i$ has been measured in the range of 90 nM to 150 nM. A large concentration gradient exists between intracellular concentration and the normal, plasma calcium ion concentration of approximately 1 mM. The large concentration gradient creates a strong driving force for calcium ion influx into the platelet. Platelets are capable of maintaining their hemostatic free intracellular calcium ion equilibrium by sequestering excess free calcium ions into the dense tubular system and secretory vesicles and by the active transport of free calcium ions from the platelet using $Ca^{2+}$ pumps. The steady state calcium ion flux in resting, intact platelets has been reported to be 1.53 pmole/$10^8$ platelets/min. Assuming an average platelet volume of 4.19 $\mu m^3$, the reported flux equates to a molar exchange rate of 3.65 $\mu M$/min. For resting, intact platelets, the efflux plus the sequestering of free cytosolic calcium ion equals the calcium ion influx. However, during platelet activation the influx of free calcium ions into the cell exceeds the platelets' ability to maintain its desired hemostatic concentration and the $[Ca^{2+}]_i$ increases. The means and source of the increased influx of free intracellular calcium ions during shear stress exposure is not well understood.

The increase in $[Ca^{2+}]_i$ following platelet activation by chemical agonist is viewed as an essential step since EDTA chelation of free calcium ions prevents normal platelet dense granule release and aggregation. Interpretation of these studies is complicated by irreversible glycoprotein alterations induced by EDTA. Release of sequestered calcium ion from internal stores has been reported to be the initial source of increased free cytosolic calcium ions during the initial stage of platelet activation characterized by shape changes. The largest internal store of free calcium ions is located in the dense tubular system. The increase in $[Ca^{2+}]_i$, at least at later times, is too great to have resulted solely from release of internal stores. Therefore, an increase in transmembrane influx of calcium ion must also accompany release from internal stores. It has been shown, using calcium ionophore A23187, that an increase in the free $[Ca^{2+}]_i$ without prior platelet activation is capable of inducing platelet activation and aggregation.

An increase in $[Ca^{2+}]_i$ is also associated with shear induced platelet activation. Increased $[Ca^{2+}]_i$ associated with SIPAC may be the primary activation step or the result of an earlier, as yet, undetermined activation step(s). Other activation events coincide with or immediately follow the rapid increase in $[Ca^{2+}]_i$, such as dense granule release, intracellular pH changes, changes in phosphorylation, changes to G proteins, shape change, and eventually aggregation. Dense granule release, intracellular pH changes, shape change, and platelet aggregation have been measured during shear stress exposure.

The most recent studies of SIPAC have shifted attention to platelet membrane receptors, transmembrane signaling, and adhesion proteins. Synthetic peptides containing the amino acid sequences, Arg-Gly-Asp (RGDs), and monoclonal antibodies (MoAbs) have been used to block receptor sites for the adhesion proteins, fibrinogen (Fg) and von Willebrand Factor (vWF), in an attempt to elucidate which adhesion protein and membrane receptors are involved in SIPAC. Calcium ion channel blockers and pathway inhibitors are also being employed to investigate the pathway(s) involved in SIPAC.

At low shear rates, fibrinogen bound to platelet glycoprotein GP IIb/IIIa appears to be the primary adhesion protein-receptor complex involved in SIPAC. Recent reports indicate that vWF is the predominant adhesion protein involved during high shear rate exposure and that vWF binds to both GP IIb/IIIa and GP Ib. Complete inhibition of SIPAC at all shear rates by prior incubation of washed platelets with 6D1, a MoAb which binds to or blocks the vWF binding domain located on GP Ib, has been reported. However, these studies do not quantify the amount of bound adhesion proteins or the number of receptor sites involved. These studies also do not address changes in the expression of platelet membrane receptors as a result of shear stress exposure. The primary induction mechanism remains unknown.

Flow cytometry has been shown to be a useful tool in the study of platelet physiology. It has been used extensively in the study of platelet activation induced by chemical agonists. New antibodies are available which recognize activation epitopes on membrane receptors, ligand induced binding sites (LIBS), receptor induced binding sites (RIBS), various adhesion proteins, as well as commonly expressed membrane proteins. Using these antibodies, flow cytometry has been used to study platelet activation induced by surgical procedures such as open heart surgery, heart bypass, and balloon angioplasty.

The relationship between the biological mechanisms responsible for platelet activation at the site of vascular injury and platelet activation induced by fluid forces is still mostly unknown. Further characterization and understanding of platelet activation processes, especially the pathway(s) and mechanism(s) involved in SIPAC, is necessary in order to improve engineering design of vascular prosthesis and artificial organs and to develop better pharmaceuticals to reduce SIPAC complications. Though a significant body of data has been collected which characterizes SIPAC, most of the data collected is of bulk fluid changes. Very little data exist describing platelet changes measured on a molecular level. Molecular level assays for platelet activation states should provide additional detailed information about the mechanism(s) and pathway(s) involved in SIPAC. Additionally, molecular level assay studies may lead to the development of clinical assays for early detection of in vivo SIPAC complications.

Flow cytometry is a useful tool for the study of platelet physiology. Platelet activation, α granule release, changes in platelet membrane receptor expression and binding of adhesion molecules following activation by chemical agonist and medical treatment have been studied using flow cytometry. Other studies have measured increased platelet activation following heart bypass and balloon angioplasty using flow cytometry combined with event or conformation specific monoclonal antibodies (MoAbs). However, flow cytometric results can be difficult to interpret due to the size heterogeneity of the platelet population. The diameter of normal, single platelets may range from 1 to 5 μm which yields a 25-fold difference in surface area. The surface area per event varies significantly within a normal platelet population distribution. Very few platelet studies have taken into account the fact that fluorescence intensity measurements are directly related to the size of the particle measured as well as the surface distribution of bound fluorescently conjugated monoclonal antibody. Those studies which have considered platelet size changes have done so by gating only on single platelet events. If receptor surface density is constant, the total number of MoAb molecules bound to each platelet will be a function of the event size. Additionally, activation of platelets induces the release of micro-vesicles and the formation of large aggregates which further increases the surface area distribution of the platelet population being studied.

The study of changes in platelet membrane receptors expressed following activation is one in which surface area or volume normalization can greatly aid in the interpretation of flow cytometric results. Surface area or volume normalization should sharpen the fluorescence intensity distribution by removing the particle size dependency. Cytometric analysis of a hypothetical single cell population without variation in size or MoAb binding density would produce fluorescence intensity measurements in a single channel. If the same cells have a distribution of sizes and form aggregates, the measured fluorescence intensity of aggregates will be greater than that of single cells and the fluorescence intensity of the single cells alone will be a direct function of the size distribution. By surface area normalization, the binding density of MoAbs to single cells and aggregates can be compared directly. The same technique can be applied to demonstrate the existence of MoAb binding density differences in samples with heterogeneous sizes. Surface area and volume normalization should allow cells with abnormal receptor densities to be distinguished from normal cells and activated cells from resting cells with increased resolution.

Using the method of the present invention, the power of flow cytometry can be applied to determine the cell surface receptor density on individual cells. Individual cell measurements can be used to observe variations within a population, changes in expression resulting from chemical treatment, or differences due to various phases of the cell cycle. Surface area normalization (SAN) or volume normalization of fluorescence intensity measurements enhances the ability to distinguish subpopulations of cells and characterize membrane alterations by eliminating the size variable.

Application of the novel surface area and volume normalization method of the invention provides additional flow cytometric data, independent of size, to assist in the analysis of platelet activation, as an example. The radius of single platelets and platelet aggregates are calculated directly from the forward angle light scatter intensity (FALS) measured on a Becton Dickinson FACScan flow cytometer using the semi-empirical equations developed in accordance with the method described above. The expression of platelet membrane receptors are then surface area normalized using the equivalent spherical surface area calculated from the optically measured particle radius. The expression of GP Ib, GP IIb/IIIa, and GMP 140 on the surface of resting and phorbol myristate acetate (PMA) stimulated platelets was used to evaluate the utility of surface area normalization.

Materials and Methods

Biological Cell Preparation

Platelets were obtained by venipuncture from normal individuals. All donors were self-reported to be medication-free within two weeks prior to donating blood. All platelet samples were characterized on the FACScan within 5 days of venipuncture and labeling.

Platelet rich plasma was aspirated from blood anticoagulated with 0.105M (3.2%) buffered citrate solution (24.7 mg/ml $Na_3$citrate.$2H_2O$ and 4.42 mg/ml citric acid.$1H_2O$) at a volume ratio of 1 to 9 and centrifuged at 150× g for 25 minutes. The platelet rich plasma was aliquoted into two 500 μl volumes. One aliquot was treated with phorbol myristate acetate (PMA) at a final concentration of 0.2 μM. At 5 minutes, both the control and PMA treated aliquots were fixed by addition of paraformaldehyde to a 1% final concentration. Control and treated aliquots were diluted to a platelet concentration of 2×10⁷ platelets per ml by the addition of a stock HEPES buffer solution (HBS) (10 mM HEPES, 145 mM NaCl, 5 mM KCl, 0.5 mM NaHPO4, and 1 mM $MgCl_2$) containing 1% paraformaldehyde and allowed to fix at 4° C. for at least 2 hours before labeling.

Monoclonal Antibody Labeling

Sample volumes of 100 µl, containing approximately $2\times10^6$ platelets were pipetted into separate polystyrene tubes and washed twice with HBS containing no paraformaldehyde. Platelets were labeled with Anti-CD41-FITC (GenTrak, Inc., Plymouth Meeting, Pa.; Cat.#0027-0649: 2.5 µl/$2\times10^6$ platelets), Anti-CD42b-FITC (GenTrak, Inc.; Cat.#0027-0648: 2.5 µl/$2\times10^6$ platelets), CD62-PE (Becton Dickinson Immunocytometry Systems, San Jose, Calif.; Cat.#348107: 5.0 µl/$2\times10^6$ platelets) and MSIgG-PE (GenTrak, Inc.; Cat.#0027-0670: 2.5 µl/$2\times10^6$ platelets). Two color labeling was performed using the following monoclonal antibody (MoAb) combinations: CD41-FITC with CD62-PE, CD42-FITC with CD62-PE, and CD42-FITC with MSIgG-PE. Two color labeling was accomplished by adding the stated concentrations of both MoAbs simultaneously and incubating in the dark for 30 minutes at room temperature. The control and treated samples were subsequently washed twice with HBS containing no paraformaldehyde. The platelets were finally re-suspended in HBS containing 1% paraformaldehyde at a platelet concentration of $2\times10^6$ platelets per ml and stored at 4° C. until flow cytometric analysis.

Flow Cytometry

All samples were analyzed in a Becton-Dickinson FACScan flow cytometer. The FACScan was setup and calibrated as described above. Ten thousand platelet particles distinctly positive for either CD41-FITC or CD42-FITC, presumed to be single platelets and platelet aggregates, were counted from each sample. Data analysis was performed using WINLIST (Verity Software House, Inc., Topsham, Me.) installed on a 33 MHz 80486DX based microcomputer. The program allows equations to be entered and used as calculated parameters during data analysis. Forward angle light scatter conversion to particle size and size normalization of fluorescence intensity measurements were accomplished using the calculated parameter capability of WINLIST software.

Optical Sizing

Particle radius was calculated from the forward angle light scatter intensity (FALS) measured on the FACScan using the method described above. The equations are entered as calculated parameters in WINLIST and are used to calculate the particle radius of each gated event. Particle sizing was limited to the particle size range from 0.7 µm to 18.0 µm in diameter.

Size Calibration Spheres

A standard size calibration solution was prepared in isotonic saline containing 1.09, 2.02, and 9.97 µm diameter polystyrene calibration spheres. Calibration spheres of 1.09 and 2.02 µm in diameter were purchased from Particle Data Inc. (Elmhurst, Ill.) while the 9.97 µm diameter spheres were purchased from Polyscience Inc. (Warrington, Pa.). Calibration spheres suspended in isotonic saline were measured with an Elzone PC-285 electronic particle counter (Particle Data, Inc., Elmhurst, Ill.) to confirm the size distribution reported by the manufacturer. The standard size calibration solution was analyzed on the flow cytometer before and after each set of cell characterizations as a size control. The standard size calibration solution was size analyzed periodically with the electronic particle counter to confirm the stability of the calibration spheres.

FACScan MESF Calibration

A mean equivalent soluble fluorescence (MESF) calibration curve was determined for each of the fluorescence detectors. This procedure assigns a quantitative MESF value to each fluorescence channel. The QUANTUM 1000 MESF calibration kit (Flow Cytometry Standards Corporation, Research Triangle Park, N.C.) was used to determine the MESF calibration curve for the fluorocein (FITC) and R-phycoerythrin (PE) fluorescence detectors. It is imperative that the quantitative MESF beads used be labeled with a fluorochrome with identical excitation and emission spectrum as the fluorochrome conjugate used. The Quantum 1000 kit contains a certified blank, four sets of MESF beads of different quantified MESF values for FITC and four sets for PE. The mean soluble equivalent fluorocein fluorescence ranged from 16,000 to 480,000 MESF. The mean soluble equivalent R-phycoerythrin fluorescence ranged from 16,000 to 560,000 MESF.

One MESF calibration suspension contained the certified blank and the four quantified FITC MESF beads. A second MESF calibration suspension contained the certified blank and the four quantified PE MESF beads. Both MESF calibration suspensions were prepared in HBS. Each suspension was analyzed daily on the FACScan to determine the mean logarithmic fluorescence channel of the blank and the calibrated MESF beads. The mean logarithmic fluorescence channel for each bead was plotted against the logarithm of the corresponding MESF value reported by the manufacturer. The logarithmic fluorescence channels were a linear function of the logarithm of the reported MESF values for FITC and for PE. Linear regression was performed to determine the equation which related MESF values to the logarithmic fluorescence channels for each of the fluorophores.

Effective F/P Ratios

The effective fluorescence to protein (F/P) ratio is the measurement of the mean equivalent soluble fluorescence conjugated to each molecule of MoAb. The effective F/P ratio of fluorescently conjugated MoAbs was determined by reacting fluorochrome-conjugated MoAbs with microspheres calibrated with a known number of anti-mouse IgG binding sites (Simply Cellular Microspheres, Flow Cytometry Standards Corporation, Research Triangle Park, N.C.).

Simply Cellular Microspheres were reacted with saturating concentrations of the directly conjugated MoAbs, washed once and suspended in HBS. The mean fluorescence intensity per MoAb-saturated microsphere was determined by flow cytometry. The mean fluorescence intensities of the microspheres were converted to MESF values using the previously determined MESF calibration curves. The effective F/P ratio for each fluorescently conjugated MoAb was then determined by dividing the mean MESF value per MoAb-saturated microsphere by the number of binding sites per microsphere reported by the manufacturer.

Receptor Density Calculation

The number of bound monoclonal antibody (MoAb) molecules per flow cytometric event can be readily calculated by dividing the MESF measured for each event by the effective F/P ratio of the fluorescently conjugated MoAb used. It is important to note that the flow cytometer collects scatter and fluorescence data on a per event basis. It is not correct to assume that each event is a single cell. The event may be, for example, a cell fragment or an aggregate of many cells.

The particle radius of each event was calculated from the forward angle light scatter intensity (FALS) measured on a FACScan flow cytometer. The optically determined particle radius was used to calculate an equivalent spherical surface area for each event. The MoAb binding density, defined as the number of bound MoAb molecules per unit surface area, was calculated by dividing the number of bound MoAb molecules per event by the surface area of that event.

This technique identifies subpopulations that express a significantly different MoAb binding density than that of the whole population. The value calculated for the MoAb binding density may be interpreted as the cell receptor or antigen density if a saturating concentration of MoAb is used during labeling and steric hinderance does not prevent binding of MoAb to all available receptor sites.

Results

FIG. 7 presents typical size distribution histograms of control platelets measured on a prior art electronic particle counter and calculated from the FACScan's FALS measurements using the method of the present invention. This presentation illustrates the similar platelet size distributions produced by the two completely different measurement techniques. The mean platelet diameter determined on the FACScan was on average within 14% of that measured on the electronic particle counter.

Typical control and PMA stimulated fluorescence distributions per event and MoAb binding per $\mu m^2$ for CD41 and CD62 are presented in FIGS. 8 and 9, respectively. Expression of CD41-FITC fluorescence per event, in this representative experiment, decreased following activation with 1.0 $\mu M$ PMA from a mean value of 345 FITC arbitrary intensity units (a.i.u.) per event (covariance (cv)=7.3%) for the control sample (FIG. 8a) to a mean value of 255 FITC a.i.u. per event (cv=13.0%) for the treated sample (FIG. 8c). Covariance is used to describe the individual histogram distribution about the histogram mean. Surface area normalization of the same data resulted in a decrease in bound CD41 per $\mu m^2$ from a mean value of 5238 bound CD41 molecules per $\mu m^2$ (cv=4.5%) to 4273 bound CD41 molecules per $\mu m^2$ (cv=5.4%) for the control sample (FIG. 8b) and treated sample (FIG. 8d), respectively. Expression of CD62-PE fluorescence per event increased following activation with 1.0 $\mu M$ PMA from a mean value of 3.6 PE a.i.u. per event (cv=79.8%) for the control sample (FIG. 9a) to a mean value of 80.9 PE a.i.u. per event (cv=28.9%) for the treated sample (FIG. 9c). Following SAN, CD62 binding density increased from 15.5 bound CD62 molecules per $\mu m^2$ (cv=42.8%) to 491.7 bound CD62 molecules per $\mu m^2$ (cv=17.6%) for the control sample (FIG. 9b) and treated sample (FIG. 9d), respectively.

The calculation of bound MoAb molecules per event from the raw fluorescence data, using the quantitative techniques described in this work, shifts the distribution up or down the axis scale without changing the distributions shape or covariance. For this reason all the results that follow are presented in terms of bound MoAb molecules per event and per $\mu^2$.

In several PMA activation studies, using 0.1 $\mu M$ PMA, an unusual CD62-PE fluorescence distribution was observed. One of these unusual CD62 binding distributions is shown in FIG. 10a. Surface area normalization of these studies produced distinct bimodal distributions for the expression of bound CD62 molecules per $\mu m^2$, as shown in FIG. 10b for this representative case.

The value of surface area normalization in the study of platelet activation can also be illustrated by dividing the platelet population into three size categories: 1) small platelets (0.33 $\mu m \leq r < 0.91$ $\mu m$), 2) platelet singlets (0.91 $\mu m \leq r \leq 2.19$ $\mu m$), and 3) platelet aggregates (2.19 $\mu m < r \leq 8.98$ $\mu m$). The size categories were established by first defining the platelet singlet population as the particle size range which contained 90% of the total control platelet count. The small platelet and platelet aggregate populations were composed of particles which were beyond the platelet singlets size region. Receptor site expression was analyzed within each of these size gates as well as for the entire population positively marked with either CD41 or CD42. Use of particle size as a gating parameter is uniquely provided by the method described above. CD41, CD42, CD62, MSIgG binding by particle size is presented in FIG. 11 for control and PMA treated PRP samples.

The expression of bound CD41 molecules per event increased significantly (two-way ANOVA, p<0.05) with increased particle size for both control and treated platelet samples (Table 3). However, following SAN, no significant differences in the expression of bound CD41 molecules per $\mu^2$ were detectable as a function of particle size for either control or treated platelet samples (Table 4). Statistical analysis of CD42 binding exhibited nearly the same statistical pattern as reported for CD41. Differences between the statistical patterns of CD42 and CD41 are indicated in Table 3 and Table 4. No significant changes in either CD41 or CD42 binding for either non-SAN or SAN data were measured following PMA activation when comparing the same size categories of control samples to their corresponding PMA activated samples.

TABLE 3

Summary of Statistical Comparisons on Non-Normalized Bound CD41 Molecules per Event

| Non-Surface Area Normalized | Control Small | Control Single | Control Aggregate | Treated Total | Treated Small | Treated Single | Treated Aggregate |
|---|---|---|---|---|---|---|---|
| Control Total | Yes | No | Yes | No | Yes | No | Yes |
| Control Small | | Yes | Yes | No[a] | No | No[a] | Yes |
| Control Single | | | Yes | No | Yes | No | Yes |
| Control Aggregate | | | | Yes | Yes | Yes | No |
| Treated Total | | | | | Yes | No | Yes |
| Treated Small | | | | | | Yes | Yes |
| Treated Single | | | | | | | Yes |

Statistical comparisons performed on non-nomalized CD41 binding data from non-activated control and PMA treated platelet samples (see FIG. 11) using Two-Way ANOVA with $\alpha = 0.05$. Significant difference (p < 0.05) between the pairing is indicated by "Yes". No significant difference is indicated by "No". Statistical comparisons performed on non-normalized CD42 binding data yielded identical statistical results unless denoted by "[a]". "[a]" indicates that the opposite result was determined for statistical analysis performed on non-normalized CD42 binding data.

Statistical analysis of CD62 binding reveals a distinctly different pattern. CD62 is used as an platelet activation marker, detection of α granule release. Significant (two-way ANOVA, p<0.05) increases in CD62 binding were measured for all comparisons of non-SAN and SAN data following PMA activation when comparing the same size categories of control samples to their corresponding PMA activated samples. Analysis of bound CD62 molecules per event for PMA treated samples indicates that the large platelet aggregates formed following PMA stimulations express significantly greater number of bound CD62 molecules per event (Table 5). However, analysis of CD62 binding data following surface area normalization presents a different picture of α granule release (Table 6). In non-activated control samples, the number

Discussion

FIG. 7 illustrates a comparison of platelet size distributions measured using the FALS particle size calculation techniques of the present invention on the FACScan of FIG. 1 and as measured by a conventional electronic particle counter. These data demonstrate that optical sizing provides a representative platelet size histogram. Differences in the mean platelet sizes determined by the two distinctly different sizing techniques can be attributed to differences between the refractive index of the polystyrene size calibration microspheres and fixed platelets. Optical sizing of platelets provides an additional cytometric parameter for size gating and surface area normalization of surface bound fluorescent markers of platelet activation.

TABLE 4

Summary of Statistical Comparisons on Surface Area Normalized Bound CD41 Molecules per $\mu^2$

| Non-Surface Area Normalized | Control Small | Control Single | Control Aggregate | Treated Total | Treated Small | Treated Single | Treated Aggregate |
|---|---|---|---|---|---|---|---|
| Control Total | No | No | No | No | No | No | No |
| Control Small |  | No | No | No | No | No | No |
| Control Single |  |  | No | No | No | No | No |
| Control Aggregate |  |  |  | No | No | No | No |
| Treated Total |  |  |  |  | No | No | No |
| Treated Small |  |  |  |  |  | No | No |
| Treated Single |  |  |  |  |  |  | No |

Statistical comparisons performed on surface area normalized CD41 binding data from non-activated control and PMA treated platelet samples (see FIG. 11) using Two-Way ANOVA with α = 0.05. Significant difference (p < 0.05) between the pairing is indicated by "Yes". No significant difference is indicated by "No". Statistical comparisons performed on surface area normalized CD42 binding data yielded identical statistical results unless denoted by "a". "a"indicates that the opposite result was determined for statistical analysis performed on surface area normalized CD42 binding data.

bound CD62 molecules per $\mu^2$ determined for the small platelet category is statistically greater than the binding densities measured all other control sample size categories. Furthermore, no statistical differences in CD62 binding densities were detectable between the size categories of PMA treated samples.

Both control and treated samples exhibited the same statistical pattern for MSIgG binding density, where the small platelet category showed a statistically greater binding density than the other size categories when comparing like samples. MSIgG binding did not change significantly as a result of PMA stimulation.

Measurement of platelet activation by flow cytometry is better resolved and more easily

TABLE 5

Summary of Statistical Comparisons on Non-Normalized Bound CD62 Molecules per Event

| Non-Surface Area Normalized | Control Small | Control Single | Control Aggregate | Treated Total | Treated Small | Treated Single | Treated Aggregate |
|---|---|---|---|---|---|---|---|
| Control Total | No | No | No | Yes[a] | No | No | Yes |
| Control Small |  | No | No | No | Yes[a] | No | Yes |
| Control Single |  |  | No | No | No | Yes[a] | Yes |
| Control Aggregate |  |  |  | No | No | No | Yes[a] |
| Treated Total |  |  |  |  | No | No | Yes |
| Treated Small |  |  |  |  |  | No | Yes |
| Treated Single |  |  |  |  |  |  | Yes |

Statistical comparisons performed on non-normalized CD62 binding data from non-activated control and PMA treated platelet samples (see FIG. 11) using Two-Way ANOVA with α = 0.05. Significant difference (p < 0.05) between the pairing is indicated by "Yes". No significant difference is indicated by "No". Statistical comparisons performed on non-normalized MSIgG binding data yielded identical statistical results unless denoted by "a". "a" indicated that the opposite result was determiend for statistical analysis performed on non-normalized MSIgG binding data.

TABLE 6

Summary of Statistical Comparisons on Surface Area Normalized Bound CD62 Molecules per $\mu^2$

| Non-Surface Area Normalized | Control Small | Control Single | Control Aggregate | Treated Total | Treated Small | Treated Single | Treated Aggregate |
|---|---|---|---|---|---|---|---|
| Control Total | Yes | No | No | Yes[a] | Yes | Yes[a] | Yes[a] |
| Control Small |  | Yes | Yes | Yes | Yes[a] | Yes | Yes |
| Control Single |  |  | No | Yes[a] | Yes | Yes[a] | Yes[a] |
| Control Aggregate |  |  |  | Yes[a] | Yes | Yes[a] | Yes[a] |
| Treated Total |  |  |  |  | No[a] | No | No[a] |
| Treated Small |  |  |  |  |  | No[a] | No[a] |
| Treated Single |  |  |  |  |  |  | No |

Statistical comparisons performed on surface area normalized CD62 binding data from non-activated control and PMA treated platelet samples (see FIG. 11) using Two-Way ANOVA with $\alpha = 0.05$. Significant difference ($p < 0.05$) between the pairing is indicated by "Yes". No significant difference is indicated by "No". Statistical comparisons performed on surface area normalized MSIgG binding data yielded identical statistical results unless denoted by "[a]". "[a]" indicated that the opposite result was determined for statistical analysis performed on surface area normalized MSIgG binding data.

interpreted when surface area normalization is applied. Data analysis and interpretation of SAN results is based on fluorescence intensity measurements which represent receptor expression independent of cell size, as demonstrated in FIGS. 8 through 10. The receptor site density histogram is better defined than similar histograms based on MoAb binding per event and allows for detection of smaller shifts in MoAb binding. FIGS. 8 and 9 demonstrate the ability of SAN as employed in the present invention to resolve binding distributions by producing a more interpretable clustering pattern and reducing the covariance of the distributions.

SAN improves interpretation of measured changes in MoAb binding expression. The bimodal distribution of FIG. 10b, platelets activated by 0.1 μM PMA, is an example of the additional information SAN using the method of the present invention can provide. Others have also observed bimodal distributions for GMP-140 expression in platelets using other agonist. Presumably, the first peak of FIG. 10b corresponds to submaximally activated platelet expression of bound CD62, while the second peak represents the platelet population which was fully activated and experienced α granule release. The bimodal CD62 binding density distributions observed were not an artifact of platelet asymmetry or the surface area normalization technique since the positive platelet marker (CD41) collected simultaneously always exhibited a normal, single mode distribution. Additionally, two color experiments conducted using CD42 as the positive platelet marker exhibited identical bimodal CD62 binding density distributions, thereby ruling out steric effects of the positive platelet MoAb used. Without surface area normalization it is impossible to determine the relative roles of increased GMP-140 expression and platelet size alterations in the development of the second fluorescence peak.

Others have noted that a large fraction of platelets, usually of small diameter, do not seem to participate in aggregation. The bimodal distribution presented in FIG. 10 may be interpreted to reveal the fraction of platelets involved in activation and the degree to which the two populations were activated. Quantitation of the percent α granule release and activation from MoAb binding dam is possible only after SAN. Quantitation of activation is not possible without SAN, since changes in measured MoAb binding may be coupled with the simultaneous change in single platelet size and aggregation.

CD41, CD42, and MSIgG binding density did not change significantly following PMA activation. However, platelets in the small platelet population subset of control and PMA stimulated samples were found to have a significantly higher MSIgG binding density than other platelet sizes. It is not fully understood why small platelets would express a significantly higher degree of non-specific binding. This observation may be the result of platelet age and hemopoietic degradation or an increased expression of Fc receptors.

Although changes in CD41 and CD42 binding densities were not found to be significant, it is evident by close examination of FIG. 11 that these binding densities decreased slightly following PMA activation. FIG. 11 graphically shows a comparison of binding densities for control and activated platelets as determined with surface area normalization as described in the present invention, and conventionally with SAN. The slight decrease in CD41 and CD42 binding densities is most likely due to steric or competitive inhibition of MoAb binding due to the existence of fibrinogen and possibly von Willebrand factor bound to the respective receptors. Additionally, competitive inhibition may also prevent binding of these MoAbs to any upregulated receptors from intracellular pools of GP IIb/IIIa and GP Ib. Other MoAbs to GP IIb/IIIa and GP Ib which recognize epitopes not effected or stericly hidden by binding of adhesive proteins may provide clearer information regarding regulation of surface concentrations of GP IIb/IIIa and GP Ib.

CD62 binding to CD41 positive particles within the platelet singlets category increased significantly (two-way ANOVA, $p<0.05$) from $402\pm168$ (n=9) bound CD62 molecules per event for control samples to $11,698\pm2,853$ (n=9) bound CD62 molecules per event for PMA treated samples. Following SAN, CD62 binding densities increased significantly ($p<0.05$) from $17\pm12$ (n=9) molecules per $\mu m^2$ for the control samples to $467\pm187$ (n=9) molecules per $\mu m^2$ for the PMA activated samples. Therefore, the increase in CD62 binding was not a function of size but a true function of platelet activation. CD62 binding presented here agrees with the expression of GMP-140 specific MoAbs reported by others.

Statistical analysis of CD62 binding density as a function of platelet size suggests the presence of small platelets in the control samples with a significantly higher GMP-140 surface concentration. Small particles in the control samples with statistically elevated CD62 binding densities presumably represent platelets or a platelet subpopulation which became activated during PRP processing. However, this elevated measure of CD62 binding density may only reflect the elevated non-specific binding also observed in this size category.

Surface area normalization was shown to be a useful tool for resolving binding site densities in platelet activation studies. Differences or changes in fluorescence intensities can be definitively resolved by surface area normalization to changes in receptor site expression and differences in particle size and aggregation. Surface area normalized flow cytometry has the added benefit of measuring the binding density per surface area for each cell which is not possible by RIA, ELISA, and gel electrophoresis methods. Accurate assessment of the receptor site density distribution for the entire platelet population can be obtained by this technique. Assuming a normal platelet size of 2 μm in diameter and a 1:1 ratio for MoAb binding to receptor, the mean binding densities of 4815 bound CD41 molecules per $\mu^2$ and 2252 bound CD42 molecules per $\mu^2$ correspond to 60,525 GP IIb/IIIa and 28,308 GP Ib receptors per platelet. These values determined by quantitative flow cytometry correlate well with the receptor enumerations reported by radiometric techniques.

Surface area normalization of cytometric platelet surface receptor binding data may be correlated with patterns for platelet disease recognition. Such correlations may provide additional information on disease processes. It may be possible to quantify platelet surface receptor and antigen expression in such a way as to allow clinical and diagnostic ranges to be established. The ultimate goal being the development of clinical assays for routine screening and early detection of in vivo platelet activation induced by arterial blockage, atherosclerotic, and thrombotic processes.

EXAMPLE 2

FLOW CYTOMETRIC QUANTITATION OF FIBRINOGEN AND VON WILLEBRAND FACTOR BINDING TO CHEMICALLY STIMULATED PLATELETS

The study of adhesive protein binding by quantitative flow cytometry provides valuable information regarding platelet activation and aggregation. Previous studies of adhesive protein binding have used RIA, ELISA, or radiolabeling techniques for quantitation. Competitive inhibitors and blockers have been routinely used to ascertain binding preferences in response to various stimuli. With the increasing availability of highly specific monoclonal antibodies (MoAb) toward most adhesive proteins, it is possible to investigate receptor-ligand interactions by flow cytometry.

Flow cytometry has become a useful tool for studying platelet physiology. Platelet activation, α granule release, changes in platelet membrane receptor expression, and binding of adhesion molecules following activation by chemical agonist and medical treatment have been studied using flow cytometry. Other studies have measured increased platelet activation following heart bypass and balloon angioplasty using flow cytometric methods. However, flow cytometric results can be difficult to interpret due to the size heterogeneity of the platelet population.

The new quantitative flow cytometric method offers greater precision in the evaluation and interpretation of activation and aggregation events which occur on the surface of biological particles. Quantitative flow cytometry provides a specific, quantified adhesive protein binding density for each individual platelet analyzed. Since large numbers of platelets can be analyzed from each sample, a binding density distribution can be constructed which accurately describes the entire platelet population.

Materials and Methods

Biological Cell Preparation

Platelets were obtained by venipuncture from normal individuals. All donors were self-reported to be medication-free within two weeks prior to donating blood. All platelet samples were characterized on the Becton Dickinson FACScan flow cytometer within five days of venipuncture and labeling.

Platelet rich plasma was aspirated from blood anticoagulated with 0.105M (3.2%) buffered citrate solution (24.7 mg/ml $Na_3$citrate.$2H_2O$ and 4.42 mg/ml citric acid.$1H_2O$) at a volume ratio of 1 to 9 and centrifuged at 150× g for 25 minutes. The platelet rich plasma was aliquoted into three 500 μl volumes. One aliquot was treated with phorbol myristate acetate (PMA) at a final concentration of 1.0 μM. The second aliquot was treated with 1.5 mg/ml ristocetin. The third aliquot served as a non-activated control platelet sample. At five minutes, the control and chemically stimulated aliquots were fixed by addition of paraformaldehyde to a 1% final concentration. Control and treated aliquots were diluted to a platelet concentration of $2 \times 10^7$ platelets per ml by the addition of a stock HEPES buffer solution (HBS) (10 mM HEPES, 145 mM NaCl, 5 mM KCl, 0.5 mM NaHPO4, and 1 mM $MgCl_2$) containing 1% paraformaldehyde and allowed to fix at 4° C. for at least 2 hours before labeling.

Monoclonal Antibody Labeling

Samples volumes of 100 μl, containing approximately $2 \times 10^6$ platelets, were pipetted into separate polystyrene tubes and washed twice with HBS containing no paraformaldehyde. Platelets were labeled with Anti-CD42b-FITC (GenTrak, Inc.; Cat.#0027-0648: 2.5 μl/$2 \times 10^6$ platelets), Anti-human von Willebrand Factor (DAKO Corp.; Cat.#M616: 5 μl/$2 \times 10^6$ platelets), Anti-RIBS-1-FITC (gift from Dr. Edward Plow, The Cleveland Clinic Foundation: 5.0 μg/$2 \times 10^6$ platelets), and MSIgG-PE (GenTrak, Inc.; Cat.#0027-0670: 2.5 μl/$2 \times 10^6$ platelets). All samples were two color labeled using CD42-FITC with MSIgG-PE and single color labeled with Anti-RIBS-1-FITC (RIBS1-FITC) and Anti-human yon Willebrand Factor (Anti-vWF) for 30 minutes in the dark. Two color labeling was accomplished by adding the stated concentrations of both MoAbs simultaneously. Single color labeling with Anti-human vWF required a secondary labeling step using a phycoerythrin conjugated F(ab')$_2$ fragment of goat anti-mouse immunoglobulins (DAKO Corp.; Cat.#R480: 2.5 μl/$2 \times 10^6$ platelets). The control and treated samples were subsequently washed twice with HBS containing no paraformaldehyde. The platelets were finally re-suspended in HBS containing 1% paraformaldehyde at a platelet concentration of $2 \times 10^6$ platelets per ml and stored at 4° C. until flow cytometric analysis.

RIBS1 was conjugated with fluorocein-5-isothiocynate (FITC Isomer 1, Molecular Probes, Inc.; #F-143) using the procedure specified by Molecular Probes, Inc. for use with their amine reactive probes. All other monoclonal antibodies, unless otherwise noted, were purchased in the conjugated form.

Flow Cytometry

All samples were analyzed in a Becton-Dickinson FACScan flow cytometer. The FACScan was setup and calibrated as described above. Twenty thousand gated platelet particles, presumed to be single platelets and platelet aggregates, were counted from each sample. A forward versus right angle light scatter gate, determined from CD42 positive platelet events, was used to gate platelet events. Data analysis was performed using WINLIST (Verity Software House, Inc., Topsham, Me.) installed on a 33 MHz 80486DX based microcomputer. The program allows equations to be entered and used as calculated parameters during data analysis. Forward angle light scatter conversion to particle size, fluorescence conversion to MoAb binding, and surface area normalization of MoAb binding measurements yielding MoAb binding density data (bound MoAb molecules per $\mu^2$) were accomplished using the calculated parameter capability of WINLIST software.

Statistical Analysis

Statistical analysis was performed by two-way analysis of variance (ANOVA) of individual histogram means describing MoAb binding densities of control and chemically stimulated platelets. Statistical significance was determined using $\alpha=0.05$. For determination of statistical differences between platelet size categories, the total platelet population ($0.66\ \mu m \leq d \leq 17.96\ \mu m$) was divided into three platelet size categories: 1) small platelets ($0.66\ \mu m \leq d < 1.82\ \mu m$); 2) single platelets ($1.82\ \mu m \leq d \leq 4.38\ \mu m$); and 3) platelet aggregate ($4.38\ \mu m < d \leq 17.96\ \mu m$) where d is the optically determined particle diameter.

Results

Two color labeling of non-activated control platelets with saturating concentrations of CD42-FITC (a MoAb specific for glycoprotein (GP) Ib) and MSIgG-PE (a MoAb with no known antigen, serves as non-specific binding control) resulted in the binding of $2,252 \pm 647$ CD42 molecules per $\mu^2$ and $27 \pm 16$ MSIgG molecules per $\mu^2$. CD42 and MSIgG binding densities did not change significantly (two-way ANOVA, $p>0.05$) following chemical stimulation with either PMA or ristocetin. A typical CD42 binding density distribution for non-activated control platelets is shown in FIG. 12, as analyzed using the optical sizing and SAN techniques of the present invention.

Small platelet particles expressed significantly higher MSIgG binding densities than the other platelet size categories in the non-activated control samples. Similar significant differences in MSIgG binding densities were also observed by size for PMA and ristocetin stimulated platelets. No significant differences in CD42 binding densities were observed by size category for any of the control or chemically stimulated platelet samples tested.

Control platelets labeled with saturating concentrations of Anti-vWF-PE (a MoAb specific for human vWF) resulted in the binding of $8 \pm 2$ Anti-vWF molecules per $\mu^2$. Following stimulation with 1.5 mg/ml ristocetin, Anti-vWF binding density increased significantly (two-way ANOVA, $p<0.05$) to $607 \pm 360$ bound Anti-vWF molecules per $\mu^2$. Anti-vWF binding density did not increased significantly following stimulation with 1.0 $\mu$M PMA. Typical Anti-vWF binding density distributions as well as the corresponding forward angle (FALS) versus right angle (RALS) light scatter plots for control and ristocetin stimulated platelets are shown in FIG. 13, as analyzed using the optical sizing and SAN techniques of the present invention.

Small platelets expressed a significantly higher Anti-vWF binding density compared to the other size categories in the control samples as shown in FIG. 14. FIG. 14 also illustrates that platelet aggregates of ristocetin stimulated platelets express a significantly higher Anti-vWF binding density compared to all other size categories of ristocetin stimulated platelets. The statistical findings indicated in FIG. 14 can be observed in FIG. 13c and FIG. 13d in which color gating of ristocetin stimulated platelets illustrates that the platelet particles with the highest Anti-vWF binding density (shown as red) are clustered in a pattern typical of aggregated platelets. No statistical difference in Anti-vWF binding density was observed between the different size categories of PMA stimulated platelets.

Control platelets labeled with saturating concentrations of RIBS1-FITC (MoAb specific for bound fibrinogen) resulted in the binding of $434 \pm 190$ RIBS1 molecules per $\mu^2$. RIBS1 binding density increased significantly (two-way ANOVA, $p<0.05$) to $1,064 \pm 564$ bound RIBS1 molecules per $\mu^2$ following stimulation with 1.0 $\mu$M PMA. Following stimulation with 1.5 mg/ml ristocetin, RIBS1 binding density also increased significantly (two-way ANOVA, $p<0.05$) to $3,165 \pm 1,255$ bound RIBS1 molecules per $\mu^2$. Typical RIBS1 binding density distributions and the corresponding light scatter plots for control and PMA stimulated platelets are shown in FIG. 15. Statistical analysis of RIBS1 binding densities expressed by size category revealed no significant difference for control or chemically stimulated platelets samples, as illustrated in FIG. 16.

Both control and PMA activated platelets samples demonstrated bimodal RIBS1 binding density distributions (FIG. 15). Bimodal distributions were also observed in Anti-vWF binding density distributions following ristocetin stimulation. Color gating of the small subpopulation of control platelets expressing an elevated RIBS1 binding density (shown as red in FIG. 15a) revealed that these platelets were randomly dispersed throughout the entire platelet population and not the result of platelet aggregates which might have been present. Bimodal distributions for RIBS1 were observed in all non-activated control samples to approximately the same degree and percentage. The expression of bimodal RIBS1 distributions in the PMA stimulated samples varied from donor to donor. Color gating of PMA stimulated platelets exhibiting bimodality revealed that the platelets expressing the highest RIBS1 binding density (shown as red in FIG. 15c) were also randomly dispersed throughout the entire platelet population. In contrast, color gating of the bimodal Anti-vWF binding density distribution in FIG. 13d, observed following ristocetin stimulation, reveals that platelet particles expressing the highest Anti-vWF binding densities (shown as red) are predominantly large platelet aggregates (FIG. 13c).

Discussion

The advantages of quantitative flow cytometry versus other available techniques for quantitation of platelet bound adhesive proteins are evident from the results presented in this study. First, quantitative flow cytometry provides detailed information describing the binding density of adhesive proteins on individual platelets and platelet aggregates. The adhesive protein binding distributions constructed from 20,000 individual platelet events provide an accurate representation of the entire platelet population. Other techniques for bound protein quantitation produce a single bulk averaged value for thousands of platelets. Second, flow cytometry is not limited to a single parameter, rather, it allows multiple parameter data collection for each platelet particle. Quantitative flow cytometry allows detection, analysis, and gating of platelet subpopulations based on any of the multiple parameters collected for each individual platelet particle. Gating and statistical analysis can be performed based on size, light scatter, binding densities, dye concentrations, etc. Additionally, using a flow cytometric data analysis package, such as Winlist, gating and analysis can be extended to use boolean algebra principles. Flow cytometry is presently the only quantitative technique capable of analyzing the quantity of individual platelets needed to construct statistically representative population distributions. Furthermore, flow cytometers are the only instruments capable of providing multiple parameter data for each individual platelet or platelet aggregate analyzed.

The quantitative flow cytometric data analysis presented in this example is limited to: 1) direct analysis of RIBS1 and Anti-vWF binding density distributions for the whole platelet population in response to chemical stimulus (gating=the total platelet population, 0.66 µm≦d≦17.96 µm); 2) direct analysis of platelet subpopulations based on adhesive protein binding density expression in response to chemical stimulus (gating=level of RIBS1 [Anti-vWF] binding density expression AND the total platelet population); and 3) direct analysis of adhesive protein binding density dependency on platelet size (gating=platelet size categories). Due to the sizing limitations of the FACScan, analysis of platelet data was limited to platelet particles with diameters less than 18 µm.

All antibodies used in this study bind with a 1:1 ratio to their antigen. Therefore, the binding density distributions may be interpreted to represent the antigen density distributions. The one exception is Anti-vWF binding, where multiple Anti-vWF molecules may bind to a single vWF multimer. However, the ratio of Anti-vWF molecules binding to a single vWF multimer presumably remains constant, thereby yielding quantitative information.

Quantitative flow cytometry provides accurate, detailed MoAb binding density distributions. The RIBS1 binding densities determined by quantitative flow cytometry for control and 1.0 µM PMA stimulated platelets correspond to 5,449 and 13,370 bound fibrinogen molecules per platelet, respectively, assuming a normal mean platelet surface area of 12.57 µ$^2$. Others report 2,930±1240 bound $^{125}$I-fibrinogen molecules per platelet on non-stimulated, resting platelets. Other studies have reported bound fibrinogen values for ADP or thrombin stimulated platelets ranging from 13,000 to 30,000 fibrinogen molecules per platelet, using radioiodinated fibrinogen or anti-fibrinogen antibodies. Similarly, Anti-vWF binding densities correspond to 100 bound Anti-vWF molecules per non-activated control platelet and 7,629 bound Anti-vWF molecules per ristocetin stimulated platelet which correlate with radioiodinated vWF values of <0.5 µg per 1×10$^8$ resting platelets and 5.6 µg per 1×10$^8$ ristocetin stimulated platelets (1.5 mg/10$^8$ platelets). Binding of Anti-vWF to control platelets was less than measurements of non-specific binding reported by MSIgG binding, which indicates that vWF is not found pre-bound to the surface receptors of resting platelets. Non-specific binding, as reported by MSIgG binding, ranged from 138 to 540 bound MSIgG molecules per platelet with a mean of 339 MSIgG molecules bound per platelet. Additionally, CD42 binding densities did not change significantly as a result of chemical stimulus and corresponded to the expression of 28,308 GP Ib receptors sites on the platelet surface. Flow cytometric quantitation of GP Ib surface expression is also within the range of 15,000 to 28,000 GP Ib receptor sites per platelet determined by radiometric techniques.

Quantitative flow cytometry allows detection of platelet subpopulations which express significantly different binding densities. The bimodal distribution of RIBS1 binding density illustrated in FIG. 15b for control platelets most likely indicates a small degree of platelet activation as a result of venipuncture and platelet rich plasma preparation. However, the control platelet samples may truly be representative of circulating platelets and the bimodality indicative of a circulating platelet subpopulation at a slightly elevated state of activation. Other studies have shown that non-activated resting platelets exist with some level of fibrinogen pre-bound to GP IIb/IIIa.

The degree of bimodality observed in both RIBS1 and Anti-vWF binding densities, illustrated in FIG. 15d for PMA stimulated platelets and FIG. 13d for ristocetin stimulated platelets, represents the percent platelet participation in platelet activation and aggregation in response to stimulus. For example, in FIG. 15d, 41% of the platelet population expressed maximum RIBS1 binding (red population mean= 6412 bound RIBS1 molecules per µ$^2$) following five minutes of PMA stimulation, while the remaining 59% expressed less than maximum fibrinogen binding (blue population mean=584 bound RIBS1 molecules per µ$^2$). Studies have been performed which demonstrate an increase in the percent total platelet population expressing maximum binding density by prolonging the exposure time to the chemical stimulus.

Similar bimodal distributions have been observed for α granule release as detected by GMP-140 expression on the surface of PMA activated platelets. Other flow cytometric platelet activation studies have reported asymmetric participation in activation and aggregation even in response to maximum chemical stimulus (8).

Statistical analysis of adhesive protein binding as a function of platelet size category illustrates another advantage of quantitative flow cytometry. This study reveals that the binding density of vWF to ristocetin stimulated platelet aggregates is significantly higher than all other platelet size categories. Conversely, fibrinogen binding density does not vary with platelet size. Statistical analysis of CD42 and MSIgG binding densities by size category has been described in detail elsewhere. Analysis of size dependency is only possible with quantitative flow cytometry.

In conclusion, quantitative flow cytometry offers many advantages over other generally accepted methods for quantitation of adhesive protein binding. Quantitative flow cytometry, as described here, is presently the only method available to quantify binding of adhesive proteins to single platelets and platelet aggregates in the quantities needed to perform statistical comparisons. Quantitative results obtained by methods such as ELISA, RIA, Southern Blot, and other electrophoresis techniques report a single, bulk averaged value for adhesive protein binding. A single bulk averaged value may not accurately describe binding for all platelets and platelet subpopulations. Though microscopy techniques can provide quantitative binding results for single platelets and platelet aggregates, the major disadvantage is the time required to analyze the number of platelet particles needed to describe a statistically representative population. Quantitative flow cytometry, on the other hand, allows multiple parameter analysis at a rate of several thousand platelet events per second. Furthermore, once data collection is complete, gating schemes can be easily employed allowing detailed population analysis in accordance with the methods described herein.

Quantitative flow cytometry also provides the means to study binding of adhesive proteins without the need for competitive inhibitors and blockers. The use of blockers and inhibitors at saturating concentrations can have unknown effects and produce artifacts, such as steric hinderance, which complicate interpretation of subsequent platelet activation mechanisms. This method provides an attractive alternative to isolating and re-suspending platelets in buffers or plasma preparations containing radiolabeled proteins and analogs. Less platelet preparation is required. It is also possible to perform the platelet studies in whole blood.

Quantitative flow cytometry as described in the present invention is not limited to platelet studies and adhesive protein binding quantitation. Other exciting possibilities exist in which multi-parameter quantitation of single cells can provide improved characterization and understanding of cellular processes. Quantitative flow cytometry also provides an excellent alternative method for evaluating new pharmaceutical prototypes, drug therapy, and monitoring hemopoietic diseases.

EXAMPLE 3

FLOW CYTOMETRIC INVESTIGATION OF SHEAR INDUCED PLATELET ACTIVATION

Introduction

Flow cytometry is used routinely in clinical practice to identify and discriminate between cell populations based on differences in surface receptor expression, DNA content, and light scatter profiles. Flow cytometric investigations have provided valuable information regarding platelet physiology and cellular interactions. The quantitative flow cytometric techniques of the present invention improve analysis and interpretation of flow cytometric data describing platelet activation and receptor-ligand interaction by removing the size dependency of fluorescence measurements. Quantitation of adhesive protein binding densities, receptor availability, and activation specific antigen expression by quantitative flow cytometry has been demonstrated previously.

Quantitative flow cytometry provides an excellent investigative tool to study the molecular basis and mechanism of shear induced platelet activation (SIPAC). SIPAC has been implicated as a major contributor to the development and growth of atherosclerotic lesions and is partially responsible for the thrombotic complications observed during open heart surgery and following implantation of artificial vascular prosthesis. SIPAC may also contribute significantly to the rapid restenosis following balloon angioplasty.

Most recently, SIPAC studies have concentrated on the binding of fibrinogen and von Willebrand Factor under conditions of low and high shear rates. These studies have inferred preferential binding based on shear studies in the presence of blockers and competitive inhibitors to adhesive protein binding. However, inherent problems associated with the use of blockers and inhibitors have not been fully investigated or ruled out. Steric hinderance of nearby receptors or modification of membrane stability and receptor mobility can easily be misinterpreted as being the consequence of adhesive protein blockage. These compounds may, therefore, inhibit or block SIPAC by an unrelated indirect mechanism. Considering these possible complications, it is surprising that the roles of fibrinogen and von Willebrand Factor have not been directly quantified by available radiometric or fluorescent techniques.

In view of the uncertainties associated with ascertaining the roles of fibrinogen and vWF binding based on inhibitors, this example focused on the direct quantitation of fibrinogen and vWF binding in response to pure, uniform, controlled shear stress exposure. Quantitative flow cytometry provides a unique investigative tool to directly quantify the roles of these two adhesive proteins in response to graded shear stress exposure. Additional quantitative flow cytometric assay were performed to investigate shear induced modification of glycoprotein (GP) IIb/IIIa and GP Ib availability as well as cytoplasmic membrane expression of GMP-140, a α granule membrane protein indicating α granule release.

Traditional bulk fluid measurements of free intracellular $Ca^{2+}$ concentration ($[Ca^{2+}]_i$), dense granule release, lysis, and aggregation were also performed and correlated with flow cytometric results. These results provide additional information to aid in the elucidation of SIPAC mechanisms and underline the possible importance of direct activation of GP IIb/IIIa as the initial activation step.

Materials and Methods

Biological Cell Preparation

Platelets were obtained by venipuncture from normal individuals. All donors were self-reported to be medication-free within two weeks prior to donating blood. All platelet samples were characterized on the Becton Dickinson FACScan flow cytometer within 5 days of venipuncture and labeling.

Platelet rich plasma (PRP) was aspirated from blood anticoagulated with 0.105M (3.2%) buffered citrate solution (24.7 mg/ml $Na_3$citrate.$2H_2O$ and 4.42 mg/ml citric acid.$1H_2O$) at a volume ratio of 1 to 9 and centrifuged at 150× g for 25 minutes. In all high shear stress studies, PRP was obtained from blood anticoagulated with 3.8% buffered citrate solution at the same volume ratio. The PRP was incubated simultaneously with 2.5 µM indo-1/AM (Molecular Probes, Inc.: Cat. #I-1223) and 100 nCi tritiated serotonin ($^3$H-HT) (New England Nuclear: Cat. #NET-498) per ml PRP for 90 minutes at room temperature in the dark. Following this incubation time, shear and chemical activation studies were performed.

Shear Induced Platelet Activation

Appropriate volumes of PRP were exposed for 60 seconds to graded levels of continuous, uniform shear stress in a cone and plate viscometer. A 10 cm 0.99° stainless steel cone was used for low shear rate experiments (0 $s^{-1}$, 1,396 $s^{-1}$, and 2,770 $s^{-1}$). A 10 cm 0.33° stainless steel cone was used for high shear rate experiments (5,293 $s^{-1}$ and 8,387 $s^{-1}$). These shear rates correspond to shear stresses of 0 dynes/$cm^2$, 16.7 dynes/$cm^2$, 33.2 dynes/$cm^2$, 63.5 dynes/$cm^2$, and 100.6 dynes/$cm^2$, respectively, assuming a PRP viscosity of 1.2 centipoise. The platen was modified to allow attachment of a trifurcated optic cable connected to a fluorometer. This modification allows continuous monitoring of platelet free intracellular $Ca^{2+}$ concentration during shear exposure by the indo-$1^{5-}$ fluorescence technique. All platelet contact surfaces were treated with Prosil 28 (PCR Inc., Gainesville, Fla.) the day before experiments and allowed to air dry overnight. All surfaces were thoroughly cleaned and retreated with poly(ethylene oxide) between each shear exposure. Treatment with Prosil 28 and poly(ethylene oxide) prevents platelet surface activation.

Immediately following the 60 second shear exposure, sheared PRP aliquots were pipetted from the cone for platelet size distribution and aggregation, dense granule release, lysis, and flow cytometric assays. All aliquots were pipetted directly into polyethylene sample tubes containing paraformaldehyde (1% V/V final concentration) at 4° C. to prevent further platelet activation and preserve the platelet size distribution. Aliquots for lysis determination were not paraformaldehyde treated due to observed degradation of LDH assay performance. Aliquots to be labeled and analyzed by flow cytometry were diluted to 2.0×$10^7$ platelets per ml by addition of stock HEPES buffer solution (HBS) (10 mM HEPES, 145 mM NaCl, 5 mM KCl, 0.5 mM $NaHPO_4$, and 1 mM $MgCl_2$) containing 1% paraformaldehyde and incubated at 4° C. for at least 2 hours before labeling.

Chemically Induced Platelet Activation

Three samples of PRP (500 µl each) were treated with chemical agonists. One aliquot was treated with phorbol myristate acetate (PMA) (Sigma Chemical Company: Cat. #P-8139) at a final concentration of 1.0 µM. The second aliquot was treated with 1.5 mg/ml ristocetin (Sigma Diagnostics: Cat. #885-7). The third aliquot served as a non-activated control platelet sample. At 5 minutes, the control and chemically stimulated aliquots were fixed by addition of paraformaldehyde to a 1% final concentration. Samples from each aliquot were retained to assay dense granule release and platelet aggregation. The remaining control and treated aliquots were diluted to a platelet concentration of $2 \times 10^7$ platelets per ml by the addition of a stock HBS containing 1% paraformaldehyde and incubated at 4° C. for at least 2 hours before labeling.

Monoclonal Antibody Labeling

Samples volumes of 100 µl, containing approximately $2 \times 10^6$ platelets, were pipetted into separate polystyrene tubes and washed twice with HBS containing no paraformaldehyde. Platelets were labeled with the following commercially available monoclonal antibodies: Anti-CD41-FITC (GenTrak, Inc., Plymouth Meeting, Pa.; Cat.#0027-0649: 2.5 µl/$2 \times 10^6$ platelets) directed against glycoprotein (GP) IIb/IIIa; Anti-CD42b-FITC (GenTrak, Inc.; Cat.#0027-0648: 2.5 µl/$2 \times 10^6$ platelets) directed against GP Ib; CD62-PE (Becton Dickinson Immunocytometry Systems, San Jose, Calif.; Cat.#348107: 5.0 µl/$2 \times 10^6$ platelets) directed against GMP-140, a α granule membrane protein; MSIgG-PE (GenTrak, Inc.; Cat.#0027-0670: 2.5 µl/$2 \times 10^6$ platelets); and Anti-human von Willebrand Factor (DAKO Corp., Carpinteria, Calif.; Cat.#M616: 5 µl/$2 \times 10^6$ platelets). Platelets were also labeled with Anti-RIBS-1-FITC at a concentration of 5.0 µg/$2 \times 10^6$ platelets.

Anti-RIBS-1 (RIBS1) is directed against a receptor induced binding site on bound fibrinogen and has been described elsewhere (40). RIBS1 was conjugated with fluorocein-5-isothiocynate (FITC Isomer 1, Molecular Probes, Inc.; #F-143) using the procedure specified by Molecular Probes, Inc. for use with their amine reactive probes. All other monoclonal antibodies, unless otherwise noted, were purchased in the conjugated form.

All control, sheared, and chemically stimulated platelet samples were either two color labeled or single color labeled. Two color labeling was performed using CD42-FITC with MSIgG-PE and CD41-FITC with CD62-PE. Single color labeling was performed with RIBS1-FITC and Anti-human von Willebrand Factor (Anti-vWF). Labeling was achieved by incubation for 30 minutes in the dark. Two color labeling was accomplished by adding the stated concentrations of both MoAbs simultaneously. Single color labeling with Anti-human vWF required a secondary labeling step using a phycoerythrin conjugated F(ab')$_2$ fragment of goat anti-mouse immunoglobulins (DAKO Corp.; Cat.#R480: 2.5 µl/$2 \times 10^6$ platelets). All samples were subsequently washed twice with HBS containing 1% paraformaldehyde following incubation. The platelets were finally re-suspended in HBS containing 1% paraformaldehyde at a platelet concentration of $2 \times 10^6$ platelets per ml and stored at 4° C. until flow cytometric analysis.

Flow Cytometry

All samples were analyzed in a Becton-Dickinson FACScan flow cytometer. The FACScan was formatted for two-color analysis with the light scatter and fluorescence channels set at logarithmic gain using 1024 channels and a four decade scale. The FACScan used a 15 milliwatt air cooled laser producing a single line excitation output at 488 nm. Listmode data was acquired using LYSIS II software running on a Hewlett-Packard Model 340 computer. Light scatter and fluorescence channels were standardized each day using QC3 841 beads (Flow Cytometry Standards Corporation, Research Triangle Park, N.C.), a dual-color reference standard of known size and fluorescence. Amplifier settings were adjusted for optimal measurement sensitivity and reproducibility.

Twenty thousand CD41 or CD42 positive platelet particles, presumed to be single platelets and platelet aggregates, were counted from each sample. A forward versus right angle light scatter gate, determined from CD42 positive platelet events, was used to gate 20,000 platelet events single color labeled with RIBS-FITC or Anti-vWF-PE.

Data analysis was performed using WINLIST (Verity Software House, Inc., Topsham, Me.) installed on a 33 MHz 80486DX based microcomputer. The program allows equations to be entered and used as calculated parameters during data analysis. Forward angle light scatter conversion to particle size, fluorescence conversion to MoAb binding, and surface area normalization of MoAb binding measurements yielding MoAb binding density data (bound MoAb molecules per $\mu^2$) were accomplished using the calculated parameter capability of WINLIST software.

Other Platelet Assays

Platelet lysis was determined by assay of LDH in the platelet free supernate of control and sheared PRP samples using a β-NADH kit (Sigma Diagnostics: Cat. #340-2). Percent dense granule release was determined by comparing the paired tritium decay rates of platelet pellets and supernate from sheared and chemically stimulated platelet samples with measurements made on control and lysed samples. Complete lysis was achieved by sonication with 0.1% Triton X-100 for 10 seconds in an ultrasonic homogenizer (Cole Parmer; 4710 Series).

The platelet size distribution was measured on an electronic particle counter (Elzone PC-285; Particle Dam, Inc.) for all control, sheared and chemically stimulated platelets. PRP samples were diluted 10:20,000 in 20 ml of isotonic saline solution containing 0.25% glutaraldehyde. Size distributions were measured in triplicate from duplicate samples and averaged. A single platelet size range was determined centered about the mode which contained 90% of the total platelet count for non-activated control samples. Platelets contained within this size range are presumed to be single platelets. The percent total platelet count and percent total platelet volume from platelets contained in the single platelet size range was determined for each sample. Two separate calculations of platelet aggregation were made. The percent platelet aggregation of sheared and chemically stimulated platelets was determined by calculating the change in percent total platelet count and percent total platelet volume compared to the control samples. The total platelet volume measured for control, sheared, and chemically stimulated platelets were all within 2% of each other. Constant total platelet volume suggest that exclusion of large platelets outside the sizing window of the counter was not significant.

The two methods used to assess platelet aggregation were calculated to demonstrate that the loss of single platelet volume is more sensitive to the initial stages of small aggregate formation than calculations based on the decrease in total platelet count. Though both methods describe platelet aggregation, volume calculations correlate best with percent aggregation measurements determined by light transmittance measurements for chemically stimulated platelets in aggregometers.

Statistical Analysis

Statistical analysis was performed by two-way analysis of variance (ANOVA) of individual histogram means describing MoAb binding densities of control, sheared, and chemically stimulated platelets. Statistical significance was determined using $\alpha=0.05$. If the means were determined to be statistically different, multiple comparison by test pairs were performed using Student-Newman-Keuls test. Probability values (p) less than 0.05 were considered to be significant.

For determination of statistical differences between platelet size categories, the total platelet population (0.66 $\mu m \leq d \leq 17.96$ $\mu m$) was divided into three platelet size categories: 1) small platelets (0.66 $\mu m \leq d < 1.82$ $\mu m$); 2) single platelets (1.82 $\mu m \leq d \leq 4.38$ $\mu m$); and 3) platelet aggregates (4.38 $\mu m < d \leq 17.96$ $\mu m$) where d is the optical particle diameter (25–27). The mean histogram binding densities by size category were also statistically analyzed using two-way ANOVA.

Results

Flow Cytometric Analysis was observed between the controls anticoagulated with 0.32% sodium citrate and controls anticoagulated with 0.38% sodium citrate, the results suggest that lowered extracellular $Ca^{2+}$ concentrations reduce RIBS1 binding densities on control and chemically stimulated platelets equally.

Due to these changes in anticoagulant concentration, statistical comparison of RIBS1 binding between low and high shear samples is not valid. The data can provide qualitative information if the binding densities of control samples are used to normalize all other binding densities. Comparison of normalized RIBS1 binding densities for control, sheared, and chemically stimulated platelet samples are presented in FIG. 19.

Bimodal RIBS1 binding density distributions were observed in all control samples and most sheared samples. Typical RIBS1 binding density distributions observed for control platelets

TABLE 7

Summary of RIBS1 Binding Densities by Experiment

| | Low Shear Regime Bound RIBS1 Molecules per $\mu^2$ | | | | High Shear Regime Bound RIBS1 Molecules per $\mu^2$ | | |
|---|---|---|---|---|---|---|---|
| # | Control | 0 s$^{-1}$ | 1,396 s$^{-1}$ | 2,770 s$^{-1}$ # | Control | 5,293 s$^{-1}$ | 8,387 s$^{-1}$ |
| 1 | 649.3 | 618.9 | 727.2 | 636.6   1 | 398.2 | 772.5 | 1,069.1 |
| 2 | 609.9 | 624.4 | 655.3 | 667.1   2 | 262.2 | 413.0 | 612.7 |
| 3 | 809.4 | 502.2 | 1,021.0 | 994.2   3 | 314.2 | 616.8 | 654.7 |
| 4 | 340.3 | 450.5 | 629.9 | 571.8   4 | 734.8 | 622.9 | 668.1 |
| 5 | 455.0 | 654.7 | 859.2 | 751.0   5 | 264.1 | 519.9 | 1,043.7 |
| | | | | 6 | 324.7 | 662.1 | 638.0 |
| $\bar{x}=$ | 572.8 | 570.1 | 778.5[a] | 724.1[a]   $\bar{x}=$ | 383.0 | 601.2[a] | 781.0[a] |
| $\sigma'=$ | 181.1 | 88.6 | 162.1 | 164.2   $\sigma'=$ | 179.3 | 123.1 | 214.2 |

Binding density values indicated are the histogram means calculated from individual binding density distributions. The means and standard deviations of each column are designated as $\bar{x}$ and $\sigma'$, respectively. PRP anticoagulated with 0.32% sodium citrate was used in low shear regime experiments, while 0.38% sodium citrate was used in the high regime experiments. Statistical analysis was performed by two-way ANOVA using the individual histogram means. "[a]" indicates that the sample treatment as a group was determined to be significantly different (two-way ANOVA, p < 0.05) than the shear regime control group and other sample treatment groups.

Platelet GP IIb/IIIa and GP Ib cytoplasmic membrane receptor concentrations, as reported by CD41 and CD42 binding densities, did not change significantly following either 60 second shear exposure or chemically stimulation. Control platelets labeled with saturating concentrations of CD41 and CD42 resulted in the binding of 4,815 CD41 molecules per $\mu^2$ and 2,252±647 CD42 molecules per $\mu^2$. CD41 and CD42 binding densities for control, sheared, and chemically stimulated platelets are shown in FIGS. 17 and 18, respectively. Statistical analysis of CD41 and CD42 binding densities by platelet size categories also revealed no significant differences.

RIBS1 binding density increased significantly (two-way ANOVA, p<0.05) following all shear exposures compared to control binding densities. Quantified RIBS1 binding for each sample exposed to low and high shear rates are summarized in Table 7. Although no significant difference and platelets exposed to a shear rate of 8,387 s$^{-1}$ are shown in FIG. 20. Shear exposure induces an asymmetric shift in the RIBS1 binding density distribution with an increase in the percent total platelets contained in the subpopulation expressing the highest binding densities. Statistical analysis by platelet size category indicates that the bimodality is not a function of platelet size. Color gating has been applied in FIG. 20 to illustrate that the platelet subpopulation expressing the highest binding density (gated as red) was randomly distributed throughout the entire platelet population.

No significant differences in mean Anti-vWF binding densities were observed between control samples and samples sheared at 0 s$^{-1}$, 1,396 s$^{-1}$, 2,770 s$^{-1}$, or 5,293 s$^{-1}$. Shear exposure at 8,387 s$^{-1}$ induced a significant increase in the mean Anti-vWF binding densities quantified for 3 out of 6 experiments compared to the corresponding control samples, as shown in Table 8.

TABLE 8

Summary of Anti-vWF Binding Densities by Experiment

| # | Low Shear Regime Bound Anti-vWF Molecules per μ² | | | | # | High Shear Regime Bound Anti-vWF Molecules per μ² | | |
|---|---|---|---|---|---|---|---|---|
| | Control | 0 s⁻¹ | 1,396 s⁻¹ | 2,770 s⁻¹ | | Control | 5,293 s⁻¹ | 8,387 s⁻¹ |
| 1 | 10.8 | 15.3 | 13.6 | 13.8 | 1 | 5.3 | 9.6 | 31.3ᵃ |
| | | 4Y | | | | | | |
| | | | 6.9 | | | | | |
| 2 | 6.1 | | 6.5 | 6.2 | 2 | 6.6 | 7.8 | 10.8 |
| 3 | 9.9 | 9.7 | 11.5 | 11.3 | 3 | 10.4 | 11.1 | 14.0 |
| 4 | 8.2 | 8.6 | 10.2 | 9.1 | 4 | 10.5 | 10.9 | 13.6 |
| 5 | 8.6 | 8.6 | 10.5 | 10.9 | 5 | 6.5 | 14.0 | 33.3ᵃ |
| | | | | | 6 | 10.0 | 16.6 | 34.2ᵃ |
| x̄ = | 8.7 | 9.8 | 10.5 | 10.2 | x̄ = | 8.2 | 11.7 | 22.9ᵃ |
| σ' = | 1.8 | 3.2 | 2.6 | 2.8 | σ' = | 2.3 | 3.2 | 11.1 |

Binding density values indicated are the histogram means calculated from individual binding density distributions. The means and standard deviations of each column are designated as x̄ and σ', respectively. PRP anticoagulated with 0.32% sodium citrate was used in low shear regime experiments, while 0.38% sodium citrate was used in the high regime experiments. Statistical analysis was performed by two-way ANOVA using the individual histogram means. "ᵃ" indicates that the binding density value was determined to be significantly different (two-way ANOVA, $p < 0.05$) than its corresponding control. "ᵇ" indicates that the sample treatment as a group was determined to be significantly different (two-way ANOVA, $p < 0.05$) than the shear regime control group and other sample treatment groups.

FIG. 21 illustrates the mean Anti-vWF binding densities observed for control, sheared, and chemically stimulated platelets.

Bimodal Anti-vWF binding density distributions were observed in the 3 experiments at 8,387 s⁻¹ demonstrating significant binding of vWF. Color gating of one experiment, shown in FIG. 22, confirms statistical findings that large platelet aggregates, resulting from this high shear rate, express significantly greater Anti-vWF binding densities. Similar statistical findings were observed in ristocetin stimulated platelet samples.

Significant expression of GMP-140 on the cytoplasmic membrane, as reported by CD62 binding density, was only observed in platelet samples exposed to a shear rate of 8,387 s⁻¹. Interestingly, the same 3 experiments which demonstrated significantly elevated mean Anti-vWF binding densities also expressed significantly elevated mean CD62 binding densities. The three other 8,387 s⁻¹ platelet samples only expressed slightly elevated mean CD62 binding densities compared to corresponding controls. All other shear rates failed to induce any significant changes in CD62 binding densities compared to controls. The mean CD62 binding densities of control, sheared and chemically stimulated platelets are illustrated in FIG. 23.

Bimodal CD62 binding density distributions were also observed in samples sheared at 8,387 s⁻¹ and in some PMA stimulated platelet samples. Opposite to the platelet size dependency observed for Anti-vWF expression, statistical analysis of CD62 binding density distributions measured for the three 8,387 s⁻¹ samples expressing elevated binding densities showed no significant platelet size dependence. Platelets expressing elevated CD62 binding densities were randomly distributed throughout the entire platelet population. The randomness of CD62 positive platelets closely resembled that of RIBS1 positive platelets shown in FIG. 20.

The binding densities of all MoAbs tested showed no significant differences between samples exposed to the cone and plate in the absence of shear (0 s⁻¹ samples) and the corresponding non-activated controls. The 0 s⁻¹ samples serves as surface activation controls.

Quantitation of non-specific binding, reported by MSIgG binding density measurements, indicates very low level non-specific binding in all platelet samples tested. Furthermore, MSIgG binding densities did not change significantly in response to shear or chemical stimulation. Mean MSIgG binding densities ranged from 19 to 32 bound MSIgG molecules per μ² with an average histogram mean expression of 26.4±12.4 (mean±std) bound MSIgG molecules per μ².

Traditional Platelet Assays

Percent platelet aggregation was determined by two separate methods. The first method calculates percent aggregation based on the reduction in single platelet counts, while the second method is based on the reduction in single platelet volume. The total platelet volume was preserved after stimulation, suggesting that the reduction of small platelet volume was redistributed to other measurable particle sizes. Formation of large platelet particles accompanied by a reduction in the volume of single platelet sized particles is interpreted to be aggregation. The mean percent platelet aggregation resulting from shear exposure is summarized in FIG. 24. Both methods report significant platelet aggregation in response to all shear rates investigated. However, the method based on the loss of single platelet volume has greater sensitivity to small aggregate formation.

Both methods of calculating platelet aggregation were also used to calculate the percent aggregation of chemically stimulated platelet samples. All chemically stimulated PRP samples were obtained by addition of PMA or ristocetin while in a standard light transmittance aggregometer (Chrono-Log Corporation, model 400-VS). Traces of light transmittance obtained during PMA and ristocetin stimulus corresponded to 56%±11% and 68%±8% platelet aggregation, respectively. Corresponding measurements made in the electronic particle counter using loss in single platelet count resulted in the calculation of 13.7%±6.2% and 19.8%±4.2% platelet aggregation for PMA and ristocetin stimulated platelets, respectively. Calculations based on loss of single platelet volume resulted in percent platelet aggregation values of 49.6%±10.0% and 58.0%±5.9% for PMA and ristocetin samples, respectively.

Quantitation of platelet free intracellular $Ca^{2+}$ concentration measured continuously during shear exposure demonstrated significant increases in PRP samples sheared at 5,293

$s^{-1}$ and 8,387 $s^{-1}$. In these high shear experiments, significant increases in $[Ca^{2+}]_i$ were observed following a 30 second time delay from the onset of shear exposure. The $[Ca^{2+}]_i$ measured during the first 30 seconds of high shear exposure and during the entire 60 seconds at all other shear rates remained with in the homeostatic baseline levels of approximately 105±21 nM. During the last 30 seconds of high shear exposure, $[Ca^{2+}]_i$ measurements increased linearly from baseline levels to $[Ca^{2+}]_i$ levels ranging from 150 nM to 350 nM.

Thermodynamic and chemical equilibrium calculations suggest that the extracellular $Ca^{2+}$ concentration of sodium titrated plasma is approximately 260 nM. Calcium ionophore studies, using A23187, demonstrated that the maximum obtainable $[Ca^{2+}]_i$ was in the range of 300 nM to 500 nM with an average of 369±87 nM. The results of these calcium ionophore studies suggest that intracellular stores of $Ca^{2+}$ are released, since $[Ca^{2+}]_i$ increased beyond extracellular plasma concentrations. In several 8,387 $s^{-1}$ shear experiments, the $[Ca^{2+}]_i$ was also observed to increase above extracellular plasma concentrations. Interestingly, the 8,387 $s^{-1}$ samples which obtained $[Ca^{2+}]_i$ levels in excess of extracellular concentrations coincided with the samples which expressed significant increases in CD62 and Anti-vWF binding densities quantified by flow cytometry.

Dense granule release, assayed by release of tritiated serotonin, was determined to be significant in platelet samples sheared at rates above 2,770 $s^{-1}$. Percent dense granule release was calculated to be 1.57±0.65% at 5,293 $s^{-1}$ and 4.53±2.7% at 8,387 $s^{-1}$. Dense granule release at all other shear rates was not different from control samples.

Platelet lysis was not observed as a result of shear exposure. The total platelet LDH activity was 649±45 LDH units per ml obtained from sonicated PRP containing $3 \times 10^5$ platelets per µl. The platelet free plasma LDH activity was 145±27 LDH units per µl for control samples. No significant difference in platelet free plasma LDH activity was observed between sheared and control samples. Therefore, platelet activation measured in response to shear exposure is the direct result of shear and not an indirect consequence of released agonist from lysed platelets.

Discussion

Four significant observations can be made based on the results of this example. First, fibrinogen is the primary adhesive protein bound to platelets following all shear rates investigated. Second, contradictory to the conclusions based on inhibitor studies, vWF binding was only observed at extremely elevated shear rates. The binding density data of Anti-vWF and CD62 suggest that platelet endogenous vWF is the source of vWF bound at high shear rates. The data also suggest that the main role of vWF is to stabilize large aggregate formation. Third, $[Ca^{2+}]_i$ measurements demonstrate conclusively that increases in $[Ca^{2+}]_i$ are not an absolute requirement for SIPAC. Fourth, the results suggests that the mechanism of shear induced platelet activation and aggregation involves fibrinogen binding to activated GP IIb/IIIa independent of $[Ca^{2+}]_i$ increases.

All antibodies used in example bind with a 1:1 ratio to their antigen. Therefore, the binding density distributions may be interpreted to represent the antigen density distributions. The exception being Anti-vWF binding, where multiple Anti-vWF molecules may bind to a single vWF multimer. However, the ratio of Anti-vWF molecules binding to a single vWF multimer should remain constant, thereby yielding quantitative information.

Flow cytometric quantitation of fibrinogen and vWF binding provides direct evidence that fibrinogen is the predominant adhesive protein which binds to platelets as a result of shear exposure. RIBS1 binding densities increased significantly from unsheared control values following all shear rates tested (FIG. 19). Conversely, no significant increases in Anti-vWF binding densities were observed for shear rates below 8,387 $s^{-1}$ (FIG. 21). Analysis of Table 8 reveals that only 50% of the experiments conducted at 8,387 $s^{-1}$ expressed significant increases in Anti-vWF binding densities. These results are consistent with a hypothesis in which fibrinogen forms the primary adhesive bridge supporting platelet aggregation in both low and high shear regimes. The binding of Anti-vWF predominantly to large platelet aggregates suggests that vWF binding is a secondary aggregation response. Binding of vWF presumably provides the additional adhesive support required to hold large aggregates together in the presence of elevated fluid forces.

Quantitation of significant cytoplasmic GMP-140 expression, reported by CD62 (FIG. 23), directly corresponds to increases in Anti-vWF binding densities (FIG. 21). Plasma vWF is present in the soluble multimeric form and must be bound to a surface before expressing the specific ligand structure recognized by the GP Ib binding site. Previous SIPAC studies indicate that soluble plasma vWF binds spontaneously to both GP IIb/IIIa and GP Ib by an unknown mechanism proceeding other platelet activation indices such as increased $[Ca^{2+}]_i$. α granule release at 8,387 $s^{-1}$ provides an explanation for spontaneous vWF binding in the absence of any thrombogenic surfaces. Platelet endogenous vWF possesses ristocetin cofactor activity, exists already in the insoluble multimeric form, and binds spontaneously to GP IIb/IIIa after α granule release. The coupling of α granule release and vWF binding suggests that the source of vWF binding to platelets in PRP exposed to shear rates of 8,387 $s^{-1}$ is endogenous vWF released from α granules. Once bound, platelet endogenous vWF can mediate platelet-platelet aggregation.

The most important observation is that significant platelet aggregation supported by bound fibrinogen occurs in the absence of increased $[Ca^{2+}]_i$. Continuous measurement of $[Ca^{2+}]_i$ during 60 second PRP exposure to low shear rates reveals no significant changes in $[Ca^{2+}]_i$. At high shear rates significant increases in $[Ca^{2+}]_i$ were observed following a 30 second delay from the onset of shear exposure. Direct analysis of $[Ca^{2+}]_i$ levels measured during exposure to 8,387 $s^{-1}$ reveals that the same samples expressing significant increases in both CD62 and Anti-vWF binding densities also exhibited $[Ca^{2+}]_i$ levels above extracellular concentrations. These findings indicate that α granule release and binding of platelet endogenous vWF during shear exposure may be directly related to the release of $Ca^{2+}$ from intracellular stores.

Shear induced platelet activation and aggregation occurred without any significant dense granule release during low shear exposure. The percent dense granule release measured during high shear exposures was significant and presumably related to increases in $[Ca^{2+}]_i$. Furthermore, no measurable platelet lysis was observed in response to the shear rates investigated. These observations indicate that binding of fibrinogen and the resulting platelet aggregation were the direct result of shear exposure and not the presence of platelet agonist resulting from release or lysis.

Analysis of bimodal binding distributions measured by quantitative flow cytometry of the present invention yields further insight into the mechanism of SIPAC. The bimodal distributions quantified for RIBS1 and CD62 demonstrated random platelet activation throughout the entire platelet population. No platelet size subpopulations were more susceptible to the initial steps of SIPAC. Secondary aggregation was a strong function of platelet size as demonstrated by vWF binding predominantly to large platelet aggregates.

The absence of measurable $[Ca^{2+}]_i$ increases during the first 60 seconds of most shear exposures described demonstrates that increased $[Ca^{2+}]_i$ is not an absolute requirement of SIPAC. One other study has made similar observations for $[Ca^{2+}]_i$ response during shear. Prior to this study, it was believed that increased $[Ca^{2+}]_i$ triggered the initial activation response responsible for SIPAC.

The lack of significant $[Ca^{2+}]_i$ increases during low shear rate exposure is most likely related to the artificially lowered extracellular $Ca^{2+}$ concentration present in citrated plasma. At low shear rates, the rate of $Ca^{2+}$ influx across the platelet membrane or by release of intracellular $Ca^{2+}$ reserves does not exceed the rate which platelets can actively sequester or pump out. At high shear rates, the rate of $Ca^{2+}$ influx eventually exceeds the platelet ability to regulate $[Ca^{2+}]_i$ and the $[Ca^{2+}]_i$ begins to increase. The data also demonstrates that intracellular stores are released during high shear exposure since the $[Ca^{2+}]_i$ exceeds extracellular $Ca^{2+}$ concentrations. Even though the extracellular $Ca^{2+}$ concentration of citrated plasma is significantly reduced, previous SIPAC studies have demonstrated no statistical differences between the results obtained from PRP anticoagulated with sodium citrate, hirudin, and heparin.

The absence of bound vWF in response to shear rates below 8,387 s$^{-1}$ directly demonstrates that vWF is not the primary adhesive protein as other studies have suggested. The results of previous SIPAC inhibitor studies are difficult to interpret due to possible artifacts resulting from the use of inhibitors and blockers. However, the inhibitor data reported in those studies supports flow cytometric observation which suggests that vWF plays a secondary aggregation role and is responsible for the formation and stabilization of large platelet aggregates at very high shear rates. The inhibitor data presented in previous SIPAC studies also provides additional evidence which supports the primary role of fibrinogen as the preferred adhesive protein bound during shear exposure. Studies using monoclonal antibodies such as LJ-CP8 and AP2 have demonstrated complete inhibition of shear induced platelet aggregation at all shear rates by blocking the fibrinogen binding site on GP IIb/IIIa, while blocking GP Ib with other monoclonal antibodies inhibited platelet aggregation at high shear rates.

Previous competitive inhibitor studies lack the direct quantitative fibrinogen and vWF binding results required to verify the conclusions inferred from inhibitor data. Several factors exist which may have complicated the analysis and interpretation of those studies. As stated earlier, steric hinderance of nearby receptors or modification of membrane stability and receptor mobility can easily be misinterpreted as being the direct consequence of adhesive protein blockage. Steric hindrance of collagen and platelet activating factor receptors has been observed during studies describing antibody binding to GP Ib. Another factor which can possibly lead to misinterpretation of inhibitor data is related to the method used to detect platelet aggregation (FIG. 24). This is dramatically demonstrated the study by Alevriadou et al. in which no platelet aggregation was observed for shear stresses as high as 90 dynes/cm$^2$ in the absence of inhibitors.

CONCLUSION

The development of a new quantitative flow cytometric method with direct application for investigation and characterization of biological particles is demonstrated by the foregoing examples. The results demonstrate accurate particle sizing based on the forward angle light scatter measured in a Becton Dickinson FACScan flow cytometer. The method includes introduction of a new quantitative flow cytometric technique based on quantitative fluorescence techniques and surface area or volume normalization provided by an empirically derived size equation. Application of quantitative flow cytometry to the study of platelet antigen densities demonstrates the improved analysis capabilities resulting from decoupling fluorescence measurements and related particle size dependency.

The development of an empirical sizing equation which predicts particle and biological cell sizes based on the forward angle light scatter measured in a flow cytometer demonstrates that the empirical equation predicts particle radii which are within 2.1% of the particle radius measured on a standard electronic particle counter. The percent error associated with sizing biological cells is 12% on average, within the acceptable range associated with most light scatter sizing instrumentation. Using the empirical sizing equation, the FACScan flow cytometer has an effective particle sizing range of 0.33 μm to 8.98 μm in radius. A similar empirical sizing equation can be determined for other flow cytometers using the method described and claimed herein.

The development of a surface area and volume normalization method effectively removes all size dependency from fluorescent measurements made in the flow cytometer. Combining the quantitative fluorescence method with surface area normalization provides a quantitative flow cytometric method allowing measurement of detailed surface antigen binding density distributions which were not obtainable by other quantitative techniques. Quantitative flow cytometry using surface area normalization successfully quantifies cell or particle receptor expression independent of cytometric event size while quantitative flow cytometry provides improved analysis characteristics allowing direct comparison of particles of different sizes. Further, quantitative flow cytometry provides detailed antigen density distribution information based on single cell measurements. Quantitative flow cytometry allows detection of cell subpopulations based on multi-parameter data collection and offers numerous advantages in cell characterization not provided by RIA, ELISA, gel electrophoresis techniques, and other radiometric techniques.

The quantitative flow cytometric technique developed for investigation of platelet activation has direct applications in clinical flow cytometry. Many of the hemopoietic diseases currently screened and characterized in clinical flow laboratories involve cells which vary in size depending on the stage of morphological development and disease progression. Quantitative flow cytometric techniques using size normalization may aid in developing clinical ranges for hemopoietic disorders and standardize reporting. Additionally, the methods described provide exciting possibilities for characterizing and discriminating between aneuploid and diploid DNA content in solid tumors.

Although a preferred embodiment of the method of the present invention relies in part on Fraunhofer Diffraction Theory, other light scatter theories can perform well within their designed range of validity. In order to size at very small particle diameters (<1 μm), it may be necessary to use either Mie theory or Rayleigh-DeBye light scatter theories. Regardless of which light scatter theory is used, the novel step of using such theory to generate a sizing curve and fitting an empirical equation to the theoretical curve would be the same.

SOFTWARE IMPLEMENTATION OF FLOW CYTOMETRIC SIZING AND SURFACE AREA NORMALIZATION METHODS FOR DATA ANALYSIS

The novel methods of flow cytometric sizing, surface area or volume normalization, and absolute cellular quantitation described above can implemented by software imbedded in or associated with the flow cytometer. The use of software to implement these methods would improve reproducability, remove user variability, and decrease processing time compared to manual implementation. Software implementation requires both user steps as well as software routines.

The required steps to be taken by the user are:

A. Setup flow cytometer using the normal procedure established by the laboratory for the biological analysis to be performed.

B. Characterize the sizing parameters of the flow cytometer for the current setup by measuring a set of size calibration beads of known size, shape, refractive index, and fluorescence. The set should include at least 5 different size particles in the range of measurement).

C. Characterize the fluorescence calibration curve for each of the fluorescence detectors to be used by measuring a set of beads labeled with a quantified amounts of mean equivalent soluble fluorescence (MESF) per bead using the same fluorescent molecule as conjugated to the biological markers to be used. The set should include at least 4 quantified MESF levels and a certified blank: i.e. Quantum 1000 beads; Flow Cytometry Standards Corporation, Triangle Park, N.C.).

D. Characterize the fluorescence per protein molecule (F/P ratio) used as a biological marker by measuring the fluorescence of beads containing quantified binding sites per bead labeled separately for each of the fluorescently conjugated biological markers to be used in the biological analysis (i.e. Simply Cellular beads, Flow Cytometry Standards Corporation).

E. Save the size, MESF, and F/P calibration measurements in listmode files.

F. Using the same settings (no adjustments to optics, gains, or amplifiers), measure and save biological cell samples in a listmode file following the protocol as established by the laboratory.

G. Steps B though E should be performed periodically during the day or following any adjustment to the flow cytometer's settings.

The software imbedded in or associated with the flow cytometer should be written in a manner well known in the art to next carry out the above described methods of particle sizing, surface area or volume normalization, and absolute cellular quantitation, as follows:

H. Generate the Sizing Equation Routine by:
1. automatically reading the listmode data file containing the size calibration bead measurements;
2. determining the mean forward angle light scatter (FALS) for each size bead;
3. pairing the measured mean FALS values with either a user entered or program read list of mean particle radii;
4. fitting the theoretical light scatter equation (Fraunhofer Diffraction Theory, Anomalous Diffraction Theory, Mie Theory, Rayleigh-DeBye Theory, Rayleigh-DeBye-Gans Theory or modification of any of these classical light scatter theories) to the measured FALS-radius pairs;
5. using the fitted theoretical equation to generate a FALS-radius curve made up of discrete theoretical FALS-radius pairs using small finite steps in theoretical particle radii. The step size should be at least three orders of magnitude less than the particle radius corresponding to the minimum FALS value for the current setup; i.e. FALS=1;
6. determining the range over which the theoretical FALS-radius curve is continuous and unique, i.e. no anomalous regions;
7. fitting several predetermined forms of empirical equations to the theoretical FALS-radius curve within the unique, continuous range of sizing and determine which of the empirical equations gives the best fit by least squares method;
8. reporting out the theoretical FALS-radius curve with the measured data superimposed, theoretical range of validity, the best empirical fit with its $R^2$ value, and give the user the option to accept, modify or reject the sizing calibration;
9. Once the sizing calibration has been accepted, the program will read in the listmode files one at a time, determining the particle size for each cytometric event measured, and store the radius, equivalent spherical surface area and volume as new cytometric parameters for use in analysis and absolute quantitation calculations. There are two ways in which the program can determine the particle size, surface area and volume. The first is to use the empirical sizing equation to calculate the particle radius for each cytometric event and then calculate the surface area and volume. The second is to generate a look up table before data analysis which maps the corresponding radius, surface area and volume for each of the possible FALS channels #. The second method reduces the program computation time required to analyze each listmode data file.

It is also important to note that solving the empirical equation for each cytometric event measured is most likely not the most time efficient way to implement sizing and size normalization. Instead, once the empirical equation is obtained, the program should calculate the particle size which corresponds to each FALS detector channel (channel #0-1023) and save the resulting data as a look up table or develop a mapping. Using the look up table or mapping, the program will simply look up the particle size which corresponds to the FALS of each cytometric event when the listmode data is open analyzed. This will allow much faster opening of files for analysis and calculation of absolute cellular quantitation.

H. Next, mean equivalent soluble fluorescence (MESF) detector calibrations must be performed (module already available in Winlist; Verity Software House, Topsham, Me.) by:
10. Program reads listmode data files containing the MESF calibration bead data and determines the mean fluorescent channels corresponding to each set of quantified beads which is unique for that detector setting.
11. Reads an information file which contains the quantified MESF/bead data (supplied by the MESF bead manufacturer).
12. Determines the best log linear fit to the data in the form of a straight line on a log-linear plot of MESF/bead vs fluorescent detector channel number collected using log amplification.
13. Applies the MESF Calibration Curve determined for each detector to all subsequent listmode data files thereby calculating the MESF bound to each cytometric event measured.

I. Then, a fluorescence to protein (F/P) ratio calculation is performed by:
1. Program reads the listmode data files containing the measurements of beads of known binding site numbers labeled with saturating concentrations of fluorescently conjugated antibodies.
2. Program calculates the mean MESF value bound per bead and divides by the total number of binding sites per bead which can be entered by the user or read from a data file thereby calculating the mean MESF conjugated per molecule of antibody.
3. Program stores the F/P ratios measured for each of the antibodies used and uses these ratios to calculate the number of antibody molecules bound to each cytometric event contained in the subsequent listmode data files. (Note: This can be modified to determine the F/P ratio of internalized dyes and protein markers)

J. Finally, absolute cellular quantitation is obtained by:
1. Divide the MESF value calculated for a particular cytometric event by the F/P ratio of the corresponding fluorescently conjugated antibody to obtain the number of antibody molecules bound to that particular cytometric event.
2. Divide the result of D.1 by the corresponding event surface area (or volume if working with internalized dyes or proteins) to obtain the number of antibody molecules bound per unit surface area (or number of internalized dye molecules per unit volume).

Absolute cellular quantitation provides results for each cytometric event measured which are independent of the event size, user defined detector settings, detector linearity, and any changes which may occur due to photo-bleaching of the fluorescently conjugated antibody or changes from lot to lot in the antibody production. It also provides a realistic and reproducible method to standardize flow cytometric analysis and reporting in cellular quantitation with a common denominator so that cells of different species or of different lineage can be directly compared. It further provides the ability to track and quantify cellular development from progenitor cells all the way to the mature cell. This may provide additional information by which to predict and distinguish between disease states at earlier stages of development by establishing clinical diagnostic ranges. This should provide information which may be used to predict disease outcome and eventual relapse. This technique should also provide valuable data to monitor drug therapies and predict effectiveness.

SOFTWARE IMPLEMENTATION OF FLOW CYTOMETRIC SIZING AND SURFACE AREA AND VOLUME NORMALIZATION METHODS DURING DATA ACQUISITION AND SORTING

The methods of flow cytometric sizing, surface area or volume normalization, and absolute cellular quantitation can also be implemented by a software program during data acquisition and cell sorting. The use of software to implement these procedures would follow the same steps as outlined above. The primary difference would be the time constraints involved in being able to sort based on one of the size or size normalized parameters. In order to avoid time constraints, it would be necessary to determine the sizing parameters and empirical sizing equation prior to collecting cellular measurements or cell sorting. Once the sizing equation was determined, a look up table or mapping routine could be utilized so that cytometric events could be displayed in a data acquisition window real time. The use of a look up table or mapping routine reduces the number of computational steps down to 4 to six operations (read FALS, look up radius, read radius, display event in radius window) compared to the many steps needed to read the FALS, compute the radius from the empirical equation and then display on screen. Similar operations could be performed which divided a fluorescence channel measurement by the looked up surface area or volume and then displayed the normalized fluorescence on screen. Not only could this be used to acquire data and store the raw and normalized data in listmode files, but it also provides a way to sort based on size or size normalized fluorescence measurements. The key is the use of a look up table for radius, surface area and volume determined before data acquisition and sorting is initiated. The reduced computational steps will allow sorting based on the size and normalized data as well as the raw data.

The required user steps are to:

A. setup the flow cytometer using the normal procedure established by the laboratory for the biological analysis to be performed;

B. characterize the sizing parameters of the flow cytometer for the current setup by measuring a set of size calibration beads of known size, shape, refractive index, and fluorescence (set should include at least 5 different size particles in the range of measurement);

C. save the size calibration measurements in listmode files.

D. initiate program to determine sizing equation, calculate look up table, and develop event mapping, which:
1. automatically reads the listmode data file containing the size calibration bead measurements;
2. determines the mean forward angle light scatter (FALS) for each size bead.
3. pairs the measured mean FALS values with either a user entered or program read list of mean particle radii.
4. fits the theoretical light scatter equation (Fraunhofer Diffraction Theory, Anomalous Diffraction Theory, Mie Theory, Rayleigh-DeBye Theory, Rayleigh-DeBye-Gans Theory or modification of any of these classical light scatter theories) to the measured FALS-radius pairs.
5. uses the fitted theoretical equation to generate a FALS-radius curve made up of discrete theoretical FALS-radius pairs using small finite steps in theoretical particle radii (step size at least three orders of magnitude less than the particle radius corresponding to the minimum FALS value for the current setup; i.e. FALS=1).
6. determines the range over which the theoretical FALS-radius curve is continuous and unique (i.e. no anomalous regions).
7. fits several predetermined forms of empirical equations to the theoretical FALS-radius curve within the unique, continuous range of sizing and determine which of the empirical equations gives the best fit by least squares method.
8. reports out the theoretical FALS-radius curve with the measured data superimposed, theoretical range of validity, the best empirical fit with its $R^2$ value, and give the user the option to accept, modify or reject the sizing calibration.

9. Once the sizing calibration has been accepted, the program will generate a look up table for radius, surface area, and volume for each of the possible FALS channels #. A mapping routine would be initiated to determine the axis scales for selected size and size normalized fluorescence measurements to be displayed during data acquisition and sorting.

Next, the user must create the data display windows and gates to be used during data acquisition and sorting. Using the same settings (no adjustments to optics, gains, or amplifiers), user initiates data acquisition or sorting of biological cell samples based on selected gates (may include boolean algebra logic decisions).

Data (raw, size and size normalized measurements) will be saved in a listmode file following acquisition or sorting for analysis. These steps should be performed periodically during the day or following any adjustment to the flow cytometer's settings.

HARDWARE ADAPTATIONS TO IMPROVE SIZING CHARACTERISTICS

There are several hardware adaptations which can be made to flow cytometer design which will improve sizing characteristics and range of sizing validity when using the methods of the present invention. First, the FALS detection optics can be modified to allow accurate and reproducible changes to the angles of collection. Some flow cytometers are equipped with adjustable blocker bars and collection apertures. However it is difficult to adjust these to obtain the same settings from day to day especially if they must be changed to optimize for different analysis protocols. Second, fitting the flow cytometer with lasers which produce stable multi-line emissions which the output flux can be controlled (351 nm and 488 nm simultaneously). Third, replace the photodiode used to measure FALS with a photomultiplier tube. The photomultiplier tube offers greater sensitivity and range of operation. Fourth, replace the log-linear amplifier used with the photodiode with an amplifier with greater range of amplification. Fifth, allow the user complete freedom to adjust the photomultiplier tube voltage and amplification whether in log or linear amplification.

I. Design New Optics for Use with New Flow Cytometers and Retrofitting Old Flow Cytometers A. Design #1: Optics with Fixed Angles of Collection
    1. Design incorporates a platform which mounts in line (0°) with direction of forward angle light scatter.
    2. The platform's position is field engineer adjustable to allow accurate positioning of the optic lens stage (up-down, side to side, back-front, and tilt) so that it is exactly aligned with the laser path and focal distances.
    3. The optic lens stage is set so that the user can install different cased lens with an optical mask of known $\theta_{min}$ and $\theta_{max}$ or install different optical mask in front of the FALS collection lens.
    4. User could purchase a set of optical mask or set of cased lens with different set angles of collection which the user could install quickly and reproducibly.

B. Design #2: Optics with Independent Adjustment of $\theta_{min}$ and $\theta_{max}$
    1. Design incorporates a platform which mounts in line (0°) with direction of forward angle light scatter.
    2. The platform's position is field engineer adjustable to allow accurate positioning of the optic lens stage (up-down, side to side, back-front, and tilt) so that it is exactly aligned with the laser path and focal distances.
    3. The FALS collection lens is fixed in position inside the optic lens stage.
    4. The platform is fitted with two mask stages which can be positioned independently between the flow cell (open air stream) and the FALS collection lens. The mask stages can be moved forward towards the flow cell to increase the limiting angle or backward towards the FALS collection lens to decrease the limiting angles of collection. The mask stage movement is controlled by course and fine geared track adjustment knobs (separate controls for the minimum and maximum mask stages). Additionally, each mask stage would have a angle indicator to record the angles of collection and allow easy repositioning for future measurements using the same settings.
    a. A $\theta_{min}$ mask stage, adjustable from 0.5° to 5.0°
    b. A $\theta_{max}$ mask stage, adjustable from 5.0° to 30.0°
Note: Min and Max mask of different diameters to allow greater range of limiting angle adjustment (i.e. min mask #1—0.5° to 1.0°; min mask #2—1.0° to 3.0°; min mask #3—2.0° to 5.0°; etc.).

II. Installation of a Controllable, Stable Multiline Laser
  A. The use of two color or three color laser light scatter yields a two to three distinctly different sizing curves (see the four plots).
  B. It is important that the laser lines be focused through the same path so that the same angles of collection are used for both and to maintain proper optical alignment.
  C. Theory predicts that the different curves could be used simultaneously to improve sizing accuracy and extend the range of sizing validity by using one curve when the other enters a region of anomalous behavior.
  D. Additional FALS detectors would need to be installed with no modification to the FALS optics described above, except that dichroic mirrors at the proper angles and wavelength would need to be installed to split the different FALS wavelengths to there respective detectors.

III. Replacement of the FALS Photodiodes with Photomultiplier Tubes and Different Amplifiers Photomultiplier tubes provide greater sensitivity by using internal amplification.
  A. Replacing the amplifiers with amplifiers with a greater range of amplification will further increase the sensitivity and allow the user to focus in on specific ranges of interest.

Thus, although there have been described particular embodiments of the present invention of a new and useful "Method and Apparatus for Determining Particle Size and Surface Area and Volume Normalized Fluorescence Using Forward Angle Light Scatter in Flow Cytometry", it is not intended that such references be construed as limitations upon the scope of this invention except as set forth in the following claims. Further, although there have been described parameters used in the preferred embodiment and examples of use, it is not intended that such be construed as limitations upon the scope of this invention except as set forth in the following claims.

What is claimed is:

1. A method of determining surface and cytoplasmic characteristics of a biological particle using flow cytometry comprising the steps of:
  a. determining, directly from forward angle light scatter intensity information an absolute radius of said particle and measuring a fluorescence intensity of a fluorescent probe associated with said particle while said particle is in a conventional flow cytometer;

b. calculating from said determined absolute particle radius an equivalent spherical surface area corresponding to said particle; and c. determining a surface area normalized fluorescence from a ratio of said fluorescence intensity to said equivalent spherical surface area.

2. The method of claim 1 further comprising the steps of calculating from said measured absolute particle radius an equivalent absolute spherical volume corresponding to said particle and determining a volume normalized fluorescence from a ratio of said fluorescence intensity to said equivalent absolute spherical volume.

3. The method of either of claim 1 or 2 where the step of measuring the absolute radius of said particle using forward angle light scatter intensity information from said flow cytometer includes the step of using Fraunhofer Diffraction Theory to derive an empirical equation relating the absolute particle radius to forward angle light scatter intensity.

4. The method of claim 3 wherein the empirical equation relating absolute particle radius to forward angle light scatter intensity comprises a fitted polynomial equation provided by determining, by a method of least squares, the best fit values of C, $\theta_{min}$, and $\theta_{max}$ by comparing calculated forward angle light scatter intensity to actual measured forward angle light scatter intensity, where C is the flux per unit area of the incident light beam, and $\theta_{min}$ and $\theta_{max}$ are the minimum and maximum light scatter angles respectively.

5. A method of determining an absolute radius of a biological particle using a conventional flow cytometer, said method comprising the steps of:

a. characterizing particle sizing parameters of said flow cytometer by measuring in a light scatter detection system in said flow cytometer a total diffracted light scatter intensity associated with at least one calibration bead, said bead having a known size, shape, and refractive index;

b. measuring in said light scatter detection system in said flow cytometer a total diffracted light scatter intensity associated with said particle; and c. correlating said diffracted light scatter intensity associated with said particle to an absolute particle radius by a particle radius correlation means, said correlation means optimized by empirically fitting, using Fraunhofer Diffraction Theory, a theoretical light scatter equation to measured total diffracted light scatter intensity associated with said calibration beads.

6. An apparatus for measuring biological particle size comprising:

a. a flow cytometer having a forward angle light scatter intensity detection system;

b. means for limiting minimum and maximum angles of collection of light scatter by said detection system;

c. processor means for receiving from said detection system forward angle light scatter intensity data associated with a particle in said flow cytometer;

d. said processor means further comprising correlation means to correlate an absolute radius directly from said forward angle light scatter intensity data associated with said particle.

7. The apparatus of claim 4, the correlation means comprising means to calculate an absolute particle radius associated with each of said particles in accordance with an equation empirically derived from a theoretical light scatter equation.

8. The apparatus of claim 4, the correlation means comprising data storage means for storing a lookup table which contains data mapping absolute particle radius to forward angle light scatter, said lookup table generated by empirically fitting a theoretical light scatter equation to actual measured absolute particle data.

9. The apparatus of either of claims 7 or 8, wherein the theoretical light scatter equation is derived from Fraunhofer Diffraction Theory.

* * * * *